(12) United States Patent
Wang et al.

(10) Patent No.: US 7,429,652 B2
(45) Date of Patent: Sep. 30, 2008

(54) COMPOSITIONS AND METHODS FOR GENERATING CHIMERIC HETEROMULTIMERS

(75) Inventors: Caili Wang, San Francisco, CA (US); Pingyu Zhong, Mountain View, CA (US); Shengjiang Liu, Mountain View, CA (US); Peizhi Luo, Sunnyvale, CA (US); Shengfeng Li, Belmont, CA (US); Xinwei Wang, San Jose, CA (US)

(73) Assignee: Abmaxis, Inc., Rahway, NJ (US)

( * ) Notice: Subject to any disclaimer, the term of this patent is extended or adjusted under 35 U.S.C. 154(b) by 158 days.

(21) Appl. No.: 10/911,127

(22) Filed: Aug. 3, 2004

(65) Prior Publication Data
US 2005/0009139 A1    Jan. 13, 2005

Related U.S. Application Data

(62) Division of application No. 09/921,144, filed on Aug. 1, 2001, now Pat. No. 6,833,441.

(51) Int. Cl.
*C07H 21/04* (2006.01)
*C12Q 1/70* (2006.01)
*C12P 21/04* (2006.01)
*C12N 7/00* (2006.01)
*C12N 15/00* (2006.01)
*C12N 5/06* (2006.01)
*A61K 39/395* (2006.01)
*C12P 21/08* (2006.01)

(52) U.S. Cl. .................. 536/23.4; 435/5; 435/69.1; 435/69.7; 435/235.1; 435/320.1; 435/328; 530/387.3; 424/133.1

(58) Field of Classification Search .................. None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,091,513 A | 2/1992 | Huston et al. | |
| 5,233,409 A | 8/1993 | Schwab | |
| 5,270,202 A | 12/1993 | Raychaudhuri | |
| 5,348,867 A | 9/1994 | Georgiou et al. | |
| 5,403,484 A | 4/1995 | Ladner et al. | |
| 5,405,783 A | 4/1995 | Pirrung et al. | |
| 5,412,087 A | 5/1995 | McGall et al. | |
| 5,445,934 A | 8/1995 | Fodor et al. | |
| 5,514,548 A | 5/1996 | Krebber et al. | |
| 5,571,698 A | 11/1996 | Ladner et al. | |
| 5,693,762 A * | 12/1997 | Queen et al. | 530/387.3 |
| 5,695,937 A | 12/1997 | Kinzler et al. | |
| 5,731,168 A | 3/1998 | Carter et al. | |
| 5,738,996 A | 4/1998 | Hodges et al. | |
| 5,807,706 A | 9/1998 | Carter et al. | |
| 5,821,333 A | 10/1998 | Carter et al. | |
| 5,824,483 A | 10/1998 | Houston, Jr. et al. | |
| 5,830,721 A | 11/1998 | Stemmer et al. | |
| 5,837,500 A | 11/1998 | Ladner et al. | |
| 5,849,500 A | 12/1998 | Breitling et al. | |
| 5,858,657 A | 1/1999 | Winter et al. | |
| 5,869,337 A | 2/1999 | Crabtree et al. | |
| 5,885,793 A | 3/1999 | Griffiths et al. | |
| 5,910,573 A | 6/1999 | Plükthun et al. | |
| 5,932,448 A | 8/1999 | Tso et al. | |
| 5,955,341 A | 9/1999 | Kang et al. | |
| 5,965,368 A | 10/1999 | Vidal et al. | |
| 5,969,108 A | 10/1999 | McCafferty et al. | |
| 6,010,884 A | 1/2000 | Griffiths et al. | |
| 6,027,930 A | 2/2000 | Borrebaeck | |
| 6,083,693 A | 7/2000 | Nandabalan et al. | |
| 6,127,132 A | 10/2000 | Breitling et al. | |
| 6,129,914 A | 10/2000 | Weiner et al. | |
| 6,130,037 A | 10/2000 | Lennox et al. | |
| 6,132,963 A | 10/2000 | Brent et al. | |
| 6,140,471 A | 10/2000 | Johnson et al. | |

(Continued)

FOREIGN PATENT DOCUMENTS

EP    0 368 684 B1    9/1994

(Continued)

OTHER PUBLICATIONS

Arndt et al. (J. Mol. Biol. 295:627-639 (2000).*

(Continued)

*Primary Examiner*—David J. Blanchard
(74) *Attorney, Agent, or Firm*—Patricia L. Chisholm; William Krovatin

(57) ABSTRACT

The present invention provides a technique for specific assembly of monomeric polypeptides to form a heteromultimer. This technique is particularly useful for generating a genetically diverse repertoire of heteromultimers such as antigen-binding units. The invention also provides both non-single-chain and single-chain antigen-binding units that are assembled by the technique described herein. The present invention also provides recombinant polynucleotides, vectors, host cells, and kits for producing the subject antigen-binding units. Further provided by the invention are methods of using the subject antigen-binding units.

31 Claims, 25 Drawing Sheets

U.S. PATENT DOCUMENTS

| | | | |
|---|---|---|---|
| 6,159,705 | A | 12/2000 | Truehart et al. |
| 6,165,793 | A | 12/2000 | Stemmer |
| 6,171,792 | B1 | 1/2001 | Brent et al. |
| 6,174,708 | B1 | 1/2001 | Sodoyer et al. |
| 6,180,406 | B1 | 1/2001 | Stemmer |
| 6,248,516 | B1 | 6/2001 | Winter et al. |

FOREIGN PATENT DOCUMENTS

| | | |
|---|---|---|
| EP | 0 699755 A2 | 6/1996 |
| EP | 0 699755 A3 | 6/1996 |
| WO | WO 88/06630 | 9/1988 |
| WO | WO 90/02809 | 2/1990 |
| WO | WO 90/05144 | 5/1990 |
| WO | WO 91/17271 | 11/1991 |
| WO | WO 92/01047 | 1/1992 |
| WO | WO 92/15679 | 9/1992 |
| WO | WO 93/10247 | 5/1993 |
| WO | WO 93/11236 | 6/1993 |
| WO | WO 95/26400 | 10/1995 |
| WO | WO 97/08320 | 3/1997 |
| WO | WO 99/14319 | 3/1999 |
| WO | WO 99/42597 | 8/1999 |
| WO | WO 00/14222 | 3/2000 |
| WO | WO 01/05950 A2 | 1/2001 |

OTHER PUBLICATIONS

Pluckthun (Immunotechnology 3:83-105 (1997).*
Stratgene Catalog (1988).*
Abel and Maniatis, (1989) "Gene Regulation. Action of Leucine Zippers," *Nature*, 341(6237):24-5.
Adey, et al., (1996) "Construction of Random Peptide Libraries In Bacteriophage M13," Chapter 5, *Phage Display of Peptides and Proteins: A Laboratory Manual*, Academic Press, Inc.
Arndt, et al., (2001) "Helix-stabilized Fv (hsFv) Antibody Fragments: Substituting the Constant Domains of a Fab Fragment for a Heterodimeric Coiled-coil Domain," *J. Mol. Biol.*, 312:221-228.
Armstrong, et al., (1996) "Vectors For Phage Display," Chapter 3, *Phage Display of Peptides and Proteins: A Laboratory Manual*, Academic Press, Inc.
Ausubel, et al., eds., (1987) "Current Protocols In Molecular Biology" [Table of Contents provided].
Ausubel, et al., eds., (1995) "Short Protocols In Molecular Biology" Third Edition [Table of Contents provided].
Baker, et al., (1987) "Genetics and Biochemistry of the Assembly of Proteins Into the Outer Membrane of *E. coli*," *Prog Biophys Mol Biol*, 49(2-3):89-115.
Banerji, et al., (1983) "A Lymphocyte-Specific Cellular Enhancer Is Located Downstream of the Joining Region In Immunoglobulin Heavy Chain Genes" *Cell*, 33(3):729-740.
Barbas, et al., (2001) *Phage Display: A Laboratory Manual*, Cold Spring Harbor Laboratory Press [Table of Contents provided].
Barbas, et al., (1991) "Assembly of Combinatorial Antibody Libraries On Phage Surfaces: the Gene III Site," *Proc Natl Acad Sci U S A*, 88(18):7978-7982.
Barbas, et al., (1992) "Semisynthetic Combinatorial Antibody Libraries: A Chemical Solution to the Diversity Problem," *Proc Natl Acad Sci U S A*, 89(10):4457-4461.
Barnes, et al., (1980) "Methods for Growth of Cultured Cells in Serum-Free Medium," *Anal. Biochem.*, 102(2):255-270.
Belshaw, et al., (1996) "Controlling Protein Association and Subcellular Localization With a Synthetic Ligand That Induces Heterodimerization of Proteins" *Proc. Natl. Acad. Sci. U.S.A.*, 93(10):4604-4607.
Benson, et al. (1987) "In Vivo Selection and Characterization of Internal Deletions in the LamB::IacZ Gene Fusion" *Gene*, 52(2-3):165-73.
Benson, et al., (1984) "Intragenic Regions Required For LamB Export" *Proc. Natl. Acad. Sci U.S.A.*, 81(12):3830-34.
Bird, et al., (1988) "Single-Chain Antigen-Binding Proteins" *Science*, 242(4877):423-426.

Blankenstein, et al., (1988) "A Retroviral Expression Vector Containing Murine Immunoglobulin Heavy Chain Promoter/Enhancer" *Nucleic Acid Res.*, 16(22):10939.
Brinkmann, et al., (1993) "A Recombinant Immunotoxin Containing a Disulfide-Stabilized Fv Fragment" *Proc. Natl. Acad. Sci. U.S.A.*, 90(16):7538-7542.
Burkhard, et al., (2001) "Coiled Coils: A Highly Versatile Protein Folding Motif," *Trends in Cell Biology*, 11(2):82-88.
Cantley, et al. (1991) "Oncogenes and Signal Transduction," *Cell*, 64(2):281-302.
Chatal, et al., (1985) "Clinical Prospective Study With Radioiodinated Monoclonal Antibodies Directed Against Colorectal Cancer," *Monoclonal Antibodies for Cancer Detection and Therapy*, Academic Press, Chapter 8, pp. 159-180.
Cohen, et al., (1989) "The Product of a Fos-Related Gene, Fra-1, Binds Cooperatively to the AP-1 Site With Jun: Transcription Factor AP-1 Is Comprised of Multiple Protein Complexes," *Genes Dev.*, 3(2):173-84.
Cook and Tomlinson, (1995) "The Human Immunoglobulin VH Repertoire," *Immunol Today*, 16(5):237-242.
Cornelis, (2000) "Expressing Genes In Different *Escherichia coli* Compartments," *Curr Opin Biotechnol.*, 11(5):450-454.
Crameri and Suter, (1993) "Display of Biologically Active Proteins on the Surface of Filamentous Phages: a cDNA Cloning System for Selection of Functional Gene Products Linked to the Genetic Information Responsible for Their Production," *Gene*, 137(1):69-75.
Daugherty, et al. (1999) "Development of An Optimized Expression System for the Screening of Antibody Libraries Displayed on the *Escherichia coli* Surface," *Protein Eng.*, 12(7):613-621.
de Geus, et al., (1984) "The Pro- and Mature Forms of the *E. coli* K-12 Outer Membrane Phospholipase A Are Identical" *EMBO J.*, 3(8):1799-1802.
De Haard, et al., (1999) "A Large Non-Immunized Human Fab Fragment Phage Library That Permits Rapid Isolation and Kinetic Analysis of High Affinity Antibodies," *J Biol Chem.*, 274(26):18218-18230.
De Kruif and Logtenberg, (1986) "Leucine Zipper Dimerized Bivalent and Bispecific scFv Antibodies From a Semi-synthetic Antibody Phage Display Library," *J. Biol. Chem.*, 271 (13):7630-7634.
Donovan, et al., (1987) "Genes Encoding Spore Coat Polypeptides From *Bacillus subtilis*," *J Mol Biol.*, 196(1):10.
Frank, et al., (2000) "A Distinct Seven-Residue Trigger Sequence Is Indispensable For Proper Coiled-Coil Formation of the Human Macrophage Scavenger Receptor Oligomerization Domain" *J. Biol. Chem.*, 275(16):11672-11677.
Freshney, (1987) "Animal Cell Culture" [Table of Contents provided].
Gillies, et al., (1983) "A Tissue-Specific Transcription Enhancer Element Is Located In The Major Intron of a Rearranged Immunoglobulin Heavy Chain Gene"*Cell*, 33(3):717-728.
Glaser, et al., (1992) "Dissection of the Combining Site In a Humanized Anti-Tac Antibody" *J. Immunol.*, 149(8):2607-2614.
Glockshuber, et al., (1990) "A Comparison of Strategies to Stabilize Immunoglobulin Fv-Fragments" *Biochemistry*, 29(6):1362-1367.
Goeddel, ed., "Gene Expression Technology," Academic Press, Inc. [Table of Contents provided].
Gentz, et al., (1989) "Parallel Association of Fos and Jun Leucine Zippers Juxtaposes DNA Binding Domains," *Science*, 243(4899):1695-9.
Geoffroy, et al. (1994) A New Phage Display System to Construct Multicombinatorial Libraries of Very Large Antibody Repertoires. *Genes*, 151(1-2):109-13.
Gomes, et al., (2000) "Heterodimerization of Mu and Delta Opiod Receptors: A Role in Opiate Synergy," *J. Neurosci.*, 20(22):RC110.
Gram, et al., (1992) "In Vitro Selection and Affinity Maturation of Antibodies From a Naive Combinatorial Immunoglobulin Library," *Proc Natl Acad Sci U S A*, 89(8):3576-3580.
Griffiths, et al., (1994) "Isolation of High Affinity Human Antibodies Directly From Large Synthetic Repertoires," *EMBO J.*, 13(14):3245-3260.
Gudmundsdottir, et al., (1989) "Point Mutations in a Conserved Region (TonB Box) of *Escherichia coli* Outer Membrane Protein BtuB Affect Vitamin B12 Transport," *J Bacteriol.*, 171(12):6526-33.

Hantzopoulos, et al., (1989) "Improved Gene Expression Upon Transfer of the Adenosine Deaminase Minigene Outside the Transcriptional Unit of a Retroviral Vector" *Proc. Natl. Acad. Sci. U.S.A.*, 86(10):3519-3523.

Harlow and Lane (1988) "Antibodies: A Laboratory Manual," Cold Spring Harbor Laboratory, New York [Table of Contents provided].

Hawkins, et al., (1992) "Selection of Phage Antibodies By Binding Affinity, Mimicking Affinity Maturation," *J Mol Biol.*, 226(3):889-896.

Holliger, et al., (1993) "'Diabodies': Small Bivalent and Bispecific Antibody Fragments," *Proc. Natl. Acad. Sci. U.S.A.*, 90(14):6444-6448.

Hoogenboom and Charnes, (2000) "Natural and Designer Binding Sites Made By Phage Display Technology," *Immunology Today*, 21(8):371-378.

Huston, et al., (1988) "Protein Engineering of Antibody Binding Sites: Recovery of Specific Activity in An Anti-Digoxin Single-Chain Fv Analogue Produced In *Escherichia coli*,"*Proc. Natl. Acad. Sci. U.S.A.*, 85(16):5879-5883.

Jabet, et al., (1999) "NMR Studies of the Pbx1 TALE Homeodomain Protein Free in Solution and Bound to DNA: Proposal for A Mechanism of HoxB1-Pbx1-DNA Complex Assembly," *J Mol Biol.* 291(3):521-530.

Jansen, et al., (1985) "Efficiency and Tolerance of the Treatment With Immuno-A-Chain-Toxins in Human Bone Marrow Transplantations," *Monoclonal Antibodies for Cancer Detection and Therapy*, Academic Press, Chapter 11, pp. 223-248.

Jordan, et al., (1999) "G-Protein-Coupled Receptor Heterodimerization Modulates Receptor Function," *Nature*, 399(6737):697-700.

Junius, et al., (1996) "High Resolution NMR Solution Structure of the Leucine Zipper Domain of the c-Jun Homodimer," *J. Biol. Chem.*, 271(23):13663-13667.

Kammerer, et al., (1998) "An Autonomous Folding Unit Mediates The Assembly of Two-Stranded Coiled Coils," *Biochemistry*, 95(23):13419-13424.

Kammere, et al., (1999) "Heterodimerization of a Functional $GABA_B$ Receptor Is Mediated by Parallel Coiled-Coil a-Helices," *Biochemistry*, 38(40):13263-13269.

Kang, et al., (1991) "Linkage of Recognition and Replication Functions By Assembling Combinatorial Antibody Fab Libraries Along Phage Surfaces," *Proc Natl Acad Sci U S A*, 88(10):4363-4366.

Kay, et al., (1996) *Phage Display of Peptides and Proteins: A Laboratory Manual*, Academic Press, Inc. [Table of Contents provided].

Kay and Hoess, (1996) "Principles and Applications of Phage Display," Chapter 2, *Phage Display of Peptides and Proteins: A Laboratory Manual*, Academic Press, Inc.

Kim, et al., (1999) "Cell Surface Display of Hepatitis B Virus Surface Antigen By Using *Pseudomonas syringae* Ice Nucleation Protein," *Lett Appl Microbiol.*, 29(5):292-7.

Kuner, et al., (1999) "Role of Heteromer Formation in $GABA_B$ Receptor Function," *Science*, 283(5398):74-77.

Lang, (2000) "Outer Membrane Proteins as Surface Display Systems," *Int J Med Microbiol.*, 290(7):579-585.

Larrick, et al., (1989) "Rapid Cloning of Rearranged Immunoglobulin Genes From Human Hybridoma Cells Using Mixed Primers and the Polymerase Chain Reaction," *Biochem. Biophys. Rev. Commun.*, 160(3):1250-1255.

Levitt, et al., (1983) "Molecular Dynamics of Native Protein. I. Computer Simulation of Trajectories," *J. Mol. Biol.*, 168:595-617.

Light, et al., (1996) "Expression Cloning of cDNA By Phage Display Selection," *Nucleic Acids Research*, 24(21):4367-4368.

Liscovitch, et al., (1994) "Lipid Second Messengers," *Cell*, 77(3):329-34.

Little, et al., (2000) "Of Mice and Men: Hybridoma and Recombinant Antibodies," *Immunology Today*, 21(8):364-370.

Losick, et al., (1986) "Genetics of Endospore Formation in *Bacillus subtilis*," *Annu Rev Genet.*, 20:625-69.

Luiten, et al., (1985) "Nucleotide Sequence of the Genome of Pf3, An IncP-1 Plasmid-Specific Filamentous Bacteriophage of *Pseudomonas aeruginosa*,"*J Virol.*, 56(1):268-76.

Luiten, et al., (1991) "In Vitro Deletion Mapping of the Viral Strand Replication Origin of *Pseudomonas* Bacteriophage Pf3,"*J Bacteriol.*, 173(13):4007-12.

Marks, et al., (1991) "By-Passing Immunization. Human Antibodies From V-Gene Libraries Displayed on Phage,"*J Mol Biol.*, 222(3):581-597.

Mason, et al., (1985) "Transcription Cell Type Specificity is Conferred By An Immunoglobulin VH Gene Promoter That Includes a Functional Consensus Sequence," *Cell*, 41(2):479-487.

Matthews, (1991) "Plant Virology," 3rd edition.

McCafferty, et al., (1990) "Phage Antibodies: Filamentous Phage Displaying Antibody Variable Domains," *Nature*, 348(6301):552-4.

McIvor, et al., (1987), "Human Purine Nucleoside Phosphorylase and Adenosine Deaminase: Gene Transfer Into Cultured Cells and Murine Hematopoietic Stem Cells By Using Recombinant Amphotropic Retroviruses," *Mol. Cell. Biol.*, 7(2):838-846.

McPherson, et al., eds. (1995) "PCR 2: A Practical Approach" [Table of Contents provided].

Miltenyi, et al., (1990) "High Gradient Magnetic Cell Separation With MACS," *Cytometry*, 11(2):231-238.

Misra, et al., (1988) "Isolation and Characterization of OmpC Porin Mutants With Altered Pore Properties," *J Bacteriol.*, 170(2):528-33.

Myers (1985) "The Use of Immunotoxins to Eliminate Tumor Cells From Human Leukaemic Marrow Autografts," *Monoclonal Antibodies for Cancer Detection and Therapy*, Academic Press, Chapter 12, pp. 249-267.

Nakabeppu, et al., (1988) "DNA Binding Activities of Three Murine Jun Proteins: Stimulation By Fos.," *Cell*, 55(5):907-15.

O'Shea, et al., (1992) "Mechanism of Specificity in the Fos-Jun Oncoprotein Heterodimer," *Cell*, 68(4):699-708.

Olsnes and Pihl, (1981) "Chimeric Toxins," *Pharmac. Ther.*, 15(3):355-381.

Orlandi, et al. (1989) "Cloning Immunoglobulin Variable Domains For Expression By the Polymerase Chain Reaction," *Proc. Natl. Acad. Sci. U.S.A.*, 86(10):3833-3837.

Pages, et al., (1990) "Immunoglobulin Approach of Assembly and Topology of OmpF, an Outer Membrane Protein of *Escherichia coli*," *Biochemimie*, 72(2-3):169-76.

Parmley, et al., (1988) "Antibody-Selectable Filamentous fd Phage Vectors: Affinity Purification of Target Genes," *Gene*, 73(2):305-18.

Peng, et al., (1988) "Retroviral-Mediated Gene Transfer and Expression of Human Phenylalanine Hydroxylase in Primary Mouse Hepatocytes," *Proc. Natl. Acad. Sci. U.S.A.*, 85(21):8146-8150.

Pini, et al. (1998) "Design and Use of a Phage Display Library. Human Antibodies With Subnanomolar Affinity Against a Marker of Angiogenesis Eluted From a Two-Dimesional Gel," *J Biol Chem.*, 273(34):21769-21776.

Piper, et al., (1999) "Structure of a HoxB1-Pbx1 Heterodimer Bound to DNA: Role of the Hexapeptide and a Fourth Homeodomain Helix in Complex Formation," *Cell*, 96(4):587-597.

Rider, et al., (1996) "Microbiological Methods," Chapter 4, *Phage Display of Peptides and Proteins: A Laboratory Manual*, Academic Press, Inc.

Rondot, et al., (2001) "A Helper Phage to Improve Single-Chain Antibody Presentation in Phage Display," *Nature Biotechnology*, 19(1):75-78.

Sambrook, et al., (1989) "Molecular Cloning: A Laboratory Manual," 2nd edition [Table of Contents provided].

Sanford, et al., (1993) "Optimizing the Biolistic Process for Different Biological Applications," *Methods in Enzymology*, 217:483-509.

Sastry, et al., (1989) "Cloning of the Immunological Repertoire in *Escherichia coli* for Generation of Monoclonal Catalyic Antibodies: Construction of a Heavy Chain Variable Region-Specific cDNA Library," *Proc. Natl. Acad. Sci. U.S.A.*, 86(15):5728-5732.

Sato, et al., (1982) "Growth of Cells in Hormonally Defined Media," Cold Spring Harbor Press, N.Y. [Table of Contents provided].

Sblattero, et al, (1997) "A Definitive Set of Oligonucleotide Primers for Amplifying Human V Regions," *Immunotechnology*, 3(4):271-278.

Schuler, et al., "Methods in Plant Molecular Biology," Academic Press, Inc. [Table of Contents Provided].

Scott and Barbas, (2001) "Phage-Display Vectors," Chapter 2, *Phage Display: A Laboratory Manual*, Cold Spring Harbor Laboratory Press.

Shalaby, et al., (1992) "Development of Humanized Bispecific Reactive with Cytotoxic Lymphocytes and Tumor Cells Overexpressing the HER2 Protooncogene," *J. Exp. Med.*, 175(1):217-225.

Sheets, et al., (1998) "Efficient Construction of a Large Nonimmune Phage Antibody Library: the Production of High-Affinity Human Single-Chain Antibodies to Protein Antigens," *Proc Natl Acad Sci U S A*, 95(11):6157-6162.

Sidhu, (2000) "Phage Display in Pharmaceutical Biotechnology," *Curr Opin Biotechnol.*, 11(6):610-616.

Smith, et al., (1985) "Filamentous Fusion Phage: Novel Expression Vectors that Display Cloned Antigens on the Virion Surface," *Science*, 228(4705):1315-17.

So, et al., (1985) "Gonococcal Pilus: Genetics and Structure," *Curr Top in Microbiol & Immunol*, 118:13-28.

Soderlind, et al. (2000) "Recombining Germite-Derived CDR Sequences for Creating Diverse Single-Framework Antibody Libraries," *Nat Biotechnol.*, 18(8):852-856.

Songyang, et al., (1993) "SH2 Domains Recognize Specific Phosphopeptide Sequences" *Cell*, 72(5):767-778.

Songyang, et al., (1995) "A Single Point Mutation Switches the Specificity of Group III Src Homology (SH) 2 Domains to That of Group I SH2 Domains" *J. Biol. Chem.*, 270(44):26029-26032.

Stemmer, et al., (1993) "Selection of an Active Single Chain Fv Antibody From a Protein Linker Library Prepared by Enzymatic Inverse PCR," *Biotechniques*, 14(2):256-265.

Tabin, et al., (1982) "Adaptation of a Retrovirus as a Eucaryotic Vector Transmitting the Herpes Simplex Virus Thymidine Kinase Gene," *Mol. Cell. Biol.*, 2(4):426-436.

Tempest, et al., (1991) "Reshaping a Human Monoclonal Antibody to Inhibit Human Respiratory Syncytial Virus Infection In Vivo," *Biotechnology*, 9(3):266-271.

Thorpe, et al., (1982) "Monoclonal Antibody-Toxin Conjugates: Aiming the Magic Bullet," *Monoclonal Antibodies in Clinical Medicine*, Academic Press, pp. 168-190.

van Assendelft, et al., (1989) "The Beta-Globin Dominant Control Region Activates Homologous and Heterologous Promoters in a Tissue-Specific Manner," *Cell*, 56(6):969-977.

van der Ley, et al., (1986) "Topology of Outer Membrane Pore Protein PhoE of *Escherichia coli*," *J. Biol. Chem.*, 261(26):12222-12225.

Vidal, et al., (1996) "Reverse Two-Hybrid and One-Hybrid Systems to Detect Dissociation of Protein-Protein and DNA Protein Interactions," *Proc. Natl. Acad. Sci. U.S.A*, 93(19):10315-10320.

Viega, et al., (1999) "Probing Secretion and Translocation of a Beta-Autotransporter Using a Reporter Single-Chain Fv as a Cognate Passenger Domain," *Mol Microbiol.*, 33(6):1232-43.

Vitetta, et al. (1987) "Redesigning Nature's Poisons to Create Anti-Tumor Reagents," *Science*, 238(4830):1098-1104.

Ward, et al., (1989) "Binding Activities of a Repertoire of Single Immunoglobulin Variable Domains Secreted from *Escherichia coli*," *Nature*, 341(6242):544-546.

Waterhouse, et al., (1993) "Combinatorial Infection and In Vivo Recombination: a Strategy for Making Large Phage Antibody Repertories," *Nucleic Acids Res.*, 21(9):2265-6.

White, et al., (1998) "Heterodimerization is Required for the Formation of a Functional $BABA_B$ Receptor," *Nature*, 396(6712):679-682.

Winter and Milstein (1991) "Man-made Antibodies," *Nature*, 349(6307):293-299.

Winter, et al., (1994) "Making Antibodies By Phage Display Technology," *Ann. Rev. Immunol.*, 12:433-455.

Wolf, et al., (1997) "MultiCoil: A Program for Predicting Two- and Three-Stranded Coiled Coils," *Protein Sci.*, 6(6):1179-1189.

Zhou et al., (1983) "Introduction of Exogenous DNA into Cotton Embryos," *Methods in Enzymology*, 101:433-481.

Hudson, P.J., "Recombinant Antibodies: A Novel Approach to Cancer Diagnosis and Therapy," Expert Opinion on Investigational Drugs, Jun. 2000, 1231-1242, vol. 9, No. 6, Ashley Publications Ltd., London, GB.

Kostelny, S.A., et al., "Formation of a Bispecific Antibody by the Use of Leucine Zippers," Journal of Immunology, Mar. 1, 1992, 1547-1553, vol. 148, No. 5, The Williams and Wilkins Co., Baltimore, US.

Müller, K.M., et al., "The First Constant Domain (CHI and CL) of an Antibody Used as Heterodimerization Domain for Bispecific Miniantibodies," FEBS Letters, 1998, 259-264, vol. 422, No. 2, Elsevier Science Publishers, Amsterdam, NL.

Pack, P. et al., "Minicantibodies: Use of Amphipatic Helices to Produce Functional, Flexibly Linked Dimeric FV Fragments with High Avidity in *Escherichia coli*," Biochemistry, Feb. 18, 1992, 1579-1584, vol. 31, No. 6, American Chemical Society, Easton, PA.

Schoonjans, R., et al., "A New Model for Intermediate Molecular Weight Recombinant Bispecific and Trispecific Antibodies by Efficient Heterodimerization of Single Chain Variable Domains Through Fusion to a Fab-Chain," Biomolecular Engineering, Jun. 2001, 193-202, vol. 17, No. 6, Elsevier Science B.V.

\* cited by examiner

Sequences of coiled-coil domain in ccFv

GR1 Sequence Range: 1 to 146

```
         XbaI    10         20         30         40         50
         TCTAGAGGTGGAGGAGGTGAGGAGAAGTCCGGCTGTTGGAGAAGGAGAA
          S  R  G  G  G  G  E  E  K  S  R  L  L  E  K  E  N
              60         70         80         90        100
         CCGTGAACTGGAAAAGATCATTGCTGAGAAAGAGGAGCGTGTCTCTGAAC
          R  E  L  E  K  I  I  A  E  K  E  E  R  V  S  E
             110        120        130        140 AscI
         TGCGCCATCAACTCCAGTCTGTAGGAGGTTGTTAATAGGGGCGCGCC
          L  R  H  Q  L  Q  S  V  G  G  C  *  *
```

GR2 Sequence Range: 1 to 140

```
         XhoI    10         20         30         40         50
         TCTCGAGGAGGTGGTGGAACATCCGCCTGGAGGGCCTACAGTCAGAAAA
          S  R  G  G  G  G  T  S  R  L  E  G  L  Q  S  E  N
              60         70         80         90        100
         CCATCGCCCTGCAATGAAGATCACAGAGCTGGATAAAGACTTGGAAGAGG
          H  R  L  R  M  K  I  T  E  L  D  K  D  L  E  E
             110        120        130 NotI 140
         TCACCATGCAGCTGCAGGACGTCGGAGGTTGCCGCGGCCGC
          V  T  M  Q  L  Q  D  V  G  G  C  A  A  A
```

Fig. 2

PABMX1 vector: sequence from AgeI to BglII

```
      lac promoter/lac O1         AgeI            EP           S/D
AATTGTGAGCGGATAACAATTT ACCGGT TCTT TTAACTTTAG TAAGGAGG AATTAAAAA
                      P8 Leader                              HindIII       XbaI
ATGAAAAAGTCTTTAGTCCTCAAAGCCTCCGTAGCCGTTGCTACCCTCGTTCCGATGCTAAGCTTCGCT TCTAGA
 M  K  K  S  L  V  L  K  A  S  V  A  V  A  T  L  V  P  M  L  S  F  A   S  R
  NotI                            HA-tag                    His-tag          BglII
GCGGCCGCT TATCCATACGACGTACCAGACTACGCA GGAGGT CATCCACCATCATCACCAT TAG AGATCT
 A  A  A  Y  P  Y  D  V  P  D  Y  A    G  G   H  H  H  H  H  H   *   R  S
```

PABMX2 vector: sequence from AgeI to BglII

```
      lac promoter/lac O1         AgeI            EP           S/D
AATTGTGAGCGGATAACAATTT ACCGGT TCTT TTAACTTTAG TAAGGAGG AATTAAAAA
                      pelB Leader                               NcoI           PstI         XbaI
ATGAAATACCTATTGCCTACGGCAGCCGCTGGATTGTTATTACTCGCGGCCCAGCCGGCCATGGCGGCCCTGCAGGCCTCTAGA
 M  K  Y  L  L  P  T  A  A  A  G  L  L  L  L  A  A  Q  P  A  M  A  A  L  Q  A  S  R
  NotI                            HA-tag                    His-tag          BglII
GCGGCCGCT TATCCATACGACGTACCAGACTACGCA GGAGGT CATCCACCATCATCACCAT TAG AGATCT
 A  A  A  Y  P  Y  D  V  P  D  Y  A    G  G   H  H  H  H  H  H   *   R  S
```

Fig. 3B

PABMD1 vector: sequence from AgeI to SalI

```
     lac promoter/lac O1           AgeI            EP       S/D
AATTGTGAGCGGATAACAATTT ACCGGT TCTT TTAACTTTAG TAAGGAGG AATTAAAAA
                              P8 Leader
ATGAAAAAGTCTTTAGTCCTCAAAGCCTCCGTAGCCGTTGCTGTTGCTACCCTCGTTCCGATGCTAAGCTTCGCT TCTAGA
                                                                  HindIII       XbaI
 M  K  K  S  L  V  L  K  A  S  V  A  V  A  T  L  V  P  M  L  S  F  A   S  R
 NotI                           HA-tag                          His-tag   Amber stop  BglII
GCGGCCGCT TATCCATATGACGACGTTCCAGACTACGCA GGAGGT CATCACCATCATCACCAT TAG     AGATCT
 A  A  A  Y  P  Y  D  V  P  D  Y  A  G  G  H  H  H  H  H  H   *          R  S
                                                                                      SalI
GGAGGCGGT ACTGTTGAAAGTTGTTTAGCAAAA ---- GCTAACATACTGCGTAATAAGGAGTCTTAA GTCGAC
 G  G  G  T  V  E  S  C  L  A  K  ----  A  N  I  L  R  N  K  E  S   *
                Gene 3
```

PABMD2 vector: sequence from AgeI to SalI

```
     lac promoter/lac O1           AgeI            EP       S/D
AATTGTGAGCGGATAACAATTT ACCGGT TCTT TTAACTTTAG TAAGGAGG AATTAAAAA
                              pelB Leader
ATGAAATACCTATTGCCTACGGCAGCCGCTGGATTGTTATTACTCGCGGCCCAGCCGGCCATGGCGGCCCAGCCGGCCCTGCAGGCCTCTAGA
                                                         NcoI             PstI            XbaI
 M  K  Y  L  L  P  T  A  A  A  G  L  L  L  L  A  A  Q  P  A  M  A  A  A  L  Q  A  S  R
 NotI                           HA-tag                          His-tag   Amber stop  BglII
GCGGCCGCT TATCCATATGACGACGTTCCAGACTACGCA GGAGGT CATCACCATCATCACCAT TAG     AGATCT
 A  A  A  Y  P  Y  D  V  P  D  Y  A  G  G  H  H  H  H  H  H   *          R  S
                                                                                      SalI
GGAGGCGGT ACTGTTGAAAGTTGTTTAGCAAAA ---- GCTAACATACTGCGTAATAAGGAGTCTTAA GTCGAC
 G  G  G  T  V  E  S  C  L  A  K  ----  A  N  I  L  R  N  K  E  S   *
                Gene 3
```

Fig. 4B

PABMX5 vector: sequence from p8 leader to DH-tag

```
                P8 Leader                                    HindIII              XbaI
ATGAAAAAGTCTTTAGTCCTCAAAGCCCTCGTAGCCGTTGCTACCCTCGTTGTCCGATGCTAAGCTTCGCT    TCTAGA
 M  K  K  S  L  V  L  K  A  S  V  A  V  A  T  L  V  P  M  L  S  F  A          S  R
                              AscI                     S/D             P3 Leader
                              GGCGCGCCACAATTCACAGTAAGGAGGTTTAACTT ATGAAAAAATTATTCGCAATTCCTTTAGTTGTTCCT
                                                                   M  K  K  L  L  F  A  I  P  L  V  V  P
                              MluI          XhoI                                       HA-tag
TTCTATTCTCACTCCGCTACGCGT      TCTCGA    GR2      GCGGCCGCTTATCCATACGACGTACCAGACTACGCA
 F  Y  S  H  S  A  T  R        S  R              A  A  A  Y  P  Y  D  V  P  D  Y  A
         His-tag                              NotI
GGAGGT CATCACCATCATCACCAT TAG *
 G  G   H  H  H  H  H  H   *
```

PABMX6 vector: sequence from pelB leader to DH-tag

```
                pelB Leader                                       NcoI               XbaI
ATGAAATATACCTATTGCCTACGGCTGCTGATTGTTATTACTCGCGGCCCAGCCGGCCATGGCG    VH    TCTAGA
 M  K  Y  L  P  T  A  A  A  G  L  L  L  A  A  Q  P  A  M  A              S  R
                              AscI                     S/D             P3 Leader
                              GGCGCGCCACAATTCACAGTAAGGAGGTTTAACTT ATGAAAAAATTATTCGCAATTCCTTTAGTTGTTCCT
                                                                   M  K  K  L  L  F  A  I  P  L  V  V  P
                              MluI          XhoI                                       HA-tag
TTCTATTCTCACTCCGCTACGCGT      TCTCGA    GR2      GCGGCCGCTTATCCATACGACGTACCAGACTACGCA
 F  Y  S  H  S  A  T  R        S  R              A  A  A  Y  P  Y  D  V  P  D  Y  A
         His-tag                              NotI
GGAGGT CATCACCATCATCACCAT TAG *
 G  G   H  H  H  H  H  H   *
```

Fig. 5B

PABMD5 vector: sequence from HindIII to SalI

```
         P8 Leader                                                                HindIII                              XbaI
ATGAAAAAGTCTTTAGTCCTCAAAGCCTCCGTAGCCGTTGCTACCCTCGTTCCGATGCTAAGCTTCGCT    VH     TCTAGA
 M  K  K  S  L  V  L  K  A  S  V  A  V  A  T  L  V  P  M  L  S  F  A            S  R
                                  AscI              S/D         P3 Leader
      GR1   GGCGGCGCCACAATTCACAGTAAGGAGGTTTAACTT ATGAAAAAATTATTATTGCAATTCCTTTAGTGTTCCT
                                                  M  K  K  L  L  F  A  I  P  L  V  V  P
                        MluI            XhoI                    NotI                                    HA-tag
TTCTATTCTCACTCCGCTACGCGT    VL     TCTCGA GCGGCCGCTTATCCATACGACGTACCAGACTACGCA
 F  Y  S  H  S  A  T  R           S  R    A  A  A  Y  P  Y  D  V  P  D  Y  A
    His-tag                                                                       SalI
GGAGGT CATCACCATCATCACCAT TAG GGAGGCGGT ACTGTTGAAAGTTGT---CTGCGTAATAAGGAGTCTTAA GTCGAC
 G  G  H  H  H  H  H  H   *   G  G  G    T  V  E  S  C  ---  L  R  N  K  E  S  *
                                                  Gene 3
```

PABMX6 vector: sequence from pelB leader to DH-tag

```
       pelB Leader                                                           NcoI                              XbaI
ATGAAATACCTATTGCCTACGGCAGCCCTGGATTGTTATTACTCGCGGCCCAGCCGGCCATGGCG    VH     TCTAGA
 M  K  Y  L  L  P  T  A  A  A  G  L  L  L  L  A  A  Q  P  A  M  A            S  R
                              AscI              S/D         P3 Leader
      GR1   GGCGGCGCCACAATTCACAGTAAGGAGGTTTAACTT ATGAAAAAATTATTATTGCAATTCCTTTAGTGTTCCT
                                                 M  K  K  L  L  F  A  I  P  L  V  V  P
                        MluI            XhoI                    NotI                                    HA-tag
TTCTATTCTCACTCCGCTACGCGT    VL     TCTCGA GCGGCCGCTTATCCATACGACGTACCAGACTACGCA
 F  Y  S  H  S  A  T  R           S  R    A  A  A  Y  P  Y  D  V  P  D  Y  A
    His-tag                                                                       SalI
GGAGGT CATCACCATCATCACCAT TAG GGAGGCGGT ACTGTTGAAAGTTGT---CTGCGTAATAAGGAGTCTTAA GTCGAC
 G  G  H  H  H  H  H  H   *   G  G  G    T  V  E  S  C  ---  L  R  N  K  E  S  *
                                                  Gene 3
```

Fig. 6B

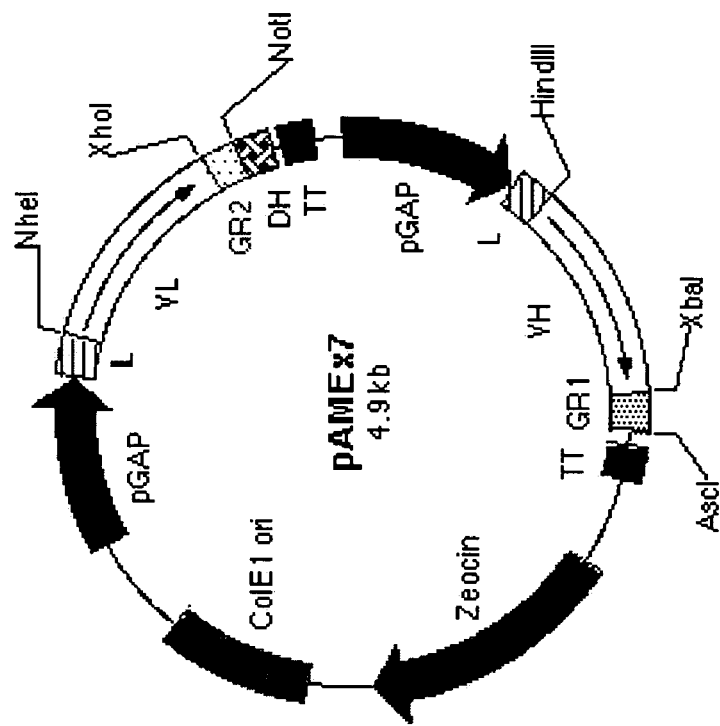
Fig. 7 Vector for ccFv expression in Yeast

AM1-ccFv Antibody display on phage

Comparison of antigen binding capability of AM2-ccFv and AM2-scFv displayed on phage particles

Fig. 11B

Bi-specific antibody (1)
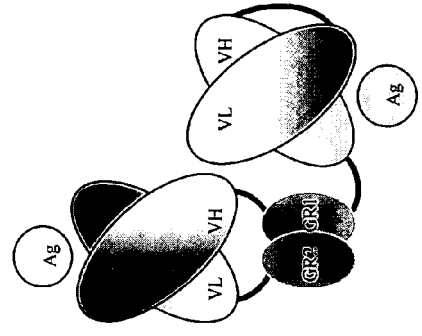
Bi-specific ccFv-scFv'
Peptide 1: VL-GR2-scFv'
Peptide 2: VH-GR1
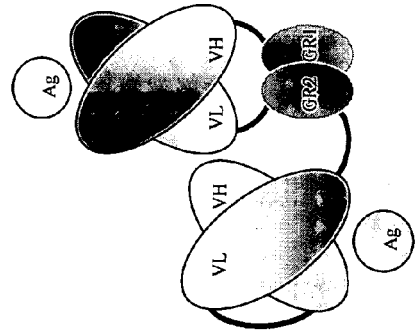
Bi-specific ccFv-scFv'
Peptide 1: VH-GR1-scFv'
Peptide 2: VL-GR2
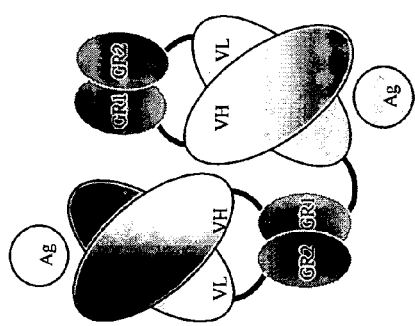
Bi-specific ccFv-ccFv'
Peptide 1: VH-GR1-VL'-GR2
Peptide 2: VL-GR2
Peptide 3: VH'-GR1
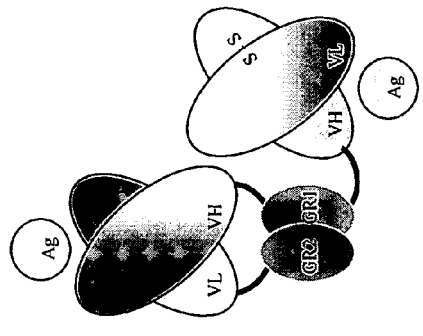
Bi-specific ccFv-dsFv'
Peptide 1: VH-GR1-VH'-s
Peptide 2: VL-GR2
Peptide 3; VL'-s
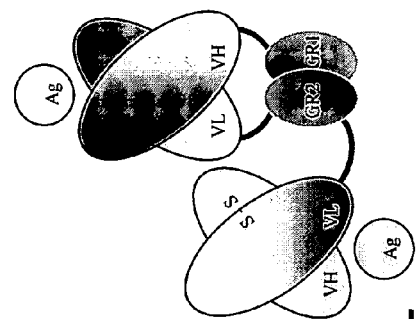
Bi-specific ccFv-dsFv'
Peptide 1: VL-GR2-VL'-s
Peptide 2: VH-GR1
Peptide 3; VH'-s
Fig. 15

US 7,429,652 B2

COMPOSITIONS AND METHODS FOR GENERATING CHIMERIC HETEROMULTIMERS

CROSS REFERENCE TO RELATED APPLICATION

This application is a divisional application of U.S. Utility patent application Ser. No. 09/921,144, filed Aug. 1, 2001, now U.S. Pat. No. 6,833,441, which is hereby incorporated herein by reference in its entirety.

TECHNICAL FIELD

This invention is in the field of immunology. Specifically, the invention relates to the generation of chimeric heteromultimers such as non-single-chain antigen-binding units using unique heterodimerization sequences. This invention also relates to the generation of single-chain antigen-binding units stabilized by the subject heterodimerization sequences. The compositions and methods embodied in the present invention are particularly useful for identifying antigen-binding units that are of major diagnostic and/or therapeutic potential.

BACKGROUND OF THE INVENTION

Antibodies or immunoglobulins are molecules that recognize and bind to specific cognate antigens. Because of their exclusive specificities, antibodies, particularly monoclonal antibodies, have been widely used in the diagnosis and treatment of a variety of human diseases.

The basic immunoglobulin (Ig) in vertebrate systems is composed of two identical light ("L") chain polypeptides (approximately 23 kDa), and two identical heavy ("H") chain polypeptides (approximately 53 to 70 kDa). The four chains are joined by disulfide bonds in a "Y" configuration. At the base of the Y, the two H chains are bound by covalent disulfide linkages. The L and H chains are organized in a series of domains. The L chain has two domains, corresponding to the C region ("CL") and the other to the V region ("VL"). The H chain has four domains, one corresponding to the V region ("VH") and three domains (CH1, CH2 and CH3) in the C region. The antibody contains two arms (each arm being a Fab fragment), each of which has a VL and a VH region associated with each other. It is this pair of V regions (VL and VH) that differ, from one antibody to another (due to amino acid sequence variations), and which together are responsible for recognizing the antigen and providing an antigen-binding site. More specifically, each V region is made up from three complementarity determining regions (CDR) separated by four framework regions (FR). The CDR's are the most variable part of the variable regions, and they perform the critical antigen binding function. The CDR regions are derived from many potential germ line sequences via a complex process involving recombination, mutation and selection.

Research in recent years has demonstrated that the function of a binding antigen can be performed by fragments of a whole antibody. Exemplary antigen binding fragments are (i) the Fab fragment consisting of the VL, VH, CL and CH1 domains; (ii) the Fd fragment consisting of the VH and CH1 domains; (iii) the dAb fragment (Ward, E. S. et al., Nature 341, 544-546 (1989) which consists of a VH domain; (iv) isolated CDR regions; and (v) F(ab')$_2$ fragments, a bivalent fragment comprising two Fab fragments linked by a disulfide bridge at the hinge region; and (vi) the Fv fragment consisting of the VL and VH domains of a single arm of an antibody. The Fv fragment is the smallest functional unit required for high affinity binding of antigen.

One major challenge in the antibody field has been to reconstitute a vast diverse repertoire of immunoglobulins that mimics the immunoglobulin pool in the human immune system. Such a repertoire generally has a complexity ranging from $10^8$ to $10^{13}$ distinct immunoglobulins. The generation of such a repertoire would greatly facilitate the identification and production of immunoglobulins capable of interacting specifically with therapeutic targets. However, the design and production of such a repertoire has traditionally been hampered by the lack of a stabilizing means for assembly of the minimal functional unit, namely the Fv fragment. It is a well-known problem in the art that the VH and VL regions, when expressed alone, have very low interaction energy (Glockshuber et al. (1990) Biochemistry 29(6):1362-1367). The two components dissociate at low protein concentrations and are too unstable for many applications at physiological body temperature. It is also a long-recognized technical obstacle that large proteins, such as whole antibodies (albeit extremely stable), do not express at an appreciable level in the host cell, thus rendering the construction of a highly diverse antibody repertoire very difficult.

More recently, three approaches have been developed to generate stable VL and VH complexes. However, each of these techniques bears a number of intrinsic limitations; and none of them circumvents the aforementioned technical hurdles completely. The first approach uses a peptide linker to connect the VL and VH as a single-chain ("scFv") (Huston et al. (1988) Proc. Natl. Acad. Sci. U.S.A 85:5879-5883). While the resulting scFv exhibits substantial antigen-binding activity, not all antibodies can be made as single chains and still retain high binding affinity (Huston et al. (1988) Proc. Natl. Acad. Sci. U.S.A. 85:5879-5883; Stemmer et al. (1993) Biotechniques 14(2): 256-265). In part, this is due to the interference of linker sequences with the antigen binding sites. The second approach involves inserting a pair of cysteine residues in the VL and VH regions to generate a disulfide-bond stabilized Fv ("dsFv") (Brinkmann et al. (1993) Proc. Natl. Acad. Sci. U.S.A. 90(16): 7538-7542). The incorporated disulfide linkage, however, is unstable under reducing conditions in many host cells. For instance, in cytosol of E. Coli, the inter-molecular disulfide bond is often insufficient to stabilize the VL and VH complex. Moreover, this method typically requires 3-dimensional structural information of the V regions to ensure that the cysteine pair is inserted in a proper place without disruption the binding activity. Because the 3-dimensional information of a vast majority of the existing antibodies is unknown, this approach has little practical utility, and is particularly unsuited for antibody library construction, especially for constructing antibody repertoires derived from B cells. The third approach for stabilizing the VL and VH regions utilizes the disulfide bonds native to the CH1 and CL domains. This method proceeds with grafting a disulfide-bond linked CH1 and CL domains to the C-termini of the VL and VH regions in order to reconstitute a Fab fragment. While the resulting Fab fragment is generally more stable and often exhibits higher binding affinity than scFv, Fab is not optimal for high level expression and antibody repertoire construction due to its large size.

Certain dimerization sequences that form coiled-coil structures have also been employed to assemble multivalent antibodies. Specifically, U.S. Pat. No. 5,932,448 describes a bispecific F(ab')$_2$ heterodimer linked by the Fos and Jun leucine zippers. The Fos and Jun leucine zippers are well-characterized sequences known to preferentially form heterodimers. However, they still exhibit significant propensity to form homodimers under physiological buffer conditions and/or at physiological body temperature (O'Shea et al.

(1992) *Cell* 68: 699-708; Vidal et al. (1996) *Proc. Natl. Acad. Sci. U.S.A.*). In fact, the Jun/Jun homodimer is so stable that formation of Fos1Jun heterodimer in vitro requires dissociation of the Jun/Jun homodimer by first heating or reduction with 2-mercaptoethanylamine (see U.S. Pat. No. 5,910,573 column 7 lines 35-37; U.S. Pat. No. 5,932,448, column 16 lines 15-30). When tested in vivo, both Fos and Jun yield detectable amounts of homodimers (see, e.g. column 15, lines 41-43 of U.S. Pat. No. 5,932,448; and Vidal et al. (1996) *Proc. Natl. Acad. Sci. U.S.A*). While the existence of some homodimerization propensity may not be of substantial concern for the production of a single antibody species, such propensity presents a serious problem for antibody repertoire construction, where high efficiency of heterodimerization between VL and VH regions is required.

Aside from Fos and Jun leucine zippers, U.S. Pat. No. 5,824,483 by Houston et al. describes the construction of a combinatorial library of coiled-coil dimerization peptides. Houston et al. proposes that the library is useful for identifying a polypeptide that is capable of interacting specifically with a selected macromolecule ligand such as antibodies (see last paragraph bridging pages 8 and 9). Apparently, Houston et al. concerns the selection of "antigen peptides" that bind to targeted antibodies, rather than the construction and selection of target antibodies. Focusing on an entirely different purpose, Houston et al. does not describe or even suggest the use of coiled-coil sequences to generate stable antigen-binding units.

Thus, there remains a considerable need for improved compositions and methods to generate stable antigen-binding units and repertoires thereof to effect identification of therapeutic antigen-binding units. An ideal antigen-binding unit would be more stable than a Fv fragment, but would preferably be smaller than a Fab fragment to allow large-scale production and efficient display. Such antigen-binding unit would also serve as a building block for constructing multivalent and/or multispecific antibodies. The present invention satisfies these needs and provides related advantages as well.

SUMMARY OF THE INVENTION

A principal aspect of the present invention is the design of a technique for specific assembly of monomeric polypeptides to form a stable heteromultimer. This technique of heteromultimer production facilitates high throughput production of functional heteromultimers and avoids the assembly of undesired homodimers. The method is particularly useful for generating a genetically diverse repertoire of heteromultimers such as antigen-binding units. The technique can readily be adapted to a variety of "genetic package display" technologies that facilitate the selection of antigen-binding units possessing the desired binding specificities. Such genetic package display technologies are detailed in U.S. Pat. Nos. 6,248,516, 5,969,108, 5,885,793, 5,837,500, 5,571,698, 5,223,409, 5,514,548, WO9005144, EP0368684, WO09201047, WO09311236, and WO09708320.

The subject antigen-binding unit is assembled and stabilized by the pairwise affinity of a distinct pair of heterodimerization sequences. The sequences are distinct in that at least one member of the heterodimerization pair is essentially incapable of forming homodimers under physiological buffer conditions and/or at physiological body temperatures. In certain embodiments, the stabilized antigen-binding unit not only has a molecular size smaller than a Fab fragment, but also exhibits the required binding specificity and affinity. Moreover, certain non-single-chain antigen-binding units of the present invention bear higher binding affinities than the corresponding conventional single-chain antibodies (scFv). The antigen-binding unit is particularly suited for antibody library construction and display. Certain configurations of the subject antigen-binding unit serve as convenient building units for multivalent and multispecific immunoglobulins.

Specifically, the present invention provides a non-single-chain antigen-binding unit comprising: (a) a light (L) chain polypeptide comprising a light (L) chain variable region fused to a first heterodimerization sequence; (b) a heavy (H) chain polypeptide comprising a heavy (H) chain variable region fused to a second heterodimerization sequence; wherein the L chain and the H chain polypeptides dimerize via pairwise affinity of the first and second heterodimerization sequences; and wherein at least one of the heterodimerization sequences is essentially incapable of forming a homodimer under physiological buffer conditions and/or at physiological body temperatures. Preferably, both of the first and second heterodimerization sequences are essentially incapable of forming homodimers under physiological buffer conditions and at physiological body temperatures.

In another aspect, the present invention provides a non-single-chain antigen-binding unit comprising: (a) a light (L) chain polypeptide comprising a light (L) chain variable region fused to a first heterodimerization sequence; (b) a heavy (H) chain polypeptide comprising a heavy (H) chain variable region fused to a second heterodimerization sequence; wherein the L chain and the H chain polypeptides dimerize via pairwise affinity of the first and second heterodimerization sequences which are derived from heterodimeric receptors. In one aspect, the first and second heterodimerization sequences comprising heterodimerization receptor sequences that mediate heterodimerization of the receptors. In yet another aspect, the subject heterodimerization sequences form a coiled-coil dimer. In still another aspect, the L and the H chain polypeptides dimerize via non-covalent pairwise affinity of the two heterodimerization sequences. Preferably, the L or the H chain polypeptide further comprises a flexon that is flanked by the variable region and the heterodimerization sequence. Both the L and H polypeptide sequences may be derived from human L and H chains. To further stabilize the heterodimeric Abus, cysteine residues can be introduced to provide disulfide bonds between the first and the second heterodimerization sequences. The non-single-chain antigen-binding units may be monovalent or multivalent. They may be monospecific or multispecific. Preferred multispecific Abus are bispecific, trispecific and tetraspecific molecules.

In a separate embodiment, the present invention provides a single-chain antigen-binding unit comprising a light (L) chain variable region and a heavy (H) chain variable region connected by a first and a second heterodimerization sequence spanning the distance between the C-terminus of one of the region to the N-terminus of the other region, wherein the two regions form an intra-molecular dimer via pairwise affinity of the first and second heterodimerization sequences; and wherein at least one of the heterodimerization sequences is essentially incapable of forming a homodimer under physiological buffer conditions and/or at physiological body temperatures. Preferably, both of the first and second heterodimerization sequences are essentially incapable of forming homodimers under physiological buffer conditions and at physiological body temperatures.

In another aspect, the present invention provides a single-chain antigen-binding unit, wherein the VL and VH regions form an intra-molecular dimer via pairwise affinity of the first and second heterodimerization sequences which are derived from heterodimeric receptors. In one aspect, the first and second heterodimerization sequences comprising heterodimerization receptor sequences that mediate heterodimerization of the receptors.

In yet another aspect, first and second heterodimerization sequences form a coiled-coil dimer. In another aspect, the first and second heterodimerization sequences dimerize via non-covalent pairwise affinity. Both the VL and VH regions can be derived from the corresponding sequences in a human L and H chains, respectively.

Both the non-single-chain and single-chain antigen-binding units can be conjugated to a chemically functional moiety. Exemplary functional moieties include but are not limited to signal peptides, agents that enhance immunologic reactivity, agents that facilitate coupling to a solid support, vaccine carriers, bioresponse modifiers, toxins, detectable labels, paramagnetic labels, and drugs.

Preferred heterodimerization sequences contained in the subject antigen-binding units are derived from C-terminal sequences of $GABA_B$ receptor 1 and $GABA_B$ receptor 2, respectively. More preferably, the first heterodimerization sequence is linked to a cysteine residue, said first heterodimerization comprising $GABA_B$ receptor 1 polypeptide of at least 30 amino acid residues that is essentially identical to a linear peptide sequence of comparable length depicted in SEQ ID NO. 2; and the second heterodimerization sequence is linked to a cysteine residue, said second heterodimerization comprising $GABA_B$ receptor 2 polypeptide of at least 30 amino acid residues that is essentially identical to a linear peptide sequence of comparable length depicted in SEQ ID NO. 4. Alternatively, the first heterodimerization sequence is linked to a cysteine residue, said first heterodimerization comprising a $GABA_B$ receptor 2 polypeptide of at least 30 amino acid residues that is essentially identical to a linear peptide sequence of comparable length depicted in SEQ ID NO. 4; and the second heterodimerization sequence is linked to a cysteine residue, said second heterodimerization comprising a $GABA_B$ receptor 1 polypeptide of at least 30 amino acid residues that is essentially identical to a linear peptide sequence of comparable length depicted in SEQ ID NO. 2.

The present invention provides a recombinant polynucleotide comprising a coding sequence that encodes the L and/or H polypeptide of a non-single-chain antigen-binding unit. The invention also provides a recombinant polynucleotide comprising a coding sequence that encodes the VL or VH regions of a single-chain antigen-binding unit. Also provided is a vector comprising any one of the recombinant polynucleotides described herein. The vector can be an expression vector, e.g. a phage display vector. Further provided in this invention is a selectable library of expression vectors encoding a repertoire of antigen binding units, comprising more than one subject vector. Preferably, the selectable library comprises a plurality of phage display vectors.

The present invention also provides a host cell comprising the subject recombinant polynucleotides. The recombinant polynucleotide encoding the L chain polypeptide and the polynucleotide encoding the H chain polypeptide may be present in a single vector or in separate vectors. The host cell may be eukaryotic or prokaryotic.

In yet another embodiment, the present invention provides a method of producing a non-single-chain antigen-binding unit. The method involves the following steps: (a) expressing in a host cell a first recombinant polynucleotide encoding a light (L) chain polypeptide comprising a light (L) chain variable region fused to a first heterodimerization sequence, and a second recombinant polynucleotide encoding a heavy (H) chain polypeptide comprising a heavy (H) chain variable region fused to a second heterodimerization sequence; wherein the L chain and the H chain polypeptides dimerize via pairwise affinity of the first and second heterodimerization sequences; and wherein at least one of the heterodimerization sequences is essentially incapable of forming a homodimer under physiological buffer conditions and/or at physiological body temperatures; and optionally (b) isolating the antigen-binding unit expressed in the host cell.

The produced antigen-binding unit may also contain heterodimerization sequences that are derived from heterodimeric receptors. Additionally, the non-single-chain antigen-binding expressed in step (a) can be displayed on surface of the host cell. Preferably, the non-single-chain antigen-binding expressed in step (a) is displayed on a phage particle.

In still another embodiment, the present invention provides a method of producing a non-single-chain antigen-binding unit, the method comprises the steps of (a) preparing a first recombinant polynucleotide encoding a light (L) chain polypeptide comprising a light (L) chain variable region fused to a first heterodimerization sequence, and a second recombinant polynucleotide encoding a heavy (H) chain polypeptide comprising a heavy (H) chain variable region fused to a second heterodimerization sequence; wherein the L chain and the H chain polypeptides dimerize via pairwise affinity of the first and second heterodimerization sequences; and wherein at least one of the heterodimerization sequences is essentially incapable of forming a homodimer under physiological buffer conditions and/or at physiological body temperatures; and (b) allowing the first and second polypeptides to dimerize via pairwise affinity of the first and second heterodimerization sequences. The step of dimerization may take place in vitro or in vivo.

This invention also includes a method of producing a single-chain antigen-binding unit. The methods involves the steps of (a) expressing in a host cell a polynucleotide comprising a coding sequence that encodes the subject single-chain antigen-binding unit; and optionally (b) isolating the single-chain antigen-binding unit expressed in the host cell.

This invention further includes a method of displaying a chimeric heteromultimer comprising at least two polypeptides on a surface of a host cell. This method comprises expressing in the host cell (i) a first recombinant polynucleotide encoding a first polypeptide fused to a first heterodimerization sequence and a surface presenting sequence; (ii) a second recombinant polynucleotide encoding a second polypeptide fused to a second heterodimerization sequence; wherein the first and second polypeptides dimerize via pairwise affinity of the first and second heterodimerization sequences; wherein at least one of the heterodimerization sequences is incapable of forming a homodimer under physiological buffer conditions and/or at physiological body temperatures. In one aspect, the first and second polynucleotides are expressed by a single phage display vector. In another aspect, the first and second polynucleotides are expressed by separate phage display vectors. The chimeric heteromultimer is preferably a non-single-chain antigen-binding unit of the present invention.

The invention also encompasses a method of identifying a non-single-chain antigen-binding unit that is immunoreactive with a desired antigen. The method comprises the steps of: (a) preparing a genetically diverse repertoire of antigen-binding units, wherein the repertoire comprises more than one subject antigen-binding unit; (b) contacting the repertoire of antigen binding units with the desired antigen; and (c) detecting a specific binding between antigen binding units and the antigen, thereby identifying the antigen-binding unit that is immunoreactive with the desired antigen. In one aspect of this embodiment, the repertoire of antigen-binding units is prepared by expressing a library of vectors encoding a plurality of the antigen-binding units. Preferably, the library of vectors comprises a plurality of phage vectors.

Finally, the present invention provides a kit comprising a vector of this invention in suitable packaging.

EXPLANATION OF ABBREVIATIONS USED HEREIN

1. Nsc: Non-single chain
2. Sc: Sing-chain
3. Abu: Antigen-binding unit
4. Abus: Antigen-binding units
4. L chain: Light chain
5. H chain: Heavy chain
6. VL: Light chain variable region
7. VH: Heavy chain variable region

BRIEF DESCRIPTION OF THE DRAWINGS

FIG. 2 depicts the nucleotide and amino acid sequences of $GABA_B$ receptor 1 and 2 that were used in constructing the subject Abus. The coiled-coil sequences are derived from human $GABA_B$-R1 and $GABA_B$-R2 receptors. The coding amino acid sequences from $GABA_B$ receptor 1 begins with EEKS (residues 7-10 of SEQ ID NO. 2) and ends with QLQS (residues 37-40 of SEQ ID NO. 2) as shown in the top panel of FIG. 2. The coding amino acid sequences from $GABA_B$ receptor 2 begins with TSRL (residues 7-10 of SEQ ID NO. 4) and ends with QLQD (residues 37-40 of SEQ ID NO. 4) as shown in the bottom panel of FIG. 2. A flexible—SerArgGlyGlyGlyGly (SEQ ID NO. 31) spacer was added to the amino-termini of R1 and R2 heterodimerization sequences to favor the formation of functional Fv heterodimer. To further stabilize the heterodimer, we have introduced a ValGlyGlyCys (SEQ ID NO. 29) spacer to lock the heterodimeric coiled-coil pair via the disulfide bond between the cysteine residues SEQ ID NOS. 2 and 4. The SerArg coding sequences at the N-terminus of the GGGG (SEQ ID NO. 30) spacer provides XbaI or XhoI sites for fusion of the GR1 (heterodimerization sequence derived from $GABA_B1$ receptor) and GR2 (heterodimerization sequence derived from $GABA_B2$) domains to the carboxyl-termini of VH and VL fragments, respectively.

FIG. 3B provides the nucleotide sequence and coding sequence after the lac promoter for pABMX1 (SEQ ID NOS. 5-6, respectively) and pABMX2 (SEQ ID NOS. 7-8, respectively). The HindIII/XbaI or HindIII/NotI or XbaI/NotI sites can be used for inserting heterologous sequences that are to be expressed in pABMX1 vector. Additional cloning sites included in the pABMX2 vector are NcoI, PstI, XbaI and NotI.

FIG. 4B provides the nucleotide sequence and coding sequence after the lac promoter pABMD1 (SEQ ID NOS. 9-10, respectively) and pABMD2 (SEQ ID NOS. 11-12, respectively).

FIG. 5B provides the nucleotide and coding sequence between the leader sequence and DH-tag in pABMX5 (SEQ ID NOS. 13-14, respectively) and pABMX6 (SEQ ID NOS. 15-16, respectively) vectors. In addition, the ribosome-binding site, DH-tag, subcloning sites for insertion of VH, VL, GR1 and GR2, are also indicated.

FIG. 6B provides the nucleotide and coding sequence between the leader sequence and pIII for pABMD5 (SEQ ID NOS. 17-18, respectively) and pABMD6 (SEQ ID NOS. 19-20, respectively) vectors. In addition, ribosome binding site, DH-tag, partial pIII, subcloning sites for insertion of VH, VL, GR1 and GR2, are also indicated.

FIG. 7 depicts the vector pAMEX7 useful for expressing ccFv fragment in yeast.

FIG. 11B depicts a comparison of the antigen binding capability of AM2-ccFv expressing phage and that of AM2-scFv expressing phage. The results indicate that the binding capability of the phage particles displaying the AM2-ccFv fragments is about one order of magnitude higher than that of the AM2-scFv expressing phages.

FIG. 15 depicts four bispecific Abu configurations, each comprising one or more basic ccFv unit with distinct binding specificities, and/or a scFv or dsFv fragment.

MODE(S) FOR CARRYING OUT THE INVENTION

Figure 1:
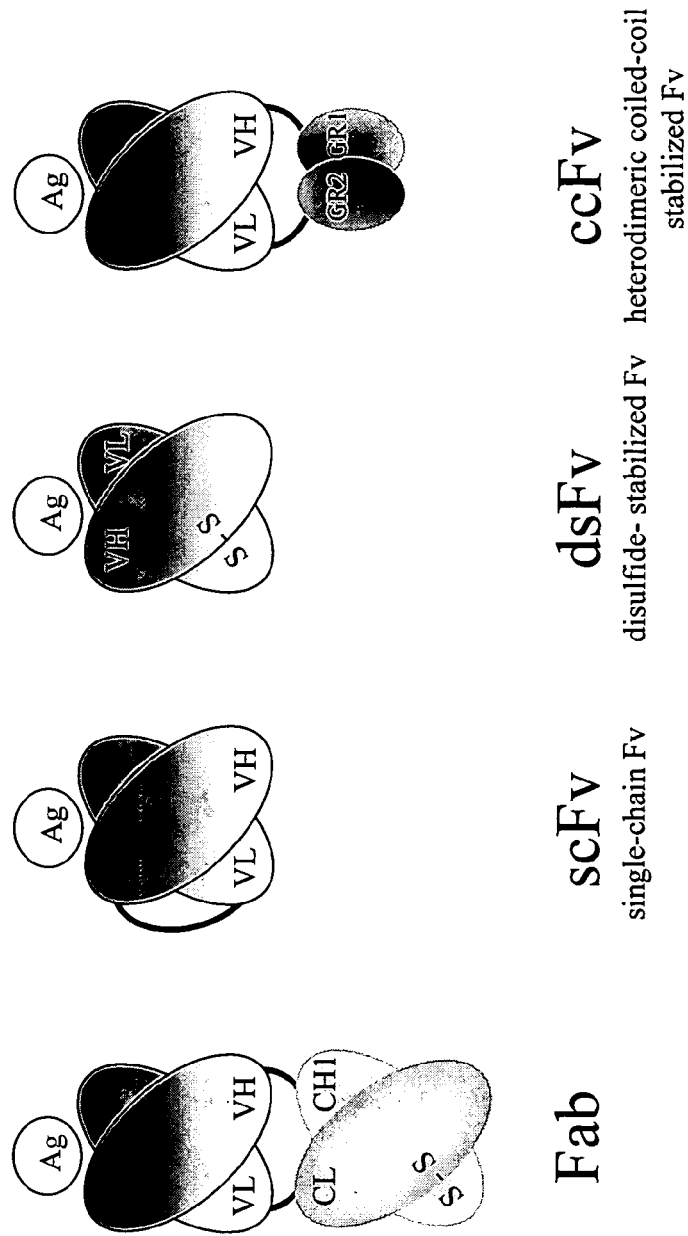
FIG. 1 is a schematic representation depicting various antigen-binding units.
Figure 3A:
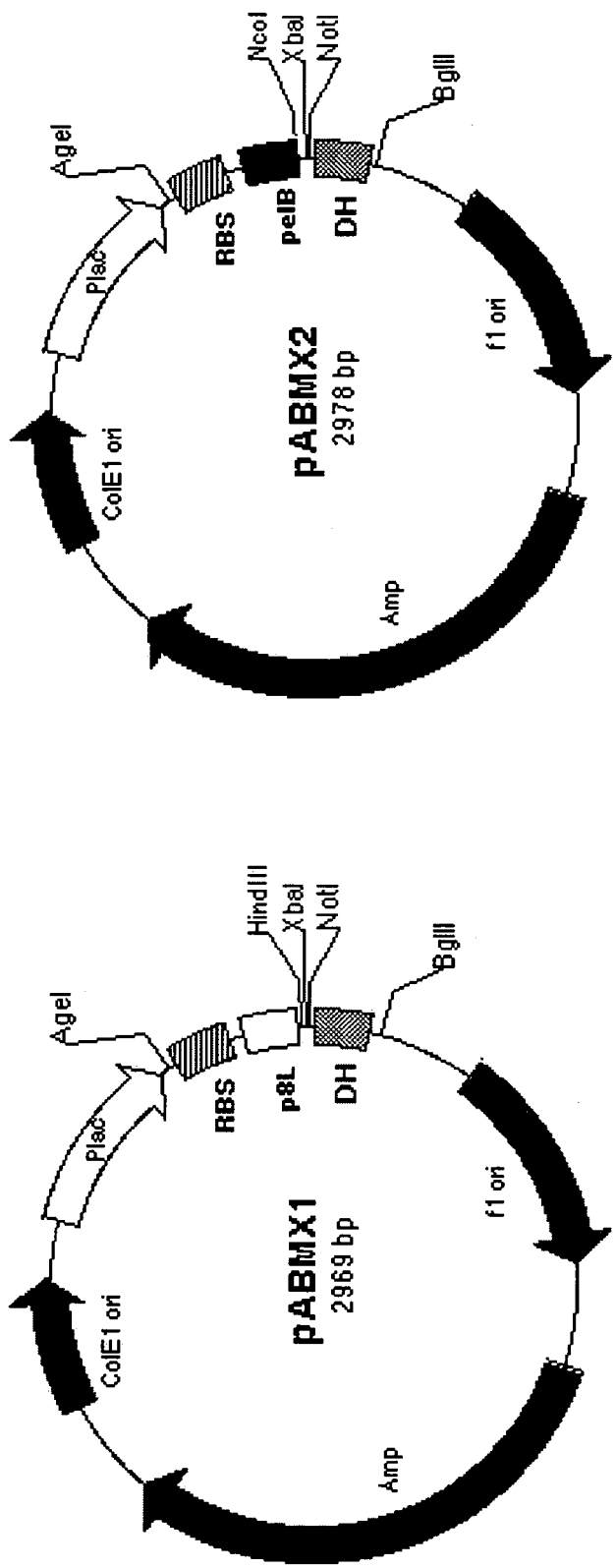
FIG. 3A is a schematic representation of two expression vectors pABMX1 and pABMX2. Both pABMX1 and pABMX2 were derived from pbluescript SK(+) comprising an ampicillin-resistance gene (Amp) for antibiotic selection, a plasmid origin of replication (cole1 ori), a f1 phage origin of replication (f1 ori), and lac promoter/lac O1 driven protein expression cassette (plac-RBS-p8Leader-DH tag for pABMX1, plac-RBS-pe1B Leader-DH tag for pABMX2). The heterologous sequence is expressed as a DH-tag (HA and 6×His tag) fusion protein, and is directed by the signal peptide either p8 leader or pe1B leader into periplasmid space, where the leader sequence is cleaved.

Throughout this disclosure, various publications, patents and published patent specifications are referenced by an identifying citation. The disclosures of these publications, patents and published patent specifications are hereby incorporated by reference into the present disclosure.

General Techniques:

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Matthews, PLANT VIROLOGY, $3^{rd}$ edition (1991); Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

Definitions:

The terms "polypeptide", "peptide" and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A polypeptide or amino acid sequence "derived from" a designated protein refers to the origin of the polypeptide. Preferably, the polypeptide have an amino acid sequence that is essentially identical to that of a polypeptide encoded in the sequence, or a portion thereof wherein the portion consists of at least 10-20 amino acids, preferably at least 20-30 amino acids, more preferably at least 30-50 amino acids, or which is immunologically identifiable with a polypeptide encoded in the sequence. This terminology also includes a polypeptide expressed from a designated nucleic acid sequence.

A "chimeric" protein contains at least one fusion polypeptide comprising regions in a different position in the sequence than that occurs in nature. The regions may normally exist in separate proteins and are brought together in the fusion polypeptide; or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship.

A "multimeric protein" as used herein refers to a globular protein containing more than one separate polypeptide or protein chain associated with each other to form a single globular protein in vitro or in vivo. The multimeric protein may consist of more than one polypeptide of the same kind to form a "homomultimer." Alternatively, the multimeric protein may also be composed of more than one polypeptide of distinct sequences to form a "heteromultimer." Thus, a "heteromultimer" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where more than two polypeptides are present. Exemplary structures for the heteromultimer include heterodimers (e.g. Fv and Fab fragments, diabodies, $GABA_B$ receptors 1 and 2 complexes), trimeric G-proteins, heterotetramers (e.g. $F(ab')_2$ fragments) and further oligomeric structures.

The "first recombinant polypeptide" of a chimeric heteromultimer refers to any polypeptide which is or was associated with a "second recombinant polypeptide" via the pairwise affinity of two dimerization sequences that are linked to the first and second polypeptides, respectively. Preferably, the first and second polypeptides contain sequences derived from a light or a heavy chain of an immunoglobulin. More preferably, the first and second polypeptides form a Nsc Abu that confers binding specificity to a desired antigen.

A "first heterodimerization sequence" refers to any dimerization sequence which is or was associated with a "second heterodimerization sequence," wherein the second heterodimerization sequence differs in amino acid sequence by at least one amino acid residue. A "heterodimerization pair" refers to two heterodimerization sequences capable of forming a heterodimer.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains interconnected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units" ("Abus"). Abus can be broadly divided into "single-chain" ("Sc") and "non-single-chain" ("Nsc") types based on their molecular structures.

Also encompassed within the terms "antibodies" and "Abus" are immunoglobulin molecules of a variety of species origins including invertebrates and vertebrates. The term "human" as applies to an antibody or an Abu refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

"Non-single-chain antigen-binding unit" ("Nsc Abus") are heteromultimers comprising a light-chain polypeptide and a heavy-chain polypeptide. Examples of the Nsc Abus include but are not limited to (i) a ccFv fragment (FIG. 1) stabilized by the heterodimerization sequences disclosed herein; (ii) any other monovalent and multivalent molecules comprising at least one ccFv fragment as described herein; (iii) an Fab fragment consisting of the VL, VH, CL and CH1 domains; (iv) an Fd fragment consisting of the VH and CH1 domains; (v) an Fv fragment consisting of the VL and VH domains of a single arm of an antibody; (vi) an F(ab')2 fragment, a bivalent fragment comprising two Fab fragments linked by a disulfide bridge at the hinge region; (vii) a diabody; and (viii) any other Nsc Abus that are described in Little et al. (2000) Immunology Today.

As noted above, a Nsc Abus can be either "monovalent" or "multivalent." Whereas the former has one binding site per antigen-binding unit, the latter contains multiple binding sites capable of binding to more than one antigen of the same or different kind. Depending on the number of binding sites, a Nsc Abus may be bivalent (having two antigen-binding sites), trivalent (having three antigen-binding sites), tetravalent (having four antigen-binding sites), and so on.

Figure 16:
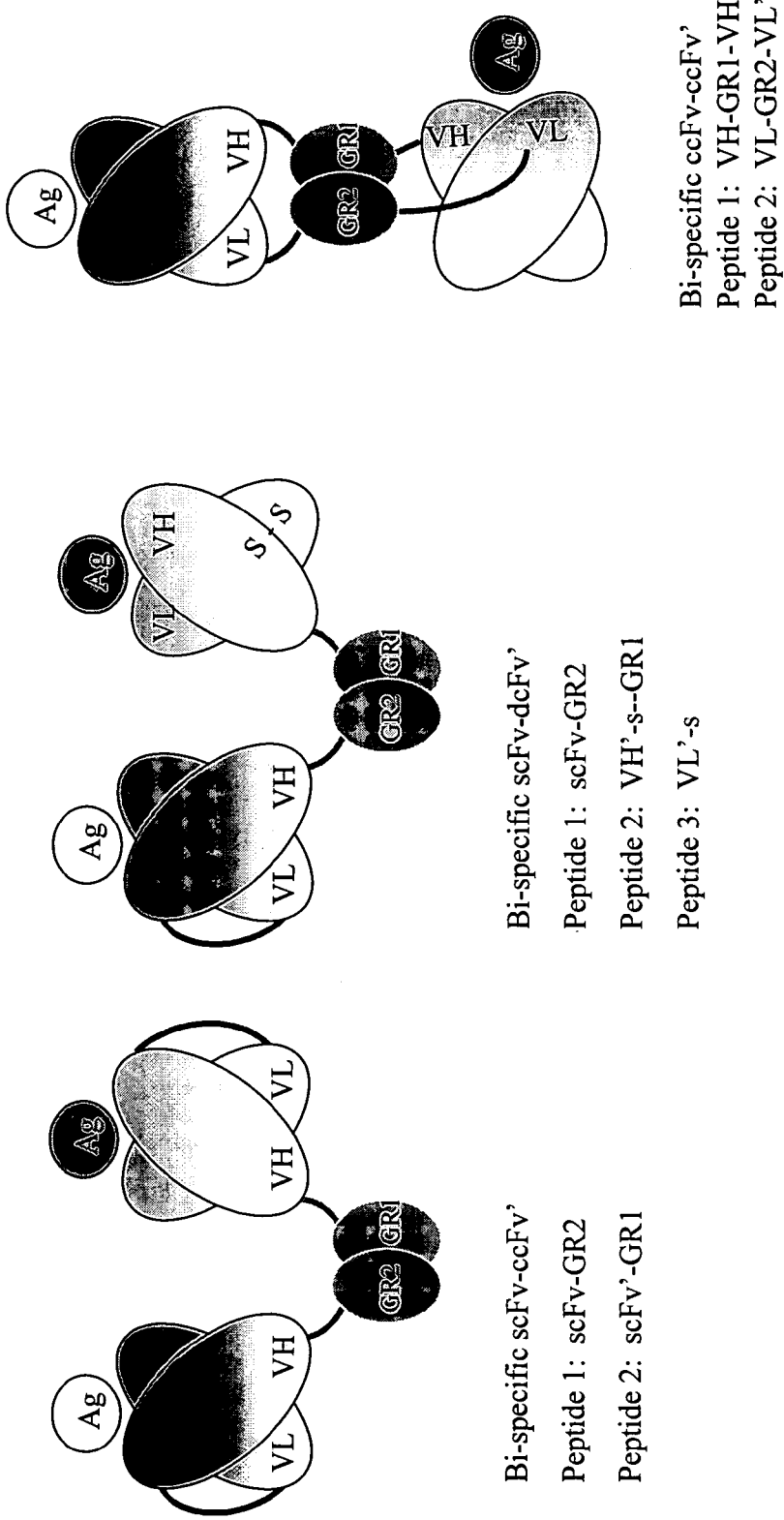
FIG. 16 depicts three additional bispecific Abu configurations.
Figure 17:
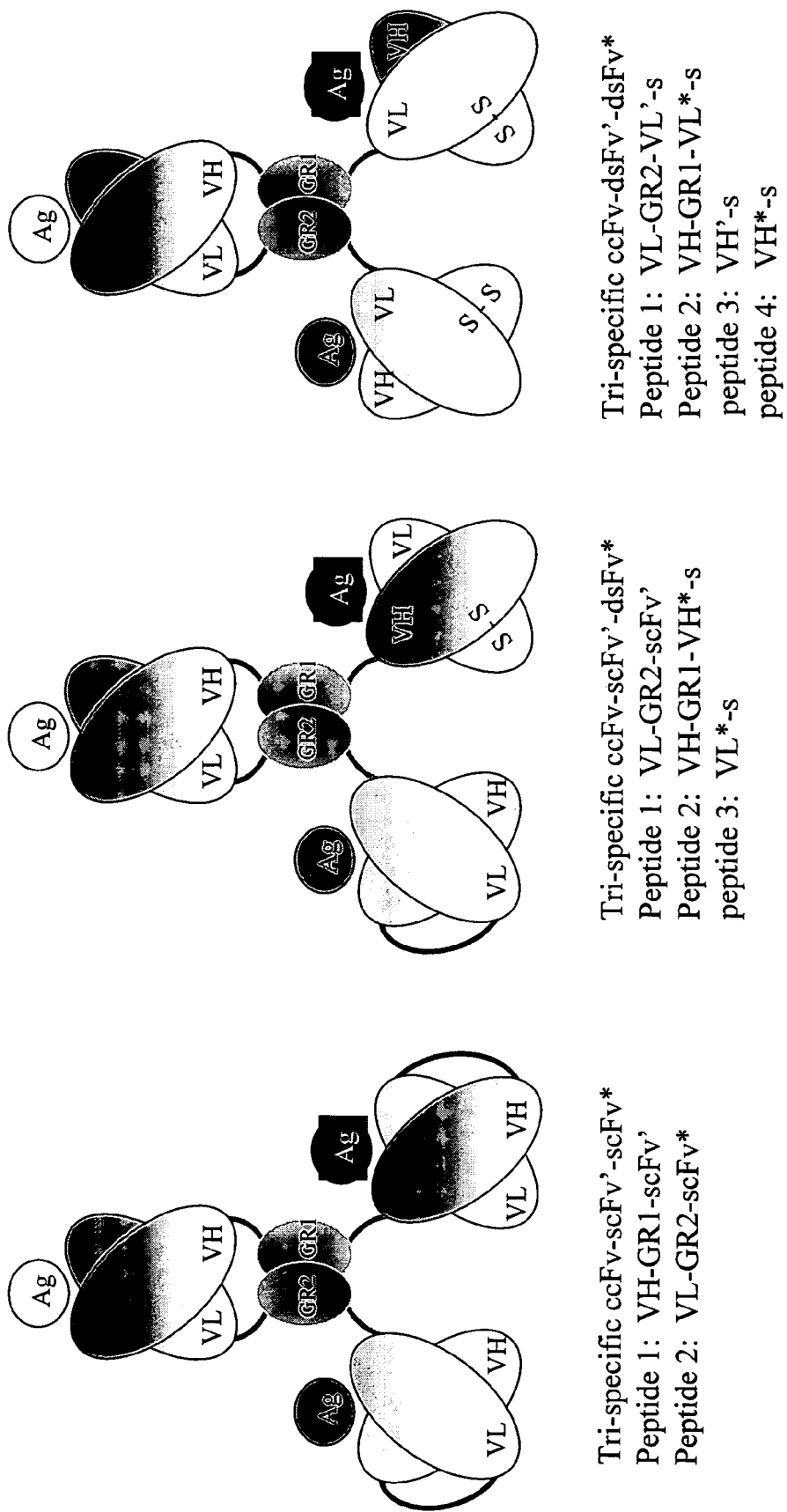
FIG. 17 depicts three trispecific Abu configurations, each comprising at least one basic ccFv unit, and at least one scFv or dsFv fragment.

Multivalent Nsc Abus can be further classified on the basis of their binding specificities. A "monospecific" Nsc Abu is a molecule capable of binding to one or more antigens of the same kind. A "multispecific" Nsc Abu is a molecule having binding specificities for at least two different antigens. While such molecules normally will only bind two distinct antigens (i.e. bispecific Abus), antibodies with additional specificities such as trispecific antibodies are encompassed by this expression when used herein (see, e.g. FIGS. 15-17). Examples of bispecific antigen binding units include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; bispecific Abus with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); bispecific Abus which can be used as fibrinolytic agents such as anti-fibrin/anti-tissue plasminogen activator (tPA), anti-fibrin/anti-urokinase-type plasminogen activator (uPA); bispecific antigen-binding untis for targeting immune complexes to cell surface receptors such as anti-low density lipoprotein (LDL)/anti-Fc receptor (e.g. Fcγ RI, FcγRII or FcγRIII); bispecific Abus for use in therapy of infectious diseases such as anti-CD3/anti-herpes simplex virus (HSV), anti-T-cell receptor:CD3 complex/anti-influenza, anti-FcγR/anti-HIV; bispecific Abus for tumor detection in vitro or in vivo such as anti-CEA/anti-EOTUBE, anti-CEA/anti-DPTA, anti-p185$^{HER2}$/anti-hapten; BsAbs as vaccine adjuvants (see Fanger et al., supra); and bispecific Abus as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-.beta.-galactosidase (see Nolan et al., supra). Examples of trispecific antibodies include anti-CD3/anti-CD4/anti-CD37, anti-CD3/anti-CD5/anti-CD37 and anti-CD3/anti-CD8/anti-CD37.

Figure 18:
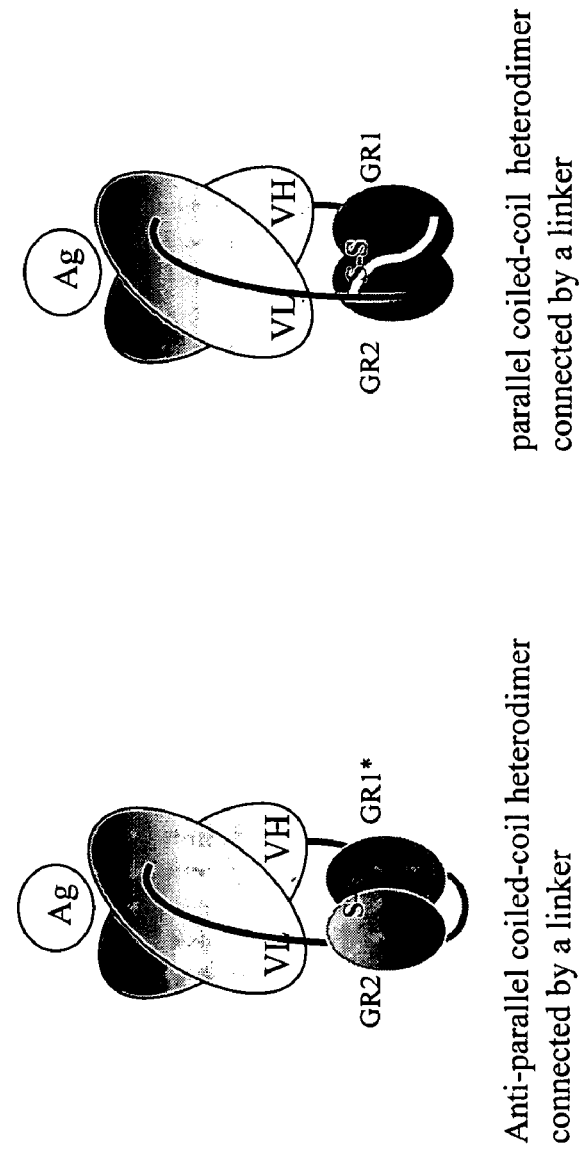
FIG. 18 depicts two exemplary single Abus, in which the heterodimerization sequences are arranged in either a parallel or anti-parallel configuration.
Figure 19:
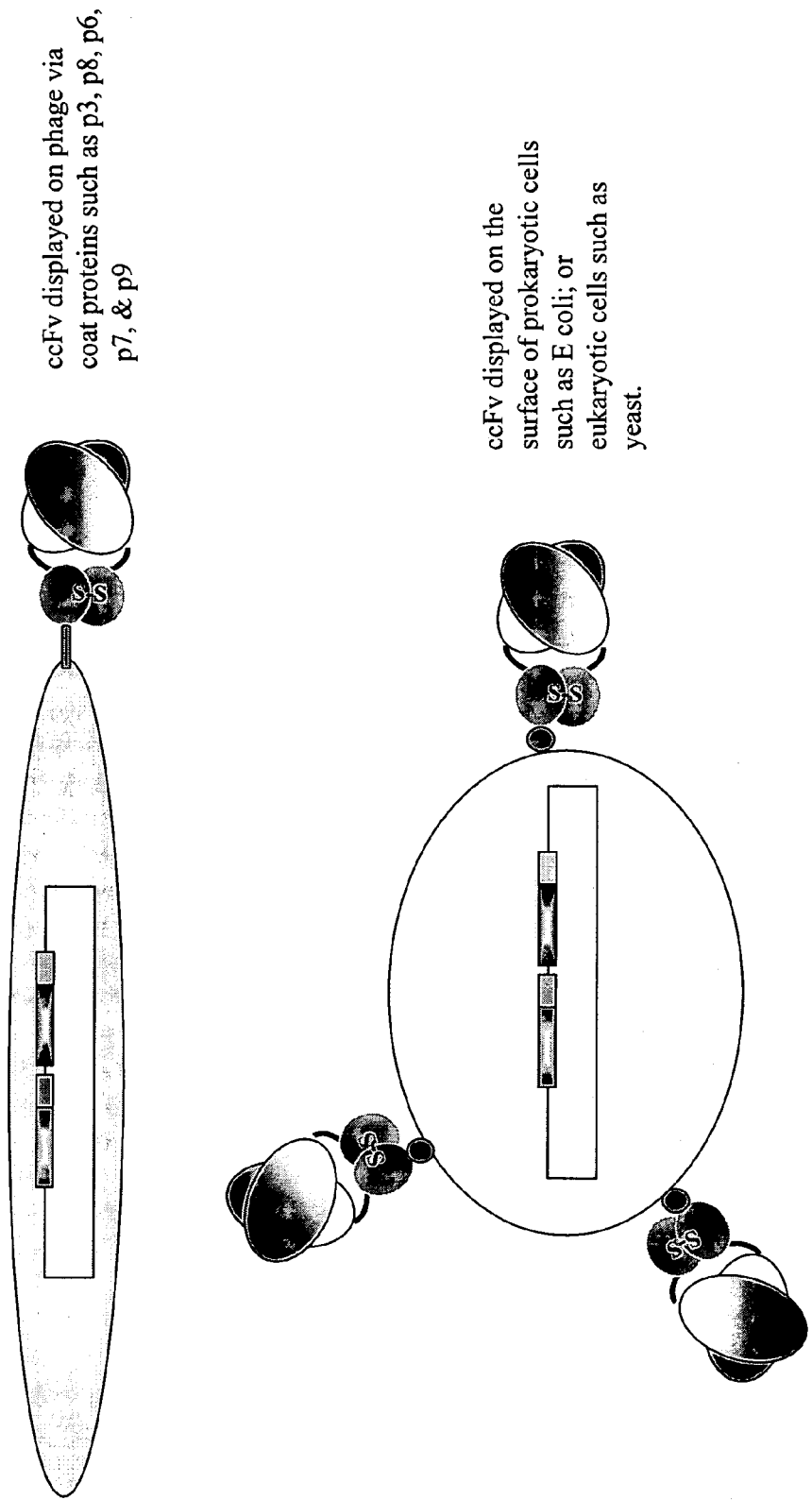
FIG. 19 is a schematic representation of ccFv displayed on the surface of a prokaryotic or eukaryotic cell. The top panel depicts ccFv displayed by a phage particle that is adhered to the surface of a host cell.

"Single-chain antigen-binding unit" ("Sc Abu") refers to a monomeric Abu. Although the two domains of the Fv fragment are coded for by separate genes, a synthetic linker can be made that enables them to be made as a single protein chain (i.e. single chain Fv ("scFv") as described in Bird et al. (1998) *Science* 242:423-426 and Huston et al. 1988) *PNAS* 85:5879-5883) BY RECOMBINANT METHODS. Other Sc Abus include antigen-binding molecules stabilized by the subject heterodimerization sequences (see e.g. FIG. 18), and dAb fragments (Ward et al., (1989) *Nature* 341:544-546) which consist of a VH domain and an isolated complimentarity determining region (CDR). An example of a linking peptide is $(GGGGS)_3$ (SEQ ID NO. 32), which bridges approximately 3.5 nm between the carboxyl terminus of one V region and the amino terminus of another V region. Other linker sequences can also be used, and can provide additional functions, such as a means for attaching a drug or a solid support. A preferred single-chain antigen-binding unit contains VL and VH regions that are linked together and stabilized by a pair of subject heterodimerization sequences. The scFvs can be assembled in any order, for example, VH-(first heterodimerization sequence)-(second heterodimerization sequence)-VL, or VL-(first heterodimerization sequence)-(second heterodimerization sequence)-VH.

A "repertoire of antigen-binding units" refers to a plurality of antigen-binding units, at least two of which exhibit distinct binding specificities. A genetically diverse repertoire of antigen-binding units refers to a plurality of antigen-binding units, the majority and if not all of the antigen-binding units exhibit unique binding specificities with respect to each other. Genetically diverse repertoire typically has a complexity of at least $10^6$ to $10^3$, preferably between $10^7$ to $10^9$, more preferably between $10^8$ to $10^{10}$, even more preferably between $10^8$ to $10^{11}$ distinct antigen-binding units.

An antibody or Abu "specifically binds to" or "immunoreactive with" an antigen if it binds with greater affinity or avidity than it binds to other reference antigens including polypeptides or other substances.

An Abu is displayed "on the surface of a host cell" when the Abu is presented at the outer surface of a host cell. The displayed Abu may be directly attached to the outer surface of the host cell, or may be indirectly attached to the host cell via a host cell bound genetic package such as phage particle.

"Surface presenting sequences" refers to sequences that facilitate display of heterologous sequences. Typically, the surface presenting sequences are present on the outer surface of a genetic package, e.g. phage or bacteria. Preferred surface presenting sequences of phage is pIII of M13 filamentous phage.

"Antigen" as used herein means a substance that is recognized and bound specifically by an antibody. Antigens can include peptides, proteins, glycoproteins, polysaccharides and lipids; portions thereof and combinations thereof.

As used herein, the term "surface antigens" refers to the plasma membrane components of a cell. It encompasses integral and peripheral membrane proteins, glycoproteins, polysaccharides and lipids that constitute the plasma membrane. An "integral membrane protein" is a transmembrane protein that extends across the lipid bilayer of the plasma membrane of a cell. A typical integral membrane protein consists of at least one "membrane spanning segment" that generally comprises hydrophobic amino acid residues. Peripheral membrane proteins do not extend into the hydrophobic interior of the lipid bilayer and they are bound to the membrane surface by noncovalent interaction with other membrane proteins.

The terms "membrane", "cytosolic", "nuclear" and "secreted" as applied to cellular proteins specify the extracellular and/or subcellular location in which the cellular protein is mostly, predominantly, or preferentially localized.

"Cell surface receptors" represent a subset of membrane proteins, capable of binding to their respective ligands. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions.

A "heterodimeric receptor" encompasses cellular proteins composed of two proteinaceous subunits which exhibits binding affinity to a ligand. The two proteinaceous subunits are distinct molecules which differ in amino acid sequence by at least one amino acid residue. Non-limiting illustrative heterodimeric receptors are those that bind to growth factors (e.g. heregulin), neurotransmitters (e.g. γ-Aminobutyric acid), and other organic or inorganic small molecules (e.g. mineralocorticoid, glucocorticoid). Preferred heterodimeric receptors are nuclear hormone receptors (Belshaw et al. (1996) *Proc. Natl. Acad. Sci. U.S. A* 93(10):4604-4607), erbB3 and erbB2 receptor complex, and G-protein-coupled receptors including but not limited to opioid (Gomes et al. (2000) *J Neuroscience* 20(22): RC110); Jordan et al. (1999) *Nature* 399:697-700), muscarinic, dopamine, serotonin, adenosine/dopamine, and $GABA_B$ families of receptors.

"Domain" refers to a portion of a protein that is physically or functionally distinguished from other portions of the protein or peptide. Physically-defined domains include those amino acid sequences that are exceptionally hydrophobic or hydrophilic, such as those sequences that are membrane-associated or cytoplasm-associated. Domains may also be defined by internal homologies that arise, for example, from gene duplication. Functionally-defined domains have a distinct biological function(s). The ligand-binding domain of a receptor, for example, is that domain that binds ligand. An antigen-binding domain refers to the part of an antigen-binding unit or an antibody that binds to the antigen. Functionally-defined domains need not be encoded by contiguous amino acid sequences. Functionally-defined domains may contain one or more physically-defined domain. Receptors, for example, are generally divided into the extracellular ligand-binding domain, a transmembrane domain, and an intracellular effector domain. A "membrane anchorage domain" refers to the portion of a protein that mediates membrane association. Generally, the membrane anchorage domain is composed of hydrophobic amino acid residues. Alternatively, the membrane anchorage domain may contain modified amino acids, e.g. amino acids that are attached to a fatty acid chain, which in turn anchors the protein to a membrane.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

A "defined medium" refers to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cysteine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolari range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

As used herein, the term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring the polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart.

Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

"Linked" and "fused" or "fusion" are used interchangeably herein. These terms refer to the joining together of two more chemical elements or components, by whatever means including chemical conjugation or recombinant means. An "in-frame fusion" refers to the joining of two or more open reading frames (OFRS) to form a continuous longer OFR, in a manner that maintains the correct reading frame of the original OFRs. Thus, the resulting recombinant fusion protein is a single protein containing two ore more segments that correspond to polypeptides encoded by the original OFRs (which segments are not normally so joined in nature.) Although the reading frame is thus made continuous throughout the fused segments, the segments may be physically or spatially separated by, for example, in-frame linker sequence (e.g. "flexon"), as described infra.

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide which is known to comprise additional residues in one or both directions.

"Heterologous" means derived from a genotypically distinct entity from the rest of the entity to which it is being compared. For example, a promoter removed from its native coding sequence and operatively linked to a coding sequence other than the native sequence is a heterologous promoter. The term "heterologous" as applied to a polynucleotide, a polypeptide, means that the polynucleotide or polypeptide is derived from a genotypically distinct entity from that of the rest of the entity to which it is being compared. For instance, a heterologous polynucleotide or antigen may be derived from a different species origin, different cell type, and the same type of cell of distinct individuals.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Recombinant" as applied to a polynucleotide means that the polynucleotide is the product of various combinations of cloning, restriction and/or ligation steps, and other procedures that result in a construct that is distinct from a polynucleotide found in nature.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

A "fusion gene" is a gene composed of at least two heterologous polynucleotides that are linked together.

A gene "database" denotes a set of stored data which represent a collection of sequences including nucleotide and peptide sequences, which in turn represent a collection of biological reference materials.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product. If the polynucleotide is derived from genomic DNA, expression may include splicing of the mRNA in a eukaryotic cell.

A "subject" as used herein refers to a biological entity containing expressed genetic materials. The biological entity is preferably plant, animal, or microorganisms including bacteria, viruses, fungi, and protozoa. Tissues, cells and their progeny of a biological entity obtained in vivo or cultured in vitro are also encompassed.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions.

An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

A "replicon" refers to a polynucleotide comprising an origin of replication (generally referred to as an ori sequence) which allows for replication of the polynucleotide in an appropriate host cell. Examples of replicons include episomes (such as plasmids), as well as chromosomes (such as the nuclear or mitochondrial chromosomes).

Chimeric Heteromultimer of the Present Invention:

As noted above, proper assembly of polypeptide subunits to form a stable complex is required to ensure the biological function, of a multimeric protein. Accordingly, a central aspect of the present invention is the design of a technique that enables specific assembly of selected monomeric polypeptides to effect efficient production of heteromultimers. The experimental design is particularly useful for generating and screening for heteromultimers such as Abus whose binding specificities depend on the assembly of specific subunits in a specific manner. Distinguished from the previously reported chimeric Abus, the subject Abus have one or more of the following unique features. First, the Abus are reconstituted via pairwise affinity of two heterodimerization sequences, at least one of which and preferably both of which, lack(s) detectable propensity to form homodimers. Unlike the previously reported dimerization sequences such as Fos and Jun leucine zippers that are known to form homodimers under both physiological buffer conditions and physiological body temperature (O'Shea et al. (1992) *Cell* 68: 699-708; Vidal et al. (1996) *Proc. Natl. Acad. Sci. U.S.A*), the subject heterodimerization sequences are essentially incapable of forming homodimers either under the specified buffer conditions and/or at the specified body temperatures. The subject heterodimerization sequences may be also distinguished from the previously employed sequences at the structural level as detailed below.

In one embodiment, the present invention provides a chimeric heteromultimer displayed on the surface of the host cell, wherein heteromultimer comprises: (i) a first polypeptide fused to a first heterodimerization sequence and a surface presenting sequence; (ii) a second polypeptide fused to a second heterodimerization sequence; wherein the first and second polypeptides dimerize via pairwise affinity of the first and second heterodimerization sequences; wherein at least one of the heterodimerization sequences is essentially incapable of forming a homodimer under physiological buffer conditions and/or at physiological body temperatures.

In another embodiment, the present invention provides a Nsc Abu that comprises: (a) a light-chain polypeptide comprising a light-chain variable region linked to a first heterodimerization sequence; (b) a heavy-chain polypeptide comprising a heavy-chain variable region linked to a second heterodimerization sequence; wherein the light-chain and the heavy-chain polypeptides dimerize via pairwise affinity of the first and second heterodimerization sequences, at least one of which is essentially incapable of forming a homodimer under physiological buffer conditions and/or at physiological body temperatures. In another aspect, the present invention provides a Nsc Abu whose the light-chain and the heavy-chain polypeptides dimerize via pairwise affinity of the first and second heterodimerization sequences that are derived from heterodimeric receptors. In one aspect, the first and second heterodimerization sequences comprising heterodimerization receptor sequences that mediate heterodimerization of the receptors.

In a separate embodiment, the present invention provides a Sc Abu which comprises a light-chain variable region and a heavy-chain variable region connected by a first and a second heterodimerization sequence spanning the distance between the C-terminus of one of the region to the N-terminus of the other region, wherein the two regions form an intra-molecular dimer via pairwise affinity of the first and second heterodimerization sequences, at least one of which is essentially incapable of forming a homodimer under physiological buffer conditions and/or at physiological body temperatures. In another aspect of this embodiment, the present invention provides a Sc Abu wherein the light-chain variable region and the heavy-chain variable region form an intra-molecular dimer via pairwise affinity of two heterodimerization sequences that are derived from heterodimeric receptors. In one aspect, the first and second heterodimerization sequences comprising heterodimerization receptor sequences that mediate heterodimerization of the receptors.

Selection of Heterodimerization Sequences:

Several factors apply to the design of Abus having one or more of the above-mentioned characteristics. First, the heterodimerization sequences must exhibit pairwise affinity to effect formation of a stable complex. By "stable" is meant that the complex or dimer is sufficiently long-lasting to persist between the formation of the complex or dimer, and its subsequent detection and/or purification. The complex or dimer must be able to withstand whatever conditions exist or are introduced between the moment of formation and the moment of detection, these conditions being a function of the assay or reaction which is being performed. Preferably, the formation of the complex or dimer is carried out under physiological buffer conditions and at physiological body temperatures ranging from approximately room temperature to approximately 37° C. Intervening conditions which may optionally be present and which may dislodge a complex or dimer include washing, heating, adding additional solutes or solvents to the reaction mixture (such as denaturants), and competing with additional reacting species. Stable complex or dimer may be irreversible or reversible, but must meet the other requirements of this definition. Thus, a transient complex or dimer may form in a reaction mixture, but it does not constitute a stable complex if it dissociates spontaneously under physiological buffer conditions or as a result of a newly imposed condition or manipulation introduced before detection.

Second, the selected heterodimerization sequences must exhibit pairwise affinity resulting in predominant formation of heterodimers to a substantial exclusion of homodimers. Preferably, the predominant formation yields a heteromultimeric pool that contains at least 60% heterodimers, more preferably at least 80% heterodimers, more preferably between 85-90% heterodimers, and more preferably between 90-95% heterodimers, and even more preferably between 96-99% heterodimers that are allowed to form under physiological buffer conditions and/or physiological body temperatures. In certain embodiments of the present invention, at least one of the heterodimerization sequences employed to reconstitute an Abu is essentially incapable of forming a homodimer in a physiological buffer and/or at physiological body temperature. By "essentially incapable" is meant that the selected heterodimerization sequences when tested alone do not yield detectable amounts of homodimers in an in vitro sedimentation experiment as detailed in Kammerer et al. (1999) *Biochemistry* 38: 13263-13269), or in the in vivo two-hybrid yeast analysis (see e.g. White et al. *Nature* (1998) 396: 679-682). Specifically, Kammerer et al. have demonstrated by sedimentation experiments that the heterodimerization sequences of $GABA_B$ receptor 1 and 2, when tested alone, sediment at the molecular mass of the monomer under physiological conditions and at physiological body temperatures (e.g. at 37° C.). When mixed in equimolar amounts, $GABA_B$ receptor 1 and 2 heterodimerization sequences sediment at the molecular mass corresponding to the heterodimer of the two sequences (see Table 1 of Kammerer et al.). In addition, individual heterodimerization sequences can be expressed in a host cell and the absence of homodimers in the host cell can be demonstrated by a variety of protein analyses including but not limited to SDS-PAGE, Western blot, and immunoprecipitation. The in vitro assays must be conducted under a physiological buffer conditions, and/or preferably at physiological body temperatures. Generally, a physiological buffer contains a physiological concentration of salt and at adjusted to a neutral pH ranging from about 6.5 to about 7.8, and preferably from about 7.0 to about 7.5. A variety of physiological buffers is listed in Sambrook et al. (1989) supra and hence is not detailed herein. Preferred physiological conditions are described in Kammerer et al., supra.

The specific association of heterodimerization sequences typically involves noncovalent interactions. Such interactions encompass every exiting stable linkage that does not result in the formation of a covalent bond. Non-limiting examples of noncovalent interactions include electrostatic bonds, hydrogen bonding, Van der Waal's forces, steric interdigitation of amphiphilic peptides.

A further consideration in designing the subject Abu is to minimize any structural interference between the heterodimerization sequences and the antigen-binding site of the resulting heteromultimer. A variety of techniques is available in the art for designing a chimeric heteromultimer with minimal internal structural interference. For instance, one approach involves the use of minimal heterodimerization sequences containing only amino acid residues that are required for heterodimerization. The second approach is to link the heterodimerization sequences to either N-terminus or C-terminus of the resulting heteromultimer. The choice of either terminus will depend on the location of the biological active domain of the heteromultimer. For constructing a chimeric Abu whose antigen-binding site resides in the N-terminal half of the light and heavy chain variable regions, it is preferable to link the heterodimerization sequences to the C-terminus of a light or heavy chain. Another alternative design employs a "flexon" incorporated between the antigen-binding site and the heterodimerization sequence of the heteromultimer. "Flexon" as used herein, refers to a flexible polypeptide linker (or a nucleic acid sequence encoding such a polypeptide) which typically comprises amino acids having small side chains (e.g. glycine, alanine, valine, leucine, isoleucine, and serine). Incorporating flexons between one or more sites of the subject Abu is believed to promote functionality by allowing them to assume a conformations relatively independent of each other. Such a construction generally provides additional flexibility to the antigen-binding domain. Suitable flexons preferably comprise between about four and about one hundred amino acids, more preferably about four to fifty amino acids, and even more preferably about four to fifteen amino acids.

Heterodimerization sequences applicable for constructing the subject Abus can be derived from a variety of sources. Generally, any protein sequences involved in the formation of stable heteromultimers are candidate heterodimerization sequences. As such, these sequences may be derived from any heteromultimeric protein complexes. Representative candidate sequences are viral proteins such as the capsid proteins of adeno-associated viruses, protein kinase phosphorylation sites that interact with SH2-domain-containing proteins (Cantely et al. (1993) *Cell* 72: 767-778; Cantely et al. (1995) *J. Biol. Chem.* 270(44): 26029-26032), domains of transcription factors and heterodimeric receptors, which mediate heteromer formation.

Preferred heteromultimeric transcription factors are a-Pal/Max complexes and Hox/Pbx complexes. Hox represents a large family of transcription factors involved in patterning the anterior-posterior axis during embryogenesis. Hox proteins bind DNA with a conserved three alpha helix homeodomain. In order to bind to specific DNA sequences, Hox proteins require the presence of hetero-partners such as the Pbx homeodomain. Wolberger et al. solved the 2.35A crystal structure of a HoxB1-Pbx1-DNA ternary complex in order to understand how Hox-Pbx complex formation occurs and how this complex binds to DNA. The structure shows that the homeodomain of each protein binds to adjacent recognition sequences on opposite sides of the DNA. Heterodimerization occurs through contacts formed between a six amino acid hexapeptide N-terminal to the homeodomain of HoxB1 and a pocket in Pbx1 formed between helix 3 and helices 1 and 2. A C-terminal extension of the Pbx1 homeodomain forms an alpha helix that packs against helix 1 to form a larger four helix homeodomain (Wolberger et al. (1999) *Cell* 96: 587-597; Wolberger et al. *J. Mol. Biol.* 291: 521-530).

A vast number of heterodimeric receptors have also been identified. They include but are not limited to those that bind to growth factors (e.g. heregulin), neurotransmitters (e.g. γ-Aminobutyric acid), and other organic or inorganic small molecules (e.g. mineralocorticoid, glucocorticoid). Preferred heterodimeric receptors are nuclear hormone receptors (Belshaw et al. (1996) *Proc. Natl. Acad. Sci. U S. A* 93(10): 4604-4607), erbB3 and erbB2 receptor complex, and G-protein-coupled receptors including but not limited to opioid (Gomes et al. (2000) *J Neuroscience* 20(22): RC110); Jordan et al. (1999) *Nature* 399:697-700), muscarinic, dopamine, serotonin, adenosine/dopamine, and $GABA_B$ families of receptors. For majority of the known heterodimeric receptors, their C-terminal sequences are found to mediate heterodimer formation.

Where desired, sequences from novel heterodimeric receptors can be employed in constructing the subject Abus. In such situation, the identification of a candidate heterodimerization sequences in a given receptor pair can be determined by any genetic or biochemical assays without undue experimentation. Additionally, computer modeling and searching technologies further facilitates detection of heterodimerization sequences homologies of common domains appeared in related and unrelated genes. Non-limiting examples of programs that allow homology searches are Blast, Fasta (Genetics Computing Group package, Madison, Wis.), DNA Star, Clustlaw, TOFFEE, COBLATH, Genthreaderi, and MegAlign. Any sequence databases that contains DNA sequences corresponding to a target receptor or a segment thereof can be used for sequence analysis. Commonly employed databases include but are not limited to GenBank, EMBL, DDBJ, PDB, SWISS-PORT, EST, STS, GSS, and HTGS.

Another preferred class of heterodimerization sequences consists of amphiphilic peptides that adopt a coiled-coil helical structure. The helical coiled coil is one of the principal subunit oligomerization sequences in proteins. Primary sequence analysis reveals that approximately 2-3% of all protein residues form coiled coils (Wolf et al. (1997) *Protein Sci.* 6:1179-1189). Well-characterized coiled-coil-containing proteins include members of the cytoskeletal family (e.g. α-keratin, vimentin), cytoskeletal motor family (e.g. myosine, kinesins, and dyneins), viral membrane proteins (e.g. membrane proteins of Ebola or HIV), DNA binding proteins, and cell surface receptors (e.g. $GABA_B$ receptors 1 and 2). Coiled-coil heterodimerization sequences of the present invention can be broadly classified into two groups, namely the left-handed and right-handed coiled coils. The left-handed coiled coils are characterized by a heptad repeat denoted "abcdefg" with the occurrence of apolar residues preferentially located at the first (a) and fourth (d) position. The residues at these two positions typically constitute a zig-zag pattern of "knobs and holes" that interlock with those of the other stand to form a tight-fitting hydrophobic core. In contrast, the second (b), third (c) and sixth (f) positions that cover the periphery of the coiled coil are preferably charged residues. Examples of charged amino acids include basic residues such as lysine, arginine, histidine, and acidic residues such as aspartate, glutamate, asparagine, and glutamine. Uncharged or apolar amino acids suitable for designing a heterodimeric coiled coil include but are not limited to glycine, alanine, valine, leucine, isoleucine, serine and threonine. While the uncharged residues typically form the hydrophobic core, inter-helical and intra-helical salt-bridge including charged residues even at core positions may be employed to stabilize the overall helical coiled-coiled structure (Burkhard et al. (2000) *J. Biol. Chem.* 275:11672-11677). Whereas varying lengths of coiled coil may be employed, the subject heterodimerization sequences preferably contain two to ten heptad repeats. More preferably, the heterodimerization sequences contain three to eight heptad repeats, even more preferably contain four to five heptad repeats.

In designing optimal coiled-coil heterodimerization sequences, a variety of existing computer software programs that predict the secondary structure of a peptide can be used. An illustrative computer analysis uses the COILS algorithm which compares an amino acid sequence with sequences in the database of known two-stranded coiled coils, and predicts the high probability coiled-coil stretches (Kammerer et al. (1999) *Biochemistry* 38:13263-13269).

While a diverse variety of coiled coils involved in hetero-oligomerization can be employed in the subject invention, preferred coiled coils are derived from heterodimeric receptors. Accordingly, the present invention encompasses the coiled-coil dimeric sequences derived from $GABA_B$ receptors 1 and 2. In one aspect, the subject coiled coils comprise the C-terminal sequences of $GABA_B$ receptor 1 and $GABA_B$ receptor 2. In another aspect, the subject coiled coils are further linked to cysteine residues. The coiled coils are $GABA_B$ receptor 1 and 2 polypeptides of at least 30 amino acid residues, one of which is essentially identical to a linear sequence of comparable length depicted in SEQ ID NO. 2, and the other is essentially identical to a linear peptide sequence of comparable length depicted in SEQ ID NO. 4.

A linear sequence of peptide is "essentially identical" to another linear sequence, if both sequences exhibit substantial amino acid sequence homology. Generally, essentially identical sequences are at least about 60% identical with each other, after alignment of the homologous regions. Preferably, the sequences are at least about 70% identical; more preferably, they are at least about 80% identical; more preferably, they are at least about 90% identical; more preferably, the sequences are at least about 95% identical; still more preferably, the sequences are 100% identical.

In determining whether polypeptide sequences are essentially identical, a sequence that preserves the functionality of the polypeptide with which it is being compared is particularly preferred. Functionality may be established by different criteria, such as ability to form a heterodimer with a pairing coiled-coil sequence, and inability to form a homodimer under physiological buffer conditions and/or physiological body temperatures.

The invention includes modified $GABA_B$ heterodimerization sequences which are functionally equivalent to the sequences exemplified herein. Modified polypeptides providing improved stability to the resulting Abus are preferred. Examples of modified polypeptides include those with conservative substitutions of amino acid residues, and one or more deletions or additions of amino acids which do not significantly deleteriously alter the heterodimerization specificity. Substitutions can range from changing or modifying one or more amino acid residues to complete redesign of a region as long as the pairwise affinity is maintained. Amino acid substitutions, if present, are preferably conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid; serine/threonine/methionine; lysine/arginine; and phenylalanine/tryosine/tryptophan. Polypeptides of this invention can be in glycosylated or unglycosylated form, can be modified post-translationally (e.g., acetylation, and phosphorylation) or can be modified synthetically (e.g., the attachment of a labeling group).

Figure 12:
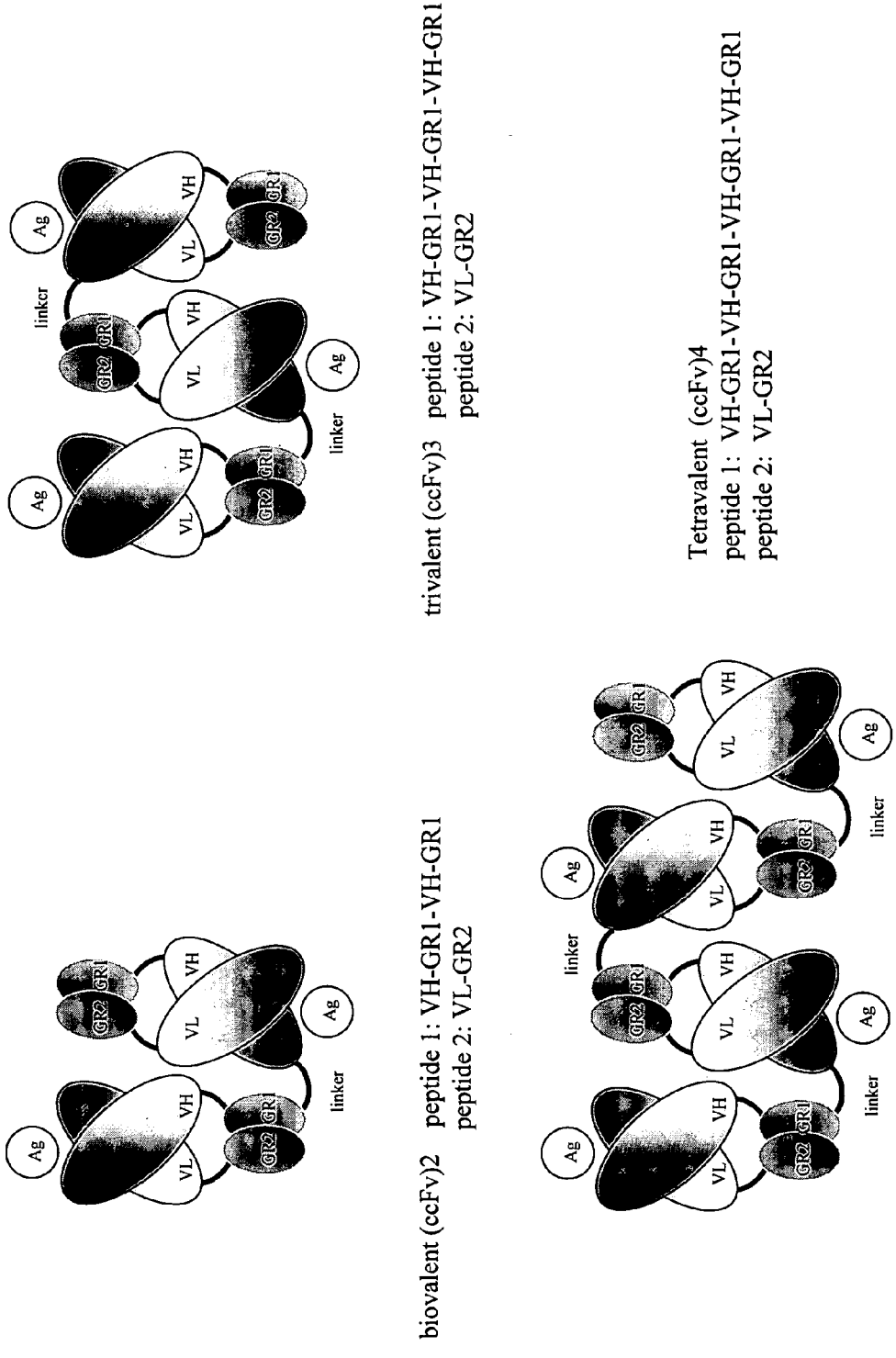
FIG. 12 depicts three multivalent Abu configurations, each comprising more than one basic ccFv unit.

Configurations and Modifications of Antigen-Binding Units (Abus):

The Abus of the present invention can adopt a variety of configurations. The smallest non-single chain Abu is a monovalent ccFv fragment. The ccFv fragment is a dimeric protein composed of VL and VH regions, which dimerize via the pairwise affinity of the first and second heterodimerization sequences fused in-frame with the VL and VH regions, respectively. Preferably, the ccFv contains a short flexon sequence that provides additional flexibility to the VL and VH regions (see an exemplary ccFv in FIG. 1). A more complex Nsc Abu is a multivalent molecule capable of binding to more than one antigen of the same kind (i.e. multivalent but mono-specific) or different kind (i.e. multivalent and multispecific Abus). Typically, a multivalent Abu is a heteromultimer composed of more than one L and H chain polypeptides, in which either the L or H polypeptide or both contain more than one V region. For instance, an exemplary bivalent Abus assumes the configuration of $(ccFv)_2$ as depicted in FIG. 12. The H chain polypeptide in this illustrative bivalent Abus contains two VH regions, each of which dimerizes with a VL region to constitute two antigen-binding sites. Alternatively, the L chain polypeptide may provide two VL regions, each of which dimerizes with a VH region to reconstitute the two binding sites. As shown in FIG. 12, the multivalent Abu is stabilized via pairwise affinity of the two heterodimerization sequences linked to the VL and VH regions. The Abu is assembled efficiently because at least one, and preferably both, of the heterodimerization sequences is or are incapable of forming homodimers, thus minimizing intra-molecular dimerization to form nonfunctional VH/VH or VL/VL dimers. Applying this general antibody engineering scheme, trivalent and tetravalent Abus can be constructed (see, e.g. FIG. 12).

Figure 13:
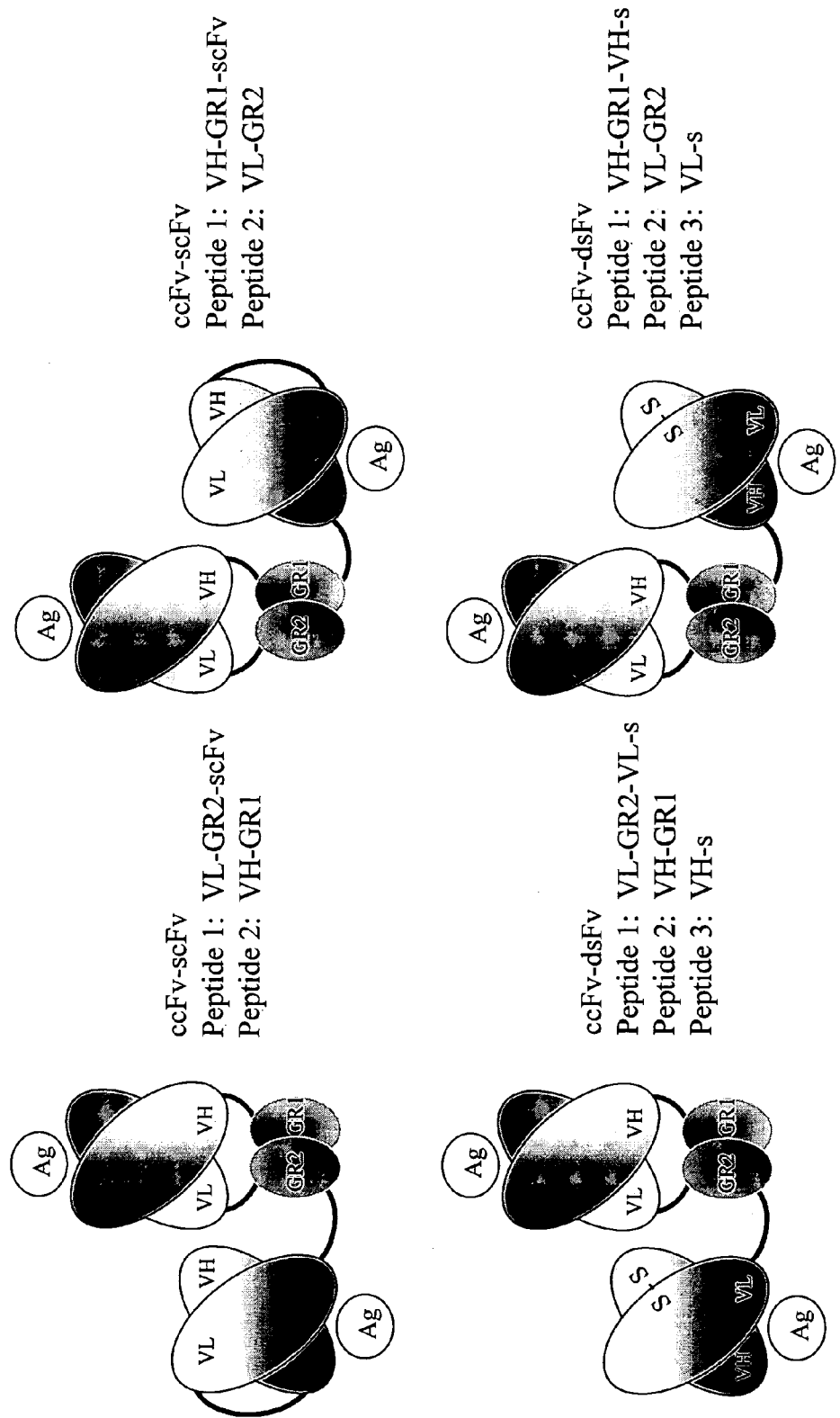
FIG. 13 depicts four bivalent Abu configurations, each comprising a basic ccFv unit and a scFv or a dsFv fragment.

A variant approach to construct multivalent Abus employs a scFv or dsFv fragment as illustrated in FIG. 13. In addition to the building unit ccFv that provides one antigen-binding site, Abus of this configuration contains one or more scFv or dsFv fragments that are linked to the ccFv. The linked scFv or dsFv provides the additional binding sites. For instance, a bivalent Abus may adopt the ccFv-scFv or ccFv-dsFv configuration (FIG. 13). Whereas one of the antigen-binding site is assembled via the pairwise affinity of the heterodimerization sequences linked to the VL region and VH region (as in ccFv), the other is provided by the scFv or dsFv fragment that is fused in-frame with the VL region. Alternatively, the scFv or dsFv fragment can be linked to the VH region.

Figure 14:
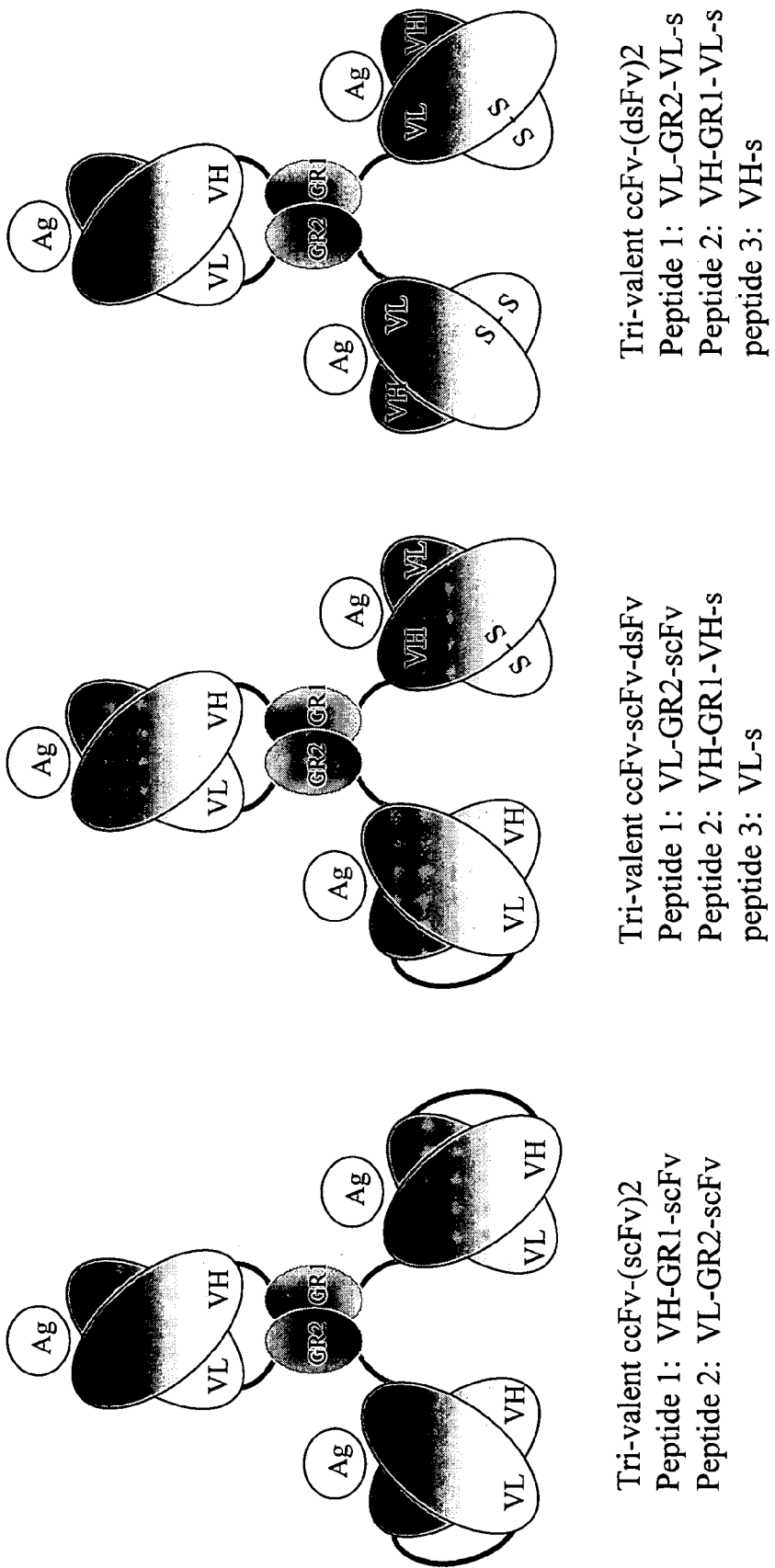
FIG. 14 depicts three trivalent Abu configurations, each comprising one or more basic ccFv unit, one or more scFv or dsFv fragment.

The same approach can be employed to generate trivalent ccFv-scFv or ccFv-dsFv Abus as shown in FIG. 14. In one aspect, the trivalent Abus assumes the configuration of ccFv-(scFv)$_2$, in which two polypeptides "VH-first heterodimerization sequence-scFv" and "VL-second heterodimerization sequence-scFv" dimerize via the pairwise affinity of the two heterodimerization sequences to constitute three binding sites. One of the binding sites is composed of the VL and VH regions of the ccFv building units; the remaining two are provided by the scFv fragments linked to the respective VL an VH polypeptides. Alternatively, the multivalent Abus can be configured as ccFv-scFv-dsFv. In this configuration, one of the antigen-binding sites is assembled and stabilized via an inter-molecular disulfide bond between a pair of cysteine residues that is located within the VH and VL regions of the dsFv fragment. A further variant of this configuration is a trivalent ccFv-(dsFv)$_2$, in which two of the binding sites assume the dsFv format (see, e.g. FIG. 14). Any other multivalent Abus variants employing the basic ccFv building unit, whether being monospecific or multispecifc, are encompassed by this invention.

Accordingly, this invention further provides multispecific Abus. They are multivalent molecules capable of binding to at least two distinct antigens. Preferred multispecific Abus are bispecific and trispecific molecules exhibiting binding specificities to two and three distinct antigens, respectively. Distinguished from previously characterized multispecific antibodies (see e.g. U.S. Pat. No. 5,932,448), the subject multispecific Abus comprises one or more ccFv building unit with distinct binding specificities. The subject multispecific Abus can also incorporate one or more scFv or dsFv fragments as detailed above. Preferred bispecific and trispecific Abus are configured according to the general structures depicted in FIGS. 15-17.

Aside from non-single chain Abus, the present invention includes single-chain Abus that is stabilized by the subject heterodimerization sequences. Typically, the Sc Abus comprises a VL and a VH region forming an intra-molecular dimer via the pairwise affinity of the heterodimerization sequences connected to these two regions. The heterodimerization sequences may be configured in either a parallel or anti-parallel manner (see, e.g. FIG. 18). In a parallel configuration, the two heterodimerzation sequences are aligned such that they have the same orientation (amino-terminal to carboxyl-terminal). In an anti-parallel configuration, the heterodimerization sequences are arranged such that the amino-terminal end of one sequence is aligned with the carboxyl-terminal end of the other sequence, and vice versa. Generally, the heterodimerization sequences are linked together via a flexon sequence. As described herein, flexon is a flexible polypeptide linker (or a nucleic acid sequence encoding such a polypeptide) which typically comprises amino acids having small side chains (e.g. glycine, alanine, valine, leucine, isoleucine, and serine). Incorporating flexons between the two heterodimerization sequences generally provides spatial flexibility for them to form an intra-molecular dimer. Suitable flexons for the anti-parallel configuration preferably comprise between about four to about one hundred amino acids, more preferably about four to fifty amino acids, and even more preferably about four to fifteen amino acids. Flexons for the parallel configuration are generally longer, preferably ranging from about ten to about one hundred amino acids, more preferably from about fifty to about thirty amino acid residues.

Where desired, one or more pairs of cysteine residues may be incorporated at the N- or C-terminus of the heterodimerization sequences to further stabilize the Abus of the present invention.

The Abus of this invention may contain sequences derived from the constant regions of an L chain or a H chain. Such sequences derived from the constant regions are generally placed between a light-chain or a heavy-chain variable region and the heterodimerization sequence to which it is linked. In addition, the light and heavy chains may contain partly or entirely human sequences.

Methods for humanizing non-human antibodies are well known in the art. "Humanized" antibodies are antibodies in which at least part of the sequence has been altered from its initial form to render it more like human immunoglobulins. In one version, the H chain and L chain C regions are replaced with human sequence. This is a fusion polypeptide comprising a V region and a heterologous immunoglobulin C region. In another version, the CDR regions comprise non human antibody sequences, while the V framework regions have also been converted to human sequences. See, for example, EP 0329400. In a third version, V regions are humanized by designing consensus sequences of human and mouse V regions, and converting residues outside the CDRs that are different between the consensus sequences.

In making humanized antibodies, the choice of framework residues can be critical in retaining high binding affinity. In principle, a framework sequence from any HuAb can serve as the template for CDR grafting; however, it has been demonstrated that straight CDR replacement into such a framework can lead to significant loss of binding affinity to the antigen. Glaser et al. (1992) *J. Immunol.* 149:2606; Tempest et al. (1992) *Biotechnology* 9:266; and Shalaby et al. (1992) *J. Exp. Med.* 17:217. The more homologous a HuAb is to the original muAb, the less likely that the human framework will introduce distortions into the murine CDRs that could reduce affinity. Based on a sequence homology search against an antibody sequence database, the HuAb IC4 provides good framework homology to muM4TS.22, although other highly homologous HuAbs would be suitable as well, especially kappa L chains from human subgroup I or H chains from human subgroup III. Kabat et al. (1987). Various computer programs such as ENCAD (Levitt et al. (1983) *J. Mol. Biol.* 168:595) are available to predict the ideal sequence for the V region. The invention thus encompasses HuAbs with different V regions. It is within the skill of one in the art to determine suitable V region sequences and to optimize these sequences. Methods for obtaining antibodies with reduced immunogenicity are also described in U.S. Pat. No. 5,270,202 and EP 699,755.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved.

The invention also encompasses Abus conjugated to a chemically functional moiety. Typically, the moiety is a label capable of producing a detectable signal. These conjugated Abus are useful, for example, in detection systems such as quantitation of tumor burden, and imaging of metastatic foci and tumor imaging. Such labels are known in the art and include, but are not limited to, radioisotopes, enzymes, fluorescent compounds, chemiluminescent compounds, bioluminescent compounds substrate cofactors and inhibitors. See, for examples of patents teaching the use of such labels, U.S. Pat. Nos. 3,817,837; 3,850,752; 3,939,350; 3,996,345; 4,277, 437; 4,275,149; and 4,366,241. The moieties can be covalently linked to Abus, recombinantly linked, or conjugated to Abus through a secondary reagent, such as a second antibody, protein A, or a biotin-avidin complex.

Other functional moieties include signal peptides, agents that enhance immunologic reactivity, agents that facilitate coupling to a solid support, vaccine carriers, bioresponse modifiers, paramagnetic labels and drugs. Signal peptides is a short amino acid sequence that directs a newly synthesized protein through a cellular membrane, usually the endoplasmic reticulum in eukaryotic cells, and either the inner membrane or both inner and outer membranes of bacteria. Signal peptides are typically at the N-terminal portion of a polypeptide and are typically removed enzymatically between biosynthesis and secretion of the polypeptide from the cell. Such a peptide can be incorporated into the subject Abus to allow secretion of the synthesized molecules.

Agents that enhance immunologic reactivity include, but are not limited to, bacterial superantigens. Agents that facilitate coupling to a solid support include, but are not limited to, biotin or avidin. Immunogen carriers include, but are not limited to, any physiologically acceptable buffers. Bioresponse modifiers include cytokines, particularly tumor necrosis factor (TNF), interleukin-2, interleukin-4, granulocyte macrophage colony stimulating factor and γ-interferons.

Suitable drug moieties include antineoplastic agents. Non-limiting examples are radioisotopes, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

Immunotoxins, including single chain molecules, can be produced by recombinant means. Production of various immunotoxins is well-known in the art, and methods can be found, for example, in "Monoclonal Antibody-toxin Conjugates: Aiming the Magic Bullet," Thorpe et al. (1982) *Monoclonal Antibodies in Clinical Medicine*, Academic Press, pp. 168-190; Vitatta (1987) *Science* 238:1098-1104; and Winter and Milstein (1991) *Nature* 349:293-299. Suitable toxins include, but are not limited to, ricin, radionuclides, pokeweed antiviral protein, *Pseudomonas* exotoxin A, diphtheria toxin, ricin A chain, fungal toxins such as restrictocin and phospholipase enzymes. See, generally, "Chimeric Toxins," Olsnes and Pihl, *Pharmac. Ther.* 15:355-381 (1981); and "Monoclonal Antibodies for Cancer Detection and Therapy," eds. Baldwin and Byers, pp. 159-179, 224-266, Academic Press (1985).

The chemically functional moieties can be made recombinantly for instance by creating a fusion gene encoding the Abu and the functional moiety. Alternatively, the Abu can be chemically bonded to the moiety by any of a variety of well-established chemical procedures. For example, when the moiety is a protein, the linkage may be by way of heterobifunctional cross linkers, e.g., SPDP, carbodiimide glutaraldehyde, or the like. The moieties may be covalently linked, or conjugated, through a secondary reagent, such as a second antibody, protein A, or a biotin-avidin complex. Paramagnetic moieties and the conjugation thereof to antibodies are well-known in the art. See, e.g., Miltenyi et al. (1990) *Cytometry* 11:231-238.

Preparation of Antigen-Binding Units (Abus):

The subject Abus can be prepared by recombinant DNA technology, synthetic chemistry techniques, or a combination thereof. For instance, sequences encoding the desired components of the Abus, including VL, VH and the heterodimerization sequences are typically assembled and fragments ligated into an expression vector. These sequences may be assembled from other vectors encoding the desired protein sequence, from PCR-generated fragments using respective template nucleic acids, or by assembly of synthetic oligonucleotides encoding the desired sequences. However, all nucleic acid sequences encoding the Abus are preferably assembled by in-frame fusion of coding sequences. Flexons, described above, can be included between various components and domains in order to enhance the ability of the individual components to assume a configurations relatively independently of each other. To produce Nsc Abus, the L and H chain can be formed separately and then assembled, or assembled in vivo by an expression system for both chains. Such expression systems can be created by transfecting a suitable cell with a vector comprising separate transcribable regions for the L and H chain, or by co-transfecting the same cell with vectors for each chain.

The assembled Abus can be isolated using a variety of protein purification techniques known in the art. Generally, the Abu is isolated from culture media as secreted polypeptides, although they can be recovered from host cell lysates or bacterial periplasm, when directly produced without signal peptides. If the Abus are membrane-bound, they be solubilized by suitable detergent solutions commonly employed by artisans in the field. The recovered Abus may be further purified by salt precipitation (e.g., with ammonium sulfate), ion exchange chromatography (e.g. on a cationic or anionic exchange column run at neutral pH and eluted with step gradients of increasing ionic strength), gel filtration chromatography (including gel filtration HPLC), and chromatography on tag-affinity column, or on affinity resins such as protein A, protein G, hydroxyapatite, and anti-immunoglobulin.

Polynucleotides and Vectors of the Present Invention

The invention provides various polynucleotides that encode the Abus of the invention. The invention polynucleotides are characterized, in part, by the unique heterodimerization sequences contained therein as detailed above. Such heterodimerization sequences enable efficient assembly of and screening for Abus, such as those that specifically bind to a desired antigen. Such sequences also facilitate display of heteromultimers on living biological entities including phages, bacteria, other prokaryotic or eukaryotic cells. Preferred heterodimerization sequences shown in SEQ ID NOS. 2 and 4.

In one embodiment, this invention provides isolate polynucleotides that encode the subject Nsc Abus. In one aspect of this embodiment, the recombinant polynucleotide comprises a coding sequence that encodes the light-chain polypeptide of a subject Nsc Abu. In another aspect, the recombinant polynucleotide comprises a coding sequence that encodes the heavy-chain polypeptide of a Nsc Abu. In yet another aspect, the recombinant polynucleotide comprises two separate coding sequences, one of which codes for the light-chain polypeptide, and the other codes for the heavy-chain.

Nucleotide sequences corresponding to various regions of L or H chains of an existing antibody can be readily obtained and sequenced using convention techniques including but not limited to hybridization, PCR, and DNA sequencing. Hybridoma cells that produce monoclonal antibodies serve as a preferred source of antibody nucleotide sequences. A vast number of hybridoma cells producing an array of monoclonal antibodies may be obtained from public or private repositories. The largest depository agent is American Type Culture Collection, which offers a diverse collection of well-characterized hybridoma cell lines. Alternatively, antibody nucleotides can be obtained from immunized or non-immunized rodents or humans, and form organs such as spleen and peripheral blood lymphocytes. Specific techniques applicable for extracting and synthesizing antibody nucleotides are described in Orlandi et al. (1989) *Proc. Natl. Acad. Sci. U.S.A* 86: 3833-3837, Larrick et al. 1989) *biochem. Biophys. Res. Commun.* 160: 1250-1255; Sastry et al. (1989) *Proc. Natl. Acad. Sci.,* U.S.A. 86: 5728-5732; and U.S. Pat. No. 5,969,108.

The antibody nucleotide sequences may also be modified, for example, by substituting the coding sequence for human heavy and light chain constant regions in place of the homologous non-human sequences. In that manner, chimeric antibodies are prepared that retain the binding specificity of the original antibody.

It is also understood that the polynucleotides embodied in the invention include those coding for functional equivalents and fragments thereof of the exemplified polypeptides. Functionally equivalent polypeptides include those that enhance, decrease or not significantly affect properties of the polypeptides encoded thereby. Functional equivalents may be polypeptides having conservative amino acid substitutions, analogs including fusions, and mutants.

Due to the degeneracy of the genetic code, there can be considerable variation in nucleotides of the L and H sequences, as well as the heterodimerization sequences suitable for construction of the polynucleotide and vectors of the present invention. Sequence variants may have modified DNA or amino acid sequences, one or more substitutions, deletions, or additions, the net effect of which is to retain the desired antigen-binding activity. For instance, various substitutions can be made in the coding region that either do not alter the amino acids encoded or result in conservative changes. These substitutions are encompassed by the present invention. Conservative amino acid substitutions include substitutions within the following groups: glycine, alanine; valine, isoleucine, leucine; aspatic acid, glutamic acid; asparagine, glutamine; serine, threonine; lysine, arginine; and phenylalanine, tyrosine. While conservative substitutions do effectively change one or more amino acid residues contained in the polypeptide to be produced, the substitutions are not expected to interfere with the antigen-binding activity of the resulting Abus to be produced. Nucleotide substitutions that do not alter the amino acid residues encoded are useful for optimizing gene expression in different systems. Suitable substitutions are known to those of skill in the art and are made, for instance, to reflect preferred codon usage in the expression systems.

Where desired, the recombinant polynucleotides may comprise heterologous sequences that facilitate detection of the expression and purification of the gene product. Examples of such sequences are known in the art and include those encoding reporter proteins such as β-galactosidase, β-lactamase, chloramphenicol acetyltransferase (CAT), luciferase, green fluorescent protein (GFP) and their derivatives. Other heterologous sequences that facilitate purification may code for epitopes such as Myc, HA (derived from influenza virus hemagglutinin), His-6, FLAG, or the Fc portion of immunoglobulin, glutathione S-transferase (GST), and maltose-binding protein (MBP).

The polynucleotides can be conjugated to a variety of chemically functional moieties described above. Commonly employed moieties include labels capable of producing a detectable signal, signal peptides, agents that enhance immunologic reactivity, agents that facilitate coupling to a solid support, vaccine carriers, bioresponse modifiers, paramagnetic labels and drugs. The moieties can be covalently linked polynucleotide recombinantly or by other means known in the art.

The polynucleotides of the invention can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

The polynucleotides embodied in this invention can be obtained using chemical synthesis, recombinant cloning methods, PCR, or any combination thereof. Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Polynucleotides comprising a desired sequence can be inserted into a suitable vector which in turn can be introduced into a suitable host cell for replication and amplification. Accordingly, the invention encompasses a variety of vectors comprising one or more of the polynucleotides of the present invention. Also provided is a selectable library of expression vectors comprising at least one vector encoding the subject Abus.

Vectors of the present invention are generally categorized into cloning and expression vectors. Cloning vectors are useful for obtaining replicate copies of the polynucleotides they contain, or as a means of storing the polynucleotides in a depository for future recovery. Expression vectors (and host cells containing these expression vectors) can be used to obtain polypeptides produced from the polynucleotides they contain. Suitable cloning and expression vectors include any known in the art, e.g., those for use in bacterial, mammalian, yeast, insect and phage display expression systems.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pBR322, pMB9, ColE1, pCR1, RP4, pUC18, mp18, mp19, phage DNAs (including filamentous and non-filamentous phage DNAs), and shuttle vectors such as pSA3 and pAT28. These and other cloning vectors are available from commercial vendors such as Clontech, BiORad, Stratagene, and Invitrogen.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including phagemids, adenoviruses, adeno-associated viruses, retroviruses, cosmids, etc. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer. Two types of particularly useful expression vectors for expressing the subject Abus are the phage display vector and bacterial display vector.

The techniques for constructing phage display vectors are well established in the art (see review article by Winter G. et al. (1994) *Ann. Rev. Immunol.* 12:433-55). Both filamentous and non-filamentous phage sequences are applicable for constructing a display vector. Filamentous phage vectors are preferred because the genomes of many representative phages of this class have been sequenced, and their genomes are found to be much smaller than that of non-filamentous phages. Representative phages of this class include M13, f1, fd, If1, Ike, Xf, Pf1, and Pf3. The phage vector typically is constructed to express heteromultimers, e.g. antibody peptides, by fusion to a part or all of a phage coat protein. Suitable coat proteins include pIII, VIII, VI, VII and IX of M13. The heteromultimer sequence must be inserted into the phage vector in such a way that the integrity of the expressed phage coat is not undermined, and the heteromultimer is preferably biologically functional.

For constructing pIII fusion vector, commonly employed fusion sites are located at the amino terminus, in between the flexible spacer between the two domains of pIII (Smith et al. *Science* 288:1315-17), or any other alternative fusion sites described in U.S. Pat. Nos. 5,969,108, 5,837,500. The pIII fusion and other proteins of the phage can be encoded entirely within the same page replicon or on different replicons. When at least two replicons are used, the pIII fusion is generally encoded on a phagemid, a plasmid containing a phage origin of replication. Phagemids can be packaged into phage particles by "rescue" with a helper phage such as M13KO7, which provides all the phage proteins, including pIII, but due to a defect origin is itself poorly packaged in competition with the phagemids. Other multivalent helper phages (e.g. M13ΔgIII) that lack or contain altered pIII to enhance the package efficiency can also be employed (Rondot et al. *Nature Biotechnology* 19:75-78).

Similar constructions can be made with other filamentous phage. Pf3 is a well-known filamentous phage that infects *Pseudomonas aerugenosa* cells that harbor an IncP-1 plasmid. The entire genome has been sequenced and the genetic signals involved in replication and assembly are characterized. The major coat protein of PF3 is unusual in having no signal peptide to direct its secretion. The sequence has charged residues $ASP_7$, $ARG_{37}$, $LYS_{40}$, and $PHE_{44}$-$COO^-$ which is consistent with the amino terminus being exposed. To construct a display Pf3 vector, it is generally desirable to engineer a signal sequence known to cause secretion in *P. aerugenosa* fused in-frame to a gene fragment encoding a heterologous polypeptide, which in turn is fused in-frame with a DNA encoding the mature Pf3 coat protein.

The same general construction scheme applies to generating display vectors containing sequences derived from non-filamentous phages including bacteriophage X174, λ, T4 and T7 phages. A wealth of information on the structures of these non-filamentous phages is known in the art. One skilled in the art can readily generate a corresponding display vector that expresses the subject heteromultimers using the unique heterodimerization sequences without undue experimentation.

In addition to phage display vector, another class of preferred vector is bacterial display vector. The general scheme outlined above is equally applicable for constructing such vectors. Briefly, the vectors facilitate expression of a heteromultimer, Abus in particular, as a fusion with a bacterial surface protein. Prior research has revealed a vast number of bacterial surface proteins applicable for expressing such fusions. Non-limiting examples of bacterial surface proteins are LamB (Bremer et al. *Proc. Natl. Acad. Sci U.S.A.* (1984) 81:3830-34; *Gene* (1987) 52:165-73); OmpA (Prog Biophys Molec Biol (1987) 49:89-115); OmpC; OmpF (Pages et al. *Biochemimie* (1990) 72:169-76); PhoE (van der Ley et al. *J. Biol. Chem.* 261:12222-5); pilin (So et al. *Curr Top in Microbiol & Immunol* (1985) 118:13-28); pldA (de Geus et al. *EMBO J.* (1984) 3(8): 1799-1802) and their homologs. Characterization of these and other surface proteins, and the methods of using these proteins for displaying heterologous polypeptides are detailed in U.S. Pat. No. 5,837,500 as well as the references cited therein.

The vectors of the present invention generally comprises a transcriptional or translational control sequences required for expressing the Abus. Suitable transcription or translational control sequences include but are not limited to replication origin, promoter, enhancer, repressor binding regions, transcription initiation sites, ribosome binding sites, translation initiation sites, and termination sites for transcription and translation.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase. Eukaryotic promoters will often, but not always, contain "TATA" boxes and "CAT" boxes.

The choice of promoters will largely depend on the host cells in which the vector is introduced. For animal cells, a variety of robust promoters, both viral and non-viral promoters, are known in the art. Non-limiting representative viral promoters include CMV, the early and late promoters of SV40 virus, promoters of various types of adenoviruses (e.g. adenovirus 2) and adeno-associated viruses. It is also possible, and often desirable, to utilize promoters normally associated with a desired light or heavy chain gene, provided that such control sequences are compatible with the host cell system.

Suitable promoter sequences for other eukaryotic cells include the promoters for 3-phosphoglycerate kinase, or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In certain preferred embodiments, the vectors of the present invention use strong enhancer and promoter expression cassettes. Examples of such expression cassettes include the human cytomegalovirus immediately early (HCMV-IE) promoter (Boshart et al, Cell 41: 521,(1985)), the β-actin promoter (Gunning et al. (1987) *Proc. Natl. Acad. Sci.* (USA) 84: 5831), the histone H4 promoter (Guild et al.(1988), *J Viral.* 62: 3795), the mouse metallothionein promoter (McIvor et al. (1987), *Mol, Cell. Biol.* 7: 838), the rat growth hormone promoter (Millet et al. (1985), *Mol. Cell Biol.* 5: 431), the human adenosine deaminase promoter (Hantzapoulos et al. (1989) *Proc. Natl. Acad. Sci. USA* 86: 3519), the HSV tk promoter 25 (Tabin et al. (1982) *Mol. Cell. Biol.* 2: 426), the α-1 antitrypsin enhancer (Peng et al. (1988) *Proc. Natl. Acad. Sci. USA* 85: 8146), and the immunoglobulin enhancer/promoter (Blankenstein et al. (1988) *Nucleic Acid Res.* 16: 10939), the SV40 early or late promoters, the Adenovirus 2 major late promoter, or other viral promoters derived from polyoma viris, bovine papilloma virus, or other retroviruses or adenoviruses. The promoter and enhancer elements of immunoglobulin (Ig) genes confer marked specificity to B lymphocytes (Banerji et al. (1983) *Cell* 33: 729; Gillies et al. (1983) *Cell* 33: 717; Mason et al. (1985) *Cell* 41: 479), while the elements controlling transcription of the B-globin gene function only in erythroid cells (van Assendelft et al. (1989) *Cell* 56:969).

Cell-specific or tissue-specific promoters may also be used. A vast diversity of tissue specific promoters have been described and employed by artisans in the field. Exemplary promoters operative in selective animal cells include hepatocyte-specific promoters and cardiac muscle specific promoters. Depending on the choice of the recipient cell types, those skilled in the art will know of other suitable cell-specific or tissue-specific promoters applicable for the construction of the expression vectors of the present invention.

Using well-known restriction and ligation techniques, appropriate transcriptional control sequences can be excised from various DNA sources and integrated in operative relationship with the intact selectable fusion genes to be expressed in accordance with the present invention.

In constructing the subject vectors, the termination sequences associated with the exogenous sequences are also inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional read-through. Preferred terminator sequences (or termination sites) of the present invention have a gene that is followed by a transcription termination sequence, either its own termination sequence or a heterologous termination sequence. Examples of such termination sequences include stop codons coupled to various polyadenylation sequences that are known in the art, widely available, and exemplified below. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, neomycyin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In a preferred embodiment, the vector is a shuttle vector, capable of replicating in at least two unrelated expression systems. In order to facilitate such replication, the vector generally contains at least two origins of replication, one effective in each expression system. Typically, shuttle vectors are capable of replicating in a eukaryotic expression system and a prokaryotic expression system. This enables detection of protein expression in the eukaryotic host (the expression cell type) and amplification of the vector in the prokaryotic host (the amplification cell type). Preferably, one origin of replication is derived from SV40 and one is derived from pBR322 although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized The vectors embodied in this invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art.

Host Cells of the Present Invention:

The invention provides host cells transfected with the vectors or a library of the expression vectors described above. The expression vectors can be introduced into a suitable prokaryotic or eukaryotic cell by any of a number of appropriate means, including electroporation, microprojectile bombardment; lipofection, infection (where the vector is coupled to an infectious agent), transfection employing calcium chloride, rubidium chloride, calcium phosphate, DEAE-dextran, or other substances. The choice of the means for introducing vectors will often depend on features of the host cell.

For most animal cells, any of the above-mentioned methods is suitable for vector delivery. Preferred animal cells are vertebrate cells, preferably mammalian cells, capable of expressing exogenously introduced gene products in large quantity, e.g. at the milligram level. Non-limiting examples of preferred cells are NIH3T3 cells, COS, HeLa, and CHO cells.

The animal cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, animal cells can be grown in a defined medium that lacks serum but is supplemented with hormones, growth factors or any other factors necessary for the survival and/or growth of a particular cell type. Whereas a defined medium supporting cell survival maintains the viability, morphology, capacity to metabolize and potentially, capacity of the cell to differentiate, a defined medium promoting cell growth provides all chemicals necessary for cell proliferation or multiplication. The general parameters governing mammalian cell survival and growth in vitro are well established in the art. Physicochemical parameters which may be controlled in different cell culture systems are, e.g., pH, $pO_2$, temperature, and osmolarity. The nutritional requirements of cells are usually provided in standard media formulations developed to provide an optimal environment. Nutrients can be divided into several categories: amino acids and their derivatives, carbohydrates, sugars, fatty acids, complex lipids, nucleic acid derivatives and vitamins. Apart from nutrients for maintaining cell metabolism, most cells also require one or more hormones from at least one of the following groups: steroids, prostaglandins, growth factors, pituitary hormones, and peptide hormones to proliferate in serum-free media (Sato, G. H., et al. in "Growth of Cells in Hormonally Defined Media", Cold Spring Harbor Press, N.Y., 1982). In addition to hormones, cells may require transport proteins such as transferrin (plasma iron transport protein), ceruloplasmin (a copper transport protein), and high-density lipoprotein (a lipid carrier) for survival and growth in vitro. The set of optimal hormones or transport proteins will vary for each cell type. Most of these hormones or transport proteins have been added exogenously or, in a rare case, a mutant cell line has been found which does not require a particular factor. Those skilled in the art will know of other factors required for maintaining a cell culture without undue experimentation.

For plant cells, a variety of vector delivery techniques is available in the art. The host cells may be in the form of whole plants, isolated cells or protoplasts. Illustrative procedures for introducing vectors into plant cells include *Agrobacterium*-mediated plant transformation, protoplast transformation, gene transfer into pollen, injection into reproductive organs and injection into immature embryos. As is evident to one skilled in the art, each of these methods has distinct advantages and disadvantages. Thus, one particular method of introducing vectors into a particular plant species may not necessarily be the most effective for another plant species.

*Agrobacterium tumefaciens*-mediated transfer is a widely applicable system for introducing vectors into plant cells because the vector can be introduced into whole plant tissues, bypassing the need for regeneration of an intact plant from a protoplast. The use of *Agrobacterium*-mediated expression vectors to introduce vector into plant cells is well known in the art. This technique makes use of a common feature of *Agrobacterium* which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant.

Because not all plants are natural hosts for *Agrobacterium*, alternative methods such as transformation of protoplasts may be employed to introduce the subject vectors into the host cells. For certain monocots, transformation of the plant protoplasts can be achieved using methods based on calcium phosphate precipitation, polyethylene glycol treatment, electroporation, and combinations of these treatments.

In addition to protoplast transformation, particle bombardment is an alternative and convenient technique for delivering the invention vectors into a plant host cell. Specifically, the plant cells may be bombarded with microparticles coated with a plurality of the subject vectors. Bombardment with DNA-coated microprojectiles has been successfully used to produce stable transformants in both plants and animals (see, for example, Sanford et al. (1993) *Methods in Enzymology*, 217:483-509). Microparticles suitable for introducing vectors into a plant cell are typically made of metal, preferably tungsten or gold. These microparticles are available for example, from BiORad (e.g., Bio-Rad's PDS-1000/He). Those skilled in the art will know that the particle bombardment protocol can be optimized for any plant by varying parameters such as He pressure, quantity of coated particles, distance between the macrocarrier and the stopping screen and flying distance from the stopping screen to the target.

Vectors can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Alternatively, the vectors can be injected into reproductive organs of a plant as described by Pena et al., *Nature*, 325:274 (1987).

Other techniques for introducing nucleic acids into a plant cell include:
(a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed.
(b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves.
(c) High Pressure Spray of Single Leaves. Single plant inoculations can also be performed by spraying the leaves with a narrow, directed spray (50 psi, 6-12 inches from the leaf) containing approximately 1% carborundum in the buffered vector solution.
(d) Vacuum Infiltration. Inoculations may be accomplished by subjecting a host organism to a substantially vacuum pressure environment in order to facilitate infection.

Other suitable host cells for cloning and expressing the subject vectors are prokaryotes and eukaryotic microbes such as fungi or yeast cells. Suitable prokaryotes for this purpose include bacteria including Gram-negative and Gram-positive organisms. Representative members of this class of microorganisms are Enterobacteriaceae (e.g *E. coli*), *Enterobacter, Erwinia, Klebsiella, Proteus, Salmonella* (e.g. *Salmonella typhimurium*), *Serratia* (e.g., *Sefratia marcescans*), *Shigella, Neisseria* (e.g. *Neisseria meningitidis*) as well as *Bacilli* (e.g. *Bacilli subtilis* and *Bacilli licheniformis*). Preferably, the host cell secretes minimal amounts of proteolytic fragments of the expressed Abus. Commonly employed fungi (including yeast) host cells are *S. cerevisiae, Kluyveromyces lactis* (*K. lactis*), species of *Candida* including *C. albicans* and *C. glabrata, C. maltosa, C. utilis, C. stellatoidea, C. parapsilosis, C. tropicalus, Neurospora crassas, Aspergillus nidulans, Schizosaccharomyces pombe* (*S. pombe*), *Pichia pastoris*, and *Yarowia lipolytica*.

Once introduced into a suitable host cell, expression of the Abus can be determined using any nucleic acid or protein assay known in the art. For example, the presence of transcribed mRNA of L or H chain, or the Sc Abu can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934), using probes complementary to any region of Abu polynucleotide.

Expression of the vector can also be determined by examining the Abu expressed. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and PAGE-SDS.

Uses of the Polynucleotides, Vectors and Host Cells of the Present Invention:

The polynucleotides and vectors of this invention have several specific uses. They are useful, for example, in expression systems for the production of both Sc and Nsc Abus. The polynucleotides are useful as primers to effect amplification of desired polynucleotides. Furthermore, The polynucleotides of this invention are also useful in pharmaceutical compositions including vaccines, diagnostics, and drugs.

The host cells of this invention can be used, inter alia, as repositories of the subject polynucleotides, vectors, or as vehicles for producing and screening desired Abus based on their antigen binding specificities.

Accordingly, the invention provides a method of identifying a Nsc Abu that is immunoreactive with a desired antigen. The method involves the following steps: (a) preparing a genetically diverse repertoire of Abus, wherein the repertoire comprises at least one subject Abu; (b) contacting the repertoire of antigen binding units with the desired antigen; (c) detecting a specific binding between Abus and the antigen, thereby identifying the Abu that is immunoreactive with the desired antigen.

The ability of an Abu to specifically bind to a desired antigen can be tested by a variety of procedures well established in the art. See Harlow and Lane (1988) Antibodies: A Laboratory Manual, Cold Spring Harbor Laboratory, New York; Gherardi et al. (1990) *J. Immunol. Meth.* 126:61-68. Typically, Abus exhibiting desired binding specificities can be detected directly by immunoassays, for example, by reacting labeled Abus with the antigens that are immobilized on a solid support or substrate. In general, the substrate to which the antigen is adhered is fabricated with material exhibiting a low level of non-specific binding during immunoassay. A preferred solid support is made from one or more of the following types of materials: plastic polymers, glass, cellulose, nitrocellulose, semi-conducting material, and metal. Preferably, the substrate is petri dish, chromatography beads, magnetic beads, and the like.

For such solid-phase assay, the unreacted Abus are removed by washing. In a liquid-phase assay, however, the unreacted Abus are removed by some other separation technique, such as filtration or chromatography. After binding the antigen to the labeled Abus, the amount of bound label is determined. A variation of this technique is a competitive assay, in which the antigen is bound to saturation with an original binding molecule. When a population of the subject Abu is introduced to the complex, only those that exhibit higher binding affinity will be able to compete, and thus remain bound to the antigen.

Alternatively, specific binding to a given antigen can be assessed by cell sorting, which involves presenting the desired antigen on the cells to be sorted, then labeling the target cells with Abus that are coupled to detectable agents, followed by separating the labeled cells from the unlabeled ones in a cell sorter. A sophisticated cell separation method is fluorescence-activated cell sorting (FACS). Cells traveling in single file in a fine stream are passed through a laser beam, and the fluorescence of each cell bound by the fluorescently labeled Abu is then measured.

Subsequent analysis of the eluted Abus may involve protein sequencing for delineating the amino acid sequences of the L and H chains. Based on the deduced amino acid sequences, the cDNA encoding the antibody polypeptides can then be obtained by recombinant cloning methods including PCR, library screening, homology searches in existing nucleic acid databases, or any combination thereof. Commonly employed databases include but are not limited to GenBank, EMBL, DDBJ, PDB, SWISS-PROT, EST, STS, GSS, and HTGS.

When the repertoire of Abu is displayed on phage or bacterial particles, selection is preferably performed using affinity chromatography. The method typically proceeds with binding a repertoire of phage Abus to an antigen coated plates, column matrices, cells or to biotinylated antigen in solution followed by capture. The phages or bacteria bound to the solid phase are washed and then eluted by soluble hapten, acid or alkali. Alternatively, increasing concentrations of antigen can be used to dissociate the Abus from the affinity matrix. For certain Abus with extremely high affinity or avidity to the antigen, efficient elution may require high pH or mild reducing solution as described in WO 92/01047.

To avoid potential difficulties in recovering the bound Abus with the desired binding specificities, protease cleavage sites may be introduced between the heterodimerization sequences and the phage coat protein employed for displaying the Abus. Cleavage sites applicable for this purpose include but are not limited to Factor X, trypsin, and thrombin recognition sites. After binding the phage repertoire to an affinity matrix and washing the non-specific phages, the remaining phages that display the Abus with the desired affinity can be collected by washing the antigen-affinity matrix with protease under conditions suitable for digestion at the cleavage site. Such digestion would release the Abus from the phage particles.

An alternative procedure to the above is to take the affinity matrix which has retained the strongly bound phage or bacterial particles and extract their nucleic acids, for example by boiling in SDS solution. Extracted nucleic acids can be used to directly transform *E. coli* host cells or alternatively the antibody encoding sequences can be amplified by PCR using suitable primers.

The efficiency of selection is likely to depend on a combination of several factors, including the kinetics of dissociation during washing, and whether multiple Abus on a single phage or bacterium can simultaneously bind to antigens on a solid support. For example, antibodies with fast dissociation kinetics (and weak binding affinities) should be retained by use of short washes, multivalent display and a high coating density of antigen at the solid support. Conversely, the selection of Abus with slow dissociation kinetics (and good binding affinities) should be favored by use of long washes, monovalent phages, and a low coating density of antigen.

Where desired, the repertoire of Abus can be pre-selected against an unrelated antigen to counter-select the undesired Abus. The repertoire may also be pre-selected against a related antigen in order to isolate, for example, anti-idiotypic Abus.

The subject Abu repertoire enables rapid isolation of Abus with desired specificities. Many of the isolated Abus would be expected to be difficult or impossible to obtain through conventional hybridoma or transgenic animal technology.

Kits Comprising the Vectors of the Present Invention

The present invention also encompasses kits containing the vectors of this invention in suitable packaging. Kits embodied by this invention include those that allow generation of Abus reconstituted via pairwise affinity of a unique heterodimerization sequence pair as described herein.

Each kit necessarily comprises the reagents which render the delivery of vectors into a host cell possible. The selection of reagents that facilitate delivery of the vectors may vary depending on the particular transfection or infection method used. The kits may also contain reagents useful for generating labeled polynucleotide probes or proteinaceous probes for detection of Abu. Each reagent can be supplied in a solid form or dissolved/suspended in a liquid buffer suitable for inventory storage, and later for exchange or addition into the reaction medium when the experiment is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information.

Further illustration of the development and use of Abus, polynucleotides, vectors and host cells according to this invention are provided in the Example section below. The examples are provided as a guide to a practitioner of ordinary skill in the art, and are not meant to be limiting in any way.

EXAMPLES

Construction of Non-Single-Chain Antigen-Binding Units: Coiled-Coil Fv (ccFv)

As described above, the Fv fragment is the smallest antibody fragment containing the whole antigen-binding site. Composed of the two variable regions of heavy and light chain (VH and VL), Fv is located at the "upper" tips of the Y-shaped immunoglobulin molecule. The Fv fragments have very low interaction energy between their two VH and VL fragments, and are often too unstable for many applications at physiological condition. In a naturally occurring immunoglobulin (e.g. Ig), an interchain disulfide bond located in the constant domains CH1 and CL is used to link the VH and VL. This linkage makes a stabilized antigen-binding fragment Fab with a molecular weight 50 kDa. It has been shown that the VH and VL fragments can also be artificially held together by a short peptide linker between the carboxyl terminus of one fragment and amino-terminus of another to form a single-chain Fv antibody fragment (scFv). The scFv antigen-binding unit is only half the size of Fab. However, some scFv proteins are also unstable. The polypeptide linker in scFv can interfere with binding in some cases. An interchain disulfide bond has also been introduced into the framework regions in VH and VL to form a disulfide-stabilized Fv (dsFv). The dsFv configuration also has profound limitations. The introduction of two Cys residues into the antigen-binding variable regions may change the intrachain disulfide bond in VH or VL, therefore interfere with antigen binding.

We have devised a new strategy to stabilize VH and VL heterodimer. We have designed and used a unique heterodimerization sequence pair to create a Fab-like, functional artificial Fv fragment (ccFv). The heterodimerization pair were derived from the heterodimeric receptors $GABA_B$ receptors 1 and 2. The pair of sequences form a coiled-coil structure and mediate the functional heterodimerization of $GABA_B$-R1 and $GABA_B$-R2 receptors.

Distinguished from previously characterized coiled-coil leucine zippers from the Fos and Jun proteins, the C-terminal coiled coil of $GABA_B$-R1 and $GABA_B$-R2 receptors do not form detectable homodimers under physiological conditions (e.g. in vivo); nor do they form homodimers at physiological body temperatures. Research by Kuner et al. and White et al. (*Science* (1999) 283: 74-77); *Nature* (1998) 396: 679-682)) have demonstrated the heterodimerization specificity of $GABA_B$-R1 and $GABA_B$-R2 in vivo. In fact, White et al. were able to clone $GABA_B$-R2 from yeast cells based on the exclusive specificity of this heterodimeric receptor pair. In vitro studies by Kammerer et al. supra has shown that neither $GABA_B$-R1 nor $GABA_B$-R2 C-terminal sequences is capable of forming homodimers in physiological buffer conditions when assayed at physiological body temperatures (see Table 1 of Kemmerer). However, none of these researchers who were involved in the original isolation of the $GABA_B$-R2 gene and the characterization of the coiled-coil sequences describe or even suggest the use of this unique heterodimerization sequences for construction of heteromultimers such as antigen-binding units.

We have modified the carboxyl terminus of GR1 and GR2 domains by adding a flexon "SerArgGlyGlyGlyGly" (SEQ ID NO. 31) to the amino-terminus of GR1 and GR2 domains to provide additional flexibility to the V regions. To further stabilize ccFv, we have introduced a pair of cysteine residues by adding "ValGlyGlyCys" (SEQ ID NO. 29) spacer at the C-termini of the coiled coil. The GR1 and GR2 domains are fused to the carboxyl terminus of VH and VL fragment respectively. The VH-GR1 and VL-GR2 fusions were expressed in *E. coli* and displayed by phage. As shown in FIGS. 10-11, functional heterodimeric ccFv Abus stabilized by the parallel coiled-coil helix were generated. Since the coiled-coil heterodimerization sequences are about half the size of CH1 and CL domains, the ccFv (approximately 35 kDa) is smaller than the conventional Fab fragments (approximately 50 kDa). Because of the small size, the ccFvs and its derivatives are potentially more useful for clinical applications such as tumor and tissue penetration. More efficient expression and display of ccFv is expected. Furthermore, the specific assembly of VH and VL regions due to the pairwise affinity of the unique heterodimerization sequences makes the construction of a robust, vast diverse repertoire of Abs more feasible.

Materials and Methods:

Bacterial and phage strain: *Escherichia coli* TG1 (supE Δ(hsdM-mcrB)5($r_k^{-31}$ $m_k^{-31}$ McrB$^{31}$ )thi Δ(lac-proAB/

F'traD36, LacI<sup>q</sup>Δ(lacZ)M15] was used for plasmid DNA and phage production; KO7 helper phage and HRP-conjugated anti-M13 antibody from Phamersham Pharmacia Biotech; pbluescript SK(+) from Stratagene; Anti-HA antibody from Santa Cruz Biotechnology.

Example 1

Figure 4A:
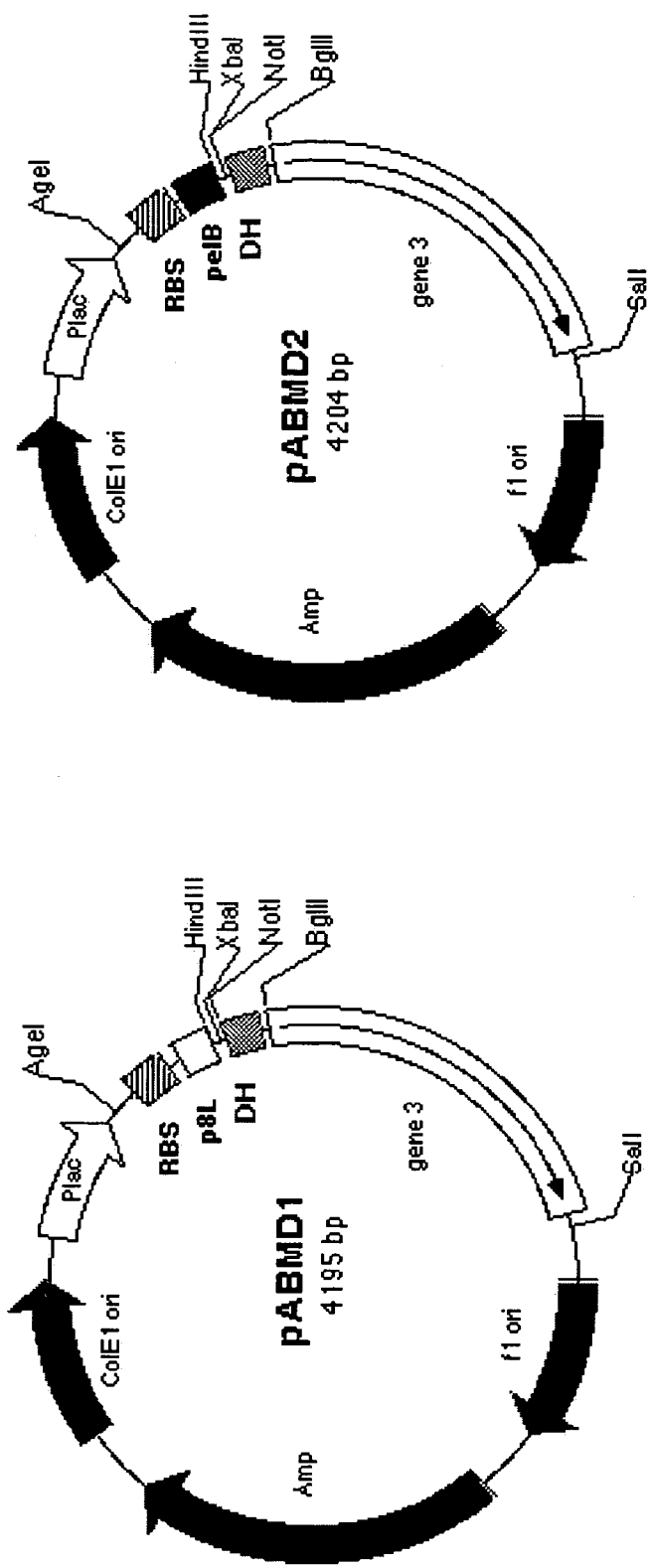
FIG. 4A is a schematic representation of the phagemid vectors pABMD1 and pABMD2 useful for displaying antigen-binding units pABMD1 and ABMD2 were derived from pABMX1 and pABMX2 respectively. They comprise all of the functional elements of pABMX1 and pABMX2 vectors, and pIII gene of a filamentous phage. The pIII gene was inserted immediately adjacent to the 3' end of DH-tag. The lac promoter drives expression of a heterologous sequence as pIII capsid fusion protein, which in turn is displayed on a phage particle upon superinfection of a helper phage such as KO7 (Amersham Pharmacia Biotech) or R408 helper phage (Stratagene). This vector can also be used for soluble protein expression in a non-suppressor bacterial strain.

Vector Construction pABMX1 and pABMX2 Vectors:

The phagemid display vector pABMX1 and pABMX2 were derived from pbluescript SK (+). A unique AgeI restriction site was introduced immediately after lac promoter by PCR-based site-directed mutagenesis with a set of primer (pBS-SKa:5'GGAATTGTGAGCGGATAACAATTTACCG-GTCACACAGGAAACAGCTATGACCATG-3' (SEQ ID NO. 21) and pBs-Skb 5'CATGGTCATAGCTGTTTCCTGT-GTGACCGGTAAATTGTTATCCGCTCACAATTCC-3' (SEQ ID NO. 22), and the XhoI and KpnI sites were deleted by cuffing an blunt end ligation. Afterwards, the synthetic DNA fragments flanked by AgeI site at 5' and BglII/EcoRI sites at 3', containing translation enhance sequence EP from T7 phage gene 10 (TTAACTTTA) (SEQ ID NO. 23), ribosome binding sequence S/D (TAAGGAGG) (SEQ ID NO. 24), fd phage gene8 leader sequence with HindIII site (AT-GAAAAAGTCTTTAGTCCTCAAAGCCTC-CGTAGCCGTTGCTCCCTCGTTCCGAT-GCTAAGCTTCGCT, for pABMX1) (SEQ ID NO. 25), or pelB leader sequence(ATGAAATACCTATTGCCTACG-GCAGCCGCTGGATTGTTATTACTCGCG-GCCCAGCCGGCCATGGCG, for pABMX2) (SEQ ID NO. 26), and HA-(His)$_6$-tag (DHtag) (TATCCATACGACGTAC-CAGACTACGCAGGAGGTCATACACCAT-CATCACCATTAG) (SEQ ID NO. 27), were cloned into modified pbluescript SK (+). The resulting vectors are designated pABMIX1 and PABMX2 (see FIG. #A-B for restriction maps and sequences). Heterologous sequences encoding heteromultimers such a Nsc Abus were further subcloned into these vectors for periplasmic expression.

pABMD1 and pABMD2 vectors:

A PCR-amplified fd gene III (or gene 3) fragment flanked by BglII and SalI sites was inserted into pABMX1 and pABMX2 vectors (see FIG. 4). The heterologous sequence to be displayed can be inserted after the leader sequences. The lac promoter drives expression of the pIII capsid fusion, which in turn can be displayed on phage surface after superinfection by helper phage such as KO7.

Figure 5A:
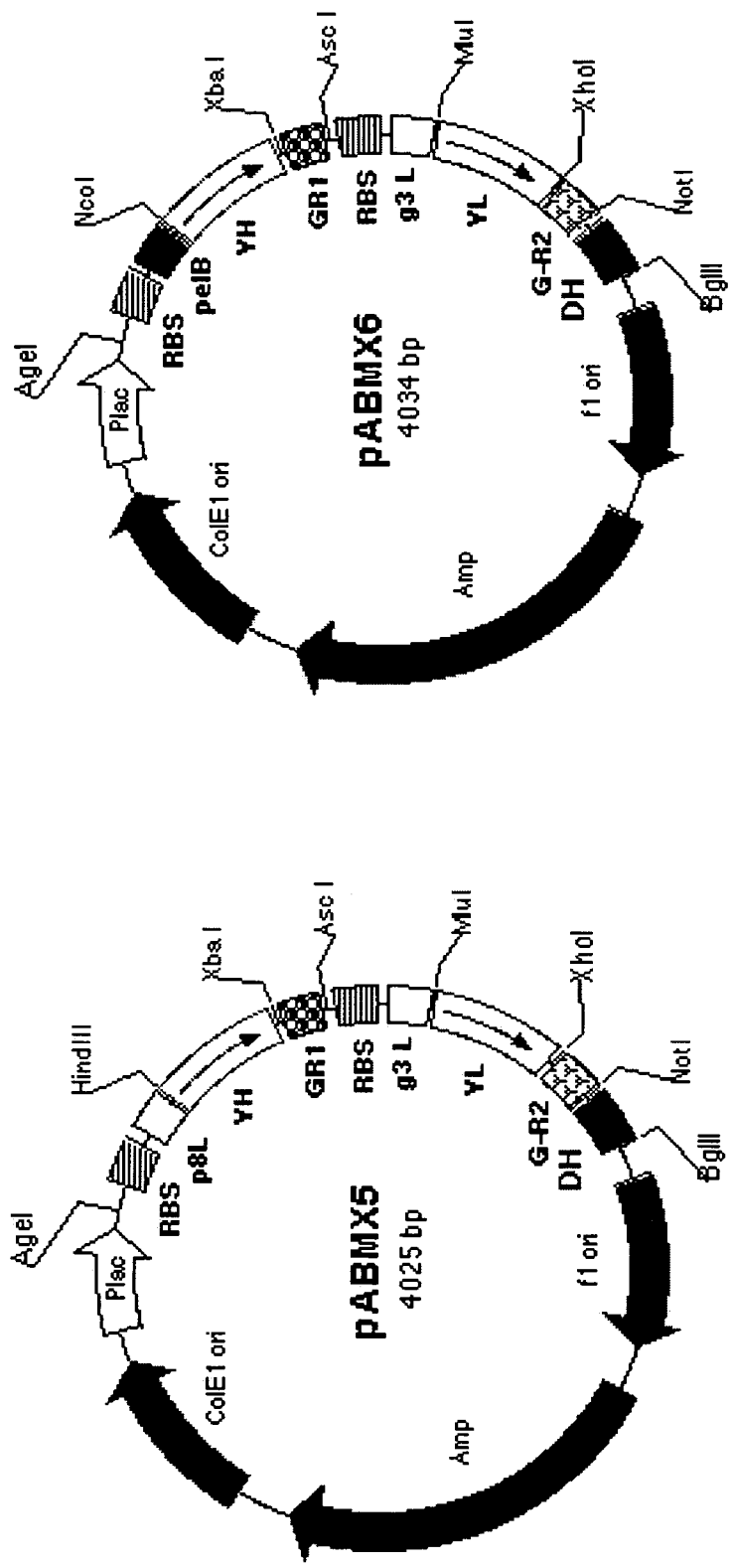
FIG. 5A is a schematic representation of the vectors, pABMX5 and pABMX6. pABMX5 and ABMX6 were derived from pABMX1 and pABMX2 respectively. Different leader sequences were incorporated into pABMX5 and pABMX6. The subcloning sites for insertion of heterologous sequence, e.g. VH gene, also differ in these two vectors. pABMX5 contains the p8 leader, and pABMX6 contains the pe1B leader. Two protein expression cassettes employing the lac promoter were engineered into these two vectors. The first cassette is used to express VH-GR1 (VH-heterodimerization sequence of $GABA_B$ receptor 1) and the second is used to express VL-GR2 (VL-heterodimerization sequence of $GABA_B$ receptor 2). The DH-tag was fused to GR2 domain to facilitate purification of the resulting heterodimers.
Figure 6A:
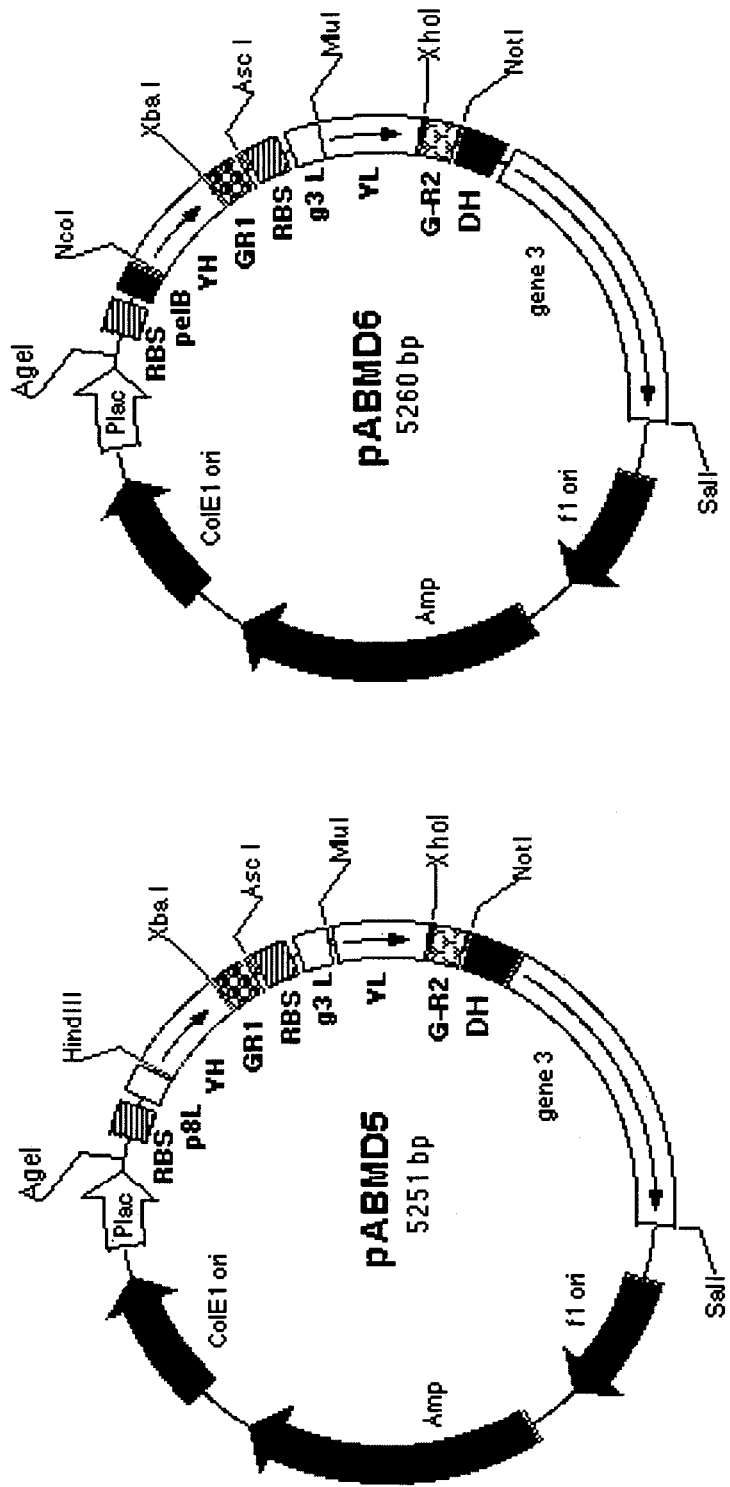
FIG. 6A is a schematic representation of phagemid vectors, pABMD5 and pABMD6, which are useful for expressing and displaying ccFv on a phage particle. pABMD5 and ABMD6 were derived from pABMX5 and pABMX6 respectively. pIII gene derived from the filamentous phage was inserted immediately after DH-tag. The VL-GR2 proteins were linked to pIII capsid protein to facilitate display of the ccFv heterodimer.

PABMX5 and pABMX6 vectors:

These two vectors were derived from pABMX1 and pABMX2. A synthetic DNA fragment flanked by XbaI/AscI site at 5' and M1uI/XhoI/NotI sites at 3', Containing the ribosome binding sequence S/D (TAAGGAGG) (SEQ ID NO. 24) and Gene 3 leaderSequence (ATGAAA AAATTAT-TATTCGCAATTCTTT AGTTGTTC CTT TCTATTCT-CACTCCGCT) (SEQ ID NO. 28), was inserted into pABMX1 and pABMX2 by XbaI/NotI sites. Afterward, the GR1 domain coding sequence (FIG. 2) was subcloned onto Xba/AscI sites, and GR2 domain coding sequence (FIG. 2) was inserted into XhoI/NotI site. Then the VH and VL domain were inserted before GR1 and GR2 sequence respectively. A schematic representation of the vectors pABMX5 and pABMX6 are shown as FIG. 5A. These vectors express two proteins: VH-GR1 and VL-GR2 under one lac promoter.

pABMD5 and pABMD6 vector:

The ccFv DNA fragments from vector pABMX5 and pABMX6 vectors were subcloning into pABMD1 and pABMD2 to yield vectors pABMD5 and pABMD6 (see FIG. 6A-B for restriction maps and sequences). These vectors express two proteins: VH-GR1 and VL-GR2-pIII fusions. The expressed VH-GR1 and VL-GR2-pIII fusions are secreted into periplasmic space, where dimerization may take place via the coiled-coil domain heterodimerization. The assembled Abu is then displayed on phage surface upon superinfection of helper phages such as KO7.

Example 2

Expression of Functional ccFv

Figure 10A:
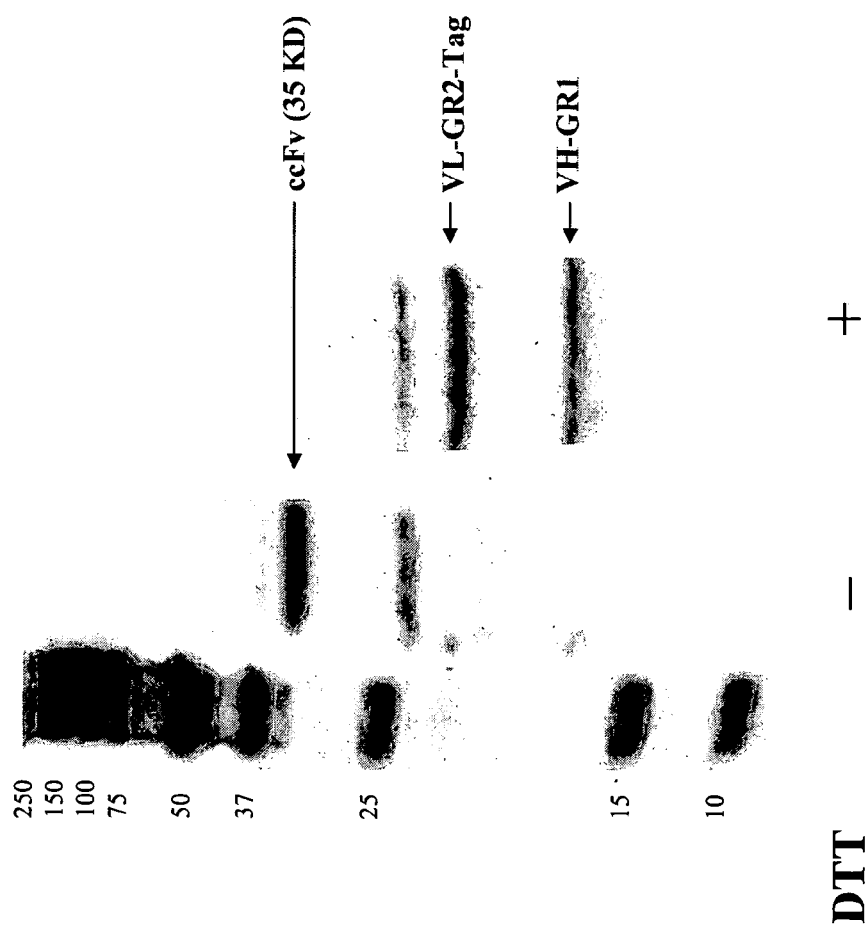
FIG. 10A depicts the results of SDS-PAGE analysis of AM1-ccFv expressed in *E. coli* under reducing and non-reducing condition. The results demonstrate successful expression and assembly of heterodimeric ccFv in *E. coli*.

Antibody variable domains from antibody AM1 were subcloned into pABMX6 vector to expression ccFv fragment. The vector was then introduced into either TG1 cells or BL21 cells. The transformed bacteria in 500 ml 2xYT containing approximately 100 τg/ml carbenicillin and 0.1% glucose from a single colony was grew to $OD_{600}=0.7$ (approximately), at 37° C. 1 mM of IPTG was added for 4 hrs inductions at 30° C. The bacterial pellet was collected for periplasmic and osmotic shock preparation. The pellet was resuspended in 12.5 ml PPB buffer (200 mg/ml sucrose, 1 mM EDTA, 30 mM Tris-HCl, pH 8.0) with 1.25 ml protease inhibitor cocktail from Sigma, and put on ice for 20 min. The supernatant was collected by spinning. The pellet was resuspended in 5 mM $MgSO_4$, and incubated on ice for 20 min. The $MgSO_4$ and PPB supernatants were combined, and dialyzed against PBS. After loading to a 1 ml of Ni-NTA column, the His-tag proteins were purified by 350 mM imidozole elution. FIG. 10A shows that the purified ccFv has an electrophoretic mobility of 35 kDa on a non-reducing gel. When analyzed under reducing condition, two subunits corresponding to VL and VH were observed. The upper band was confirmed as VL-His-tag fusion by Western blot analysis.

Figure 10B:
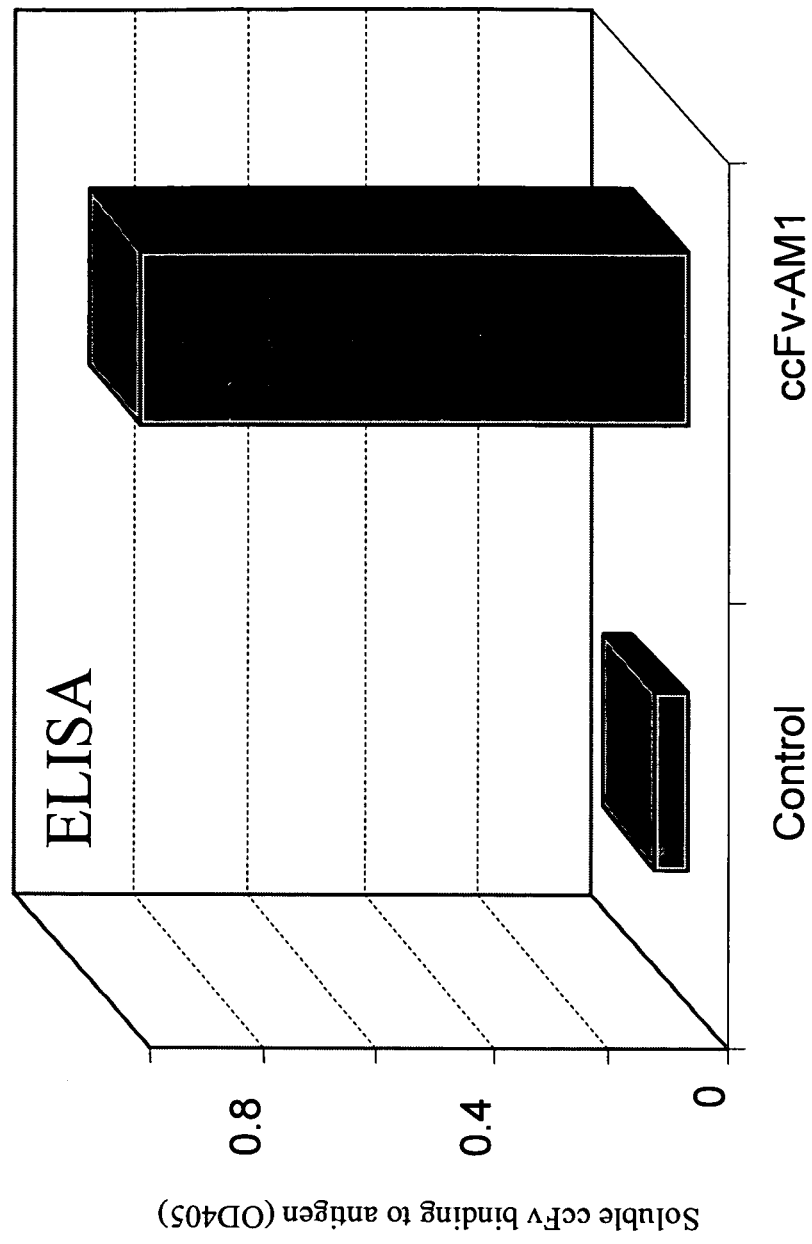
FIG. 10B depicts the results of an ELISA assay using soluble AM1-ccFv expressed in *E. coli*. The results indicate successful assembly of functional ccFv with expected binding specificity to its corresponding antigen.

To measure the binding specificity of soluble AM1-ccFv, ELISA assay was carried out. The AM1 antigens (0.2-1 ug/well) were coated on ELISA plates for overnight at 4° C. After 5% milk/PBS blocking, antibody solution in 5% milk/PBS was added to the ELISA plate, and incubated for 1-2 hr at room temperature. The unbound Abus were washed out. FIG. 10B shows specific binding of AM1-ccFv to its antigen. The control contains 5% milk in PBS. This result confirms the assembly of functional ccFv by the coiled-coil $GABA_B$ R1/R2 heterodimerization sequences.

Example 3

Display of Functional ccFv

Display of antibody by a genetic package is a powerful tool to enrich and isolate specific Abu from large libraries. To analyze whether ccFv can be utilized in a phage display system, we have constructed a phagemid vector by subcloning ccFv gene of AM1 antibody into pABMD6 vector. TG1 cells carrying the phagemid vectors were superinfected by KO7 helper phage. The infected TG1 cells were grown in 2xYT/Amp/Kan at 30° C. overnight. The phagemid particles were precipitated by PEG/NaCl from culture supernatants twice, and resuspended in PBS. The antibody displayed on phage was detected by antigen binding activity via phage ELISA assay. Briefly, the antigens were first coated on ELISA plates. After 5% milk/PBS blocking, the phage solution was added to ELISA plates. The phage bound to antigen was detected by incubation with HRP-conjugated anti-M13 antibody. The substrate ABTS [2,2'Azino-bis(3-ethylbenzthiazoline-6-sulfonic acid)] was used for measurement of HRP activity. The anti-HA tag antibody was also used to detect the proteins displayed on phage particle. The anti-HA antibody was coated on 96-well plates (2 ug/each well). The phages bound to anti-HA antibody coated on-ELISA plate were detected by HRP-conjugated anti-M13 antibody.

Figure 11A:
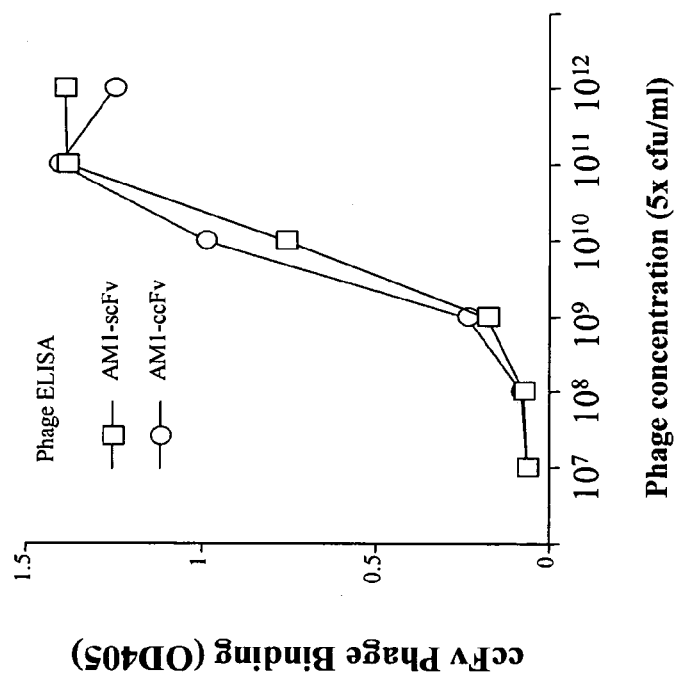
FIG. 11A depicts a comparison of the antigen binding capability of AM1-ccFv expressing phage and that of AM1-scFv expressing phage. The results demonstrate that the phage particles displaying the AM1-ccFv fragments exhibit slightly higher binding capability than the phages displaying conventional scFv fragments.

The single-chain antibody phage was also prepared for comparing the ccFv and scFv phage-display. As shown in FIG. 11A-B, the binding capability of ccFv phages is comparable to that of the conventional scFv phages. For certain ccFv expressing phages, their binding capability is almost one order of magnitude higher than phages expressing conventional scFv (FIG. 11B). Thus, ccFv is a functional Abu even when displayed on a phage particle.

Expression of Single-Chain Antigen-Binding Units:

Example 4

Expression of Conventional scFv

Figure 8:
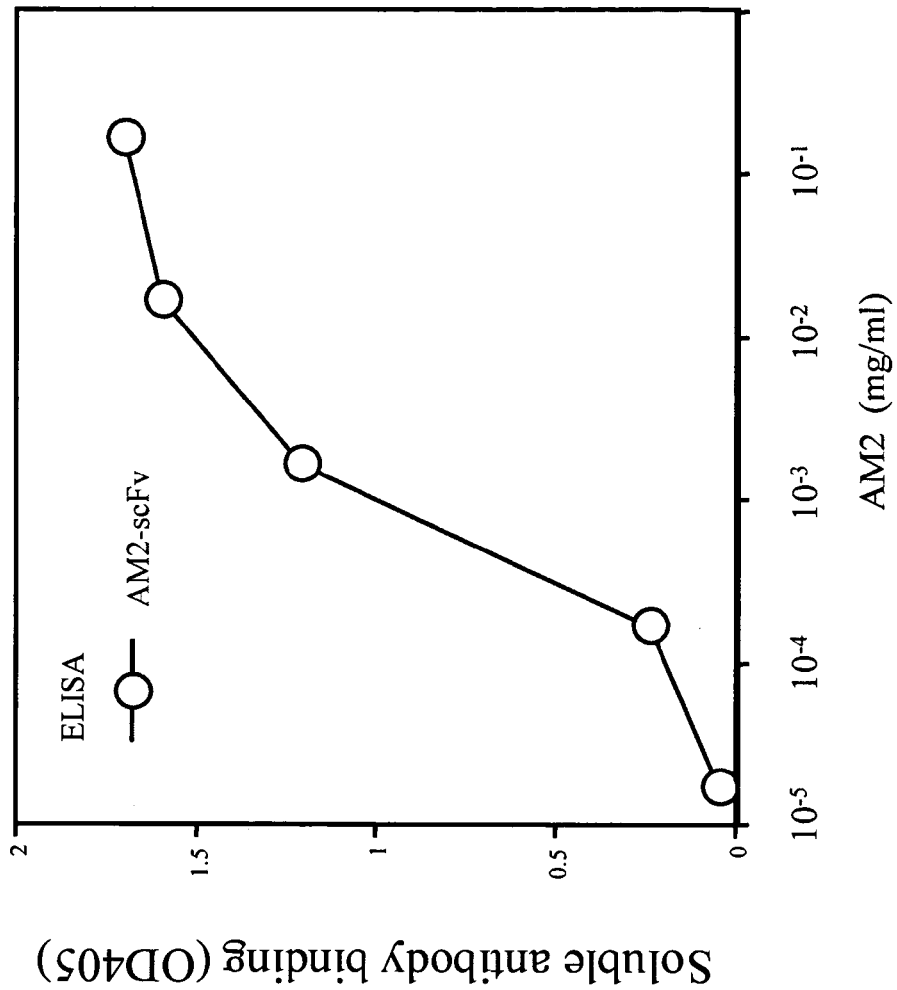
FIG. 8 depicts the results of an ELISA assay using AM2-scFv fragments that were expressed by the pABMX1 vector. The results show a dose-dependent AM2-scFv binding to its antigen AM2.

The AM2-scFv was subcloning into soluble expression vector pABMX1 at the HindIII/NotI sites. The periplasmic preparation was carried out as outlined above. A 30 kDa antibody protein purified from NI-NTA column was confirmed by SDS-PAGE analysis, and was tested for its antigen-binding specificity using ELISA. The AM2 antigens were first coated onto ELISA plates at a concentration of 0.2 ug/well. Different amounts of AM2-scFv fragments were incubated with the antigen. Bound AM2-svFv fragments were detected by the anti-HA-tag antibody. The experiment revealed a dose-dependent binding of AM2-scFv to its the AM2 antigen (FIG. 8).

Example 5

Display of Conventional scFv on Phage

Figure 9:
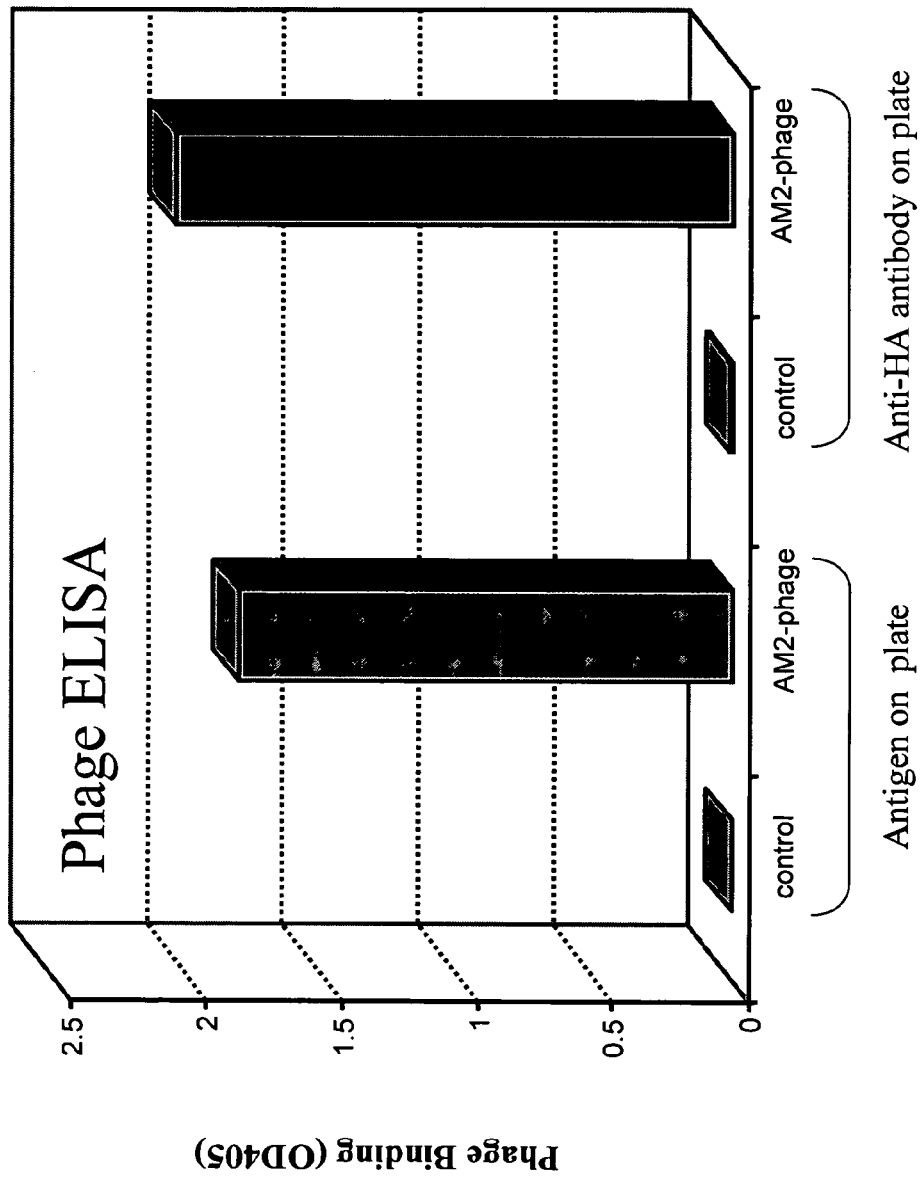
FIG. 9 depicts the results of an ELISA assay using AM2-scFv fragments that were displayed on phage particles. The results demonstrate the assembly of functional scFv fragments on phage particles using the phagemid vector pABMD1.

The AM2-scFv fragment was first subcloning into phagemid vector pABMD1 at the HindIII/NotI sites. TG1 cells carrying this phagemid vector were infected by the helper phage KO7. The phages were purified from the supernatants. Phage ELISA assay was subsequently performed to detect AM2-scFv displayed on the phage particles. Because the coat pIII gene is tagged with HA-tag, the fusion can be detected with anti-HA antibodies. ELISA assay using AM2 antigen and anti-HA antibodies confirmed that the displayed scFv was capable of specifically binding to the corresponding antigens (FIG. 9). The control involves phages displaying unrelated antibodies that are not HA tagged.

Expression of the Subject Antigen-Binding Units in Eukaryotic Cells:

Example 6

Expression of ccFv in Yeast

The yeast vector pAMEX7 carrying both VL and VH sequences that are linked to the subject heterodimerization sequences is constructed. Competent yeast cells, e.g. AH109 cell, are prepared and transformed with pAMEX7 vectors according to any method known in the art. The transformed yeast cells are cultured under conditions suitable for protein expression. Such conditions are well known to artisans in the field and hence are not detailed herein. The expressed ccFv Abus are harvested using conventional methods known in the art and/or procedures described herein. The antigen binding capability of the harvest ccFv are determined by ELISA according to the protocols described above.

What is claimed is:

1. A recombinant polynucleotide comprising a coding sequence that encodes a light (L) chain polypeptide of a non-single-chain antigen-binding unit, wherein the non-single-chain antigen-binding unit comprises: (a) the encoded light (L) chain polypeptide having a light (L) chain variable region fused in-frame to a first heterodimerization polypeptide and (b) a heavy (H) chain polypeptide having a heavy (H) chain variable region fused in-frame to a second heterodimerization polypeptide wherein the L chain and the H chain polypeptides dimerize via pairwise affinity of the first and second heterodimerization polypeptides, said first and second heterodimerization polypeptides comprising heterodimeric receptor polypeptides that mediate heterodimerization.

2. A recombinant polynucleotide comprising a coding sequence that encodes a heavy (H) chain polypeptide of a non-single-chain antigen-binding unit, wherein the non-single-chain antigen-binding unit comprises: (a) a light (L) chain polypeptide comprising a light (L) chain variable region fused in-frame to a first heterodimerization polypeptide and (b) the encoded heavy (H) chain polypeptide comprising a heavy (H) chain variable region fused in-frame to a second heterodimerization polypeptide wherein the L chain and the H chain polypeptides dimerize via pairwise affinity of the first and second heterodimerization polypeptides, said first and second heterodimerization polypeptides comprising heterodimeric receptor sequences that mediate heterodimerization.

3. A recombinant polynucleotide comprising a first coding sequence that encodes the L chain polypeptide of claim 1, and a second coding sequence that encodes the H chain polypeptide of claim 2, wherein the L chain and the H chain polypeptides dimerize via pairwise affinity of the first and second heterodimerization polypeptides; and further wherein at least one of the heterodimerization polypeptides is essentially incapable of forming a homodimer under physiological buffer conditions and/or at physiological body temperatures.

4. A vector comprising the recombinant polynucleotide of claim 1, or 2.

5. The vector of claim 4, wherein the vector is an expression vector.

6. The vector of claim 4, wherein the vector is a phage display vector.

7. A selectable library of expression vectors encoding a repertoire of antigen binding units, comprising more than one vector of claim 4.

8. The selectable library of claim 7, wherein the vector is a phage display vector.

9. An isolated host cell comprising the vector of claim 4.

10. The isolated host cell of claim 9, wherein the recombinant polynucleotide encoding the L chain polypeptide and the polynucleotide encoding the H chain polypeptide, are present in a single vector.

11. The isolated host cell of claim 9, wherein the recombinant polynucleotide encoding the L chain polypeptide and the polynucleotide encoding the H chain polypeptide, are present in separate vectors.

12. The isolated host cell of claim 9, wherein the host cell is a eukaryotic cell.

13. The isolated host cell of claim 9, wherein the host cell is a prokaryotic cell.

14. A method of producing a non-single-chain antigen-binding unit, comprising: (a) expressing in a host cell a first recombinant polynucleotide encoding a light (L) chain polypeptide comprising a light (L) chain variable region fused in-frame to a first heterodimerization polypeptide, and a second recombinant polynucleotide encoding a heavy (H) chain polypeptide comprising a heavy (H) chain variable region fused in-frame to a second heterodimerization polypeptide; wherein the L chain and the H chain polypeptides dimerize via pairwise affinity of the first and second heterodimerization polypeptides and optionally (b) isolating the antigen-binding unit expressed in the host cell.

15. The method of claim 14, wherein the non-single-chain antigen-binding expressed in step (a) is displayed on surface of the host cell.

16. The method of claim 14, wherein the non-single-chain antigen-binding expressed in step (a) is displayed on a phage particle.

17. The method of claim 14, wherein the host cell is a eukaryotic cell.

18. The method of claim 14, wherein the host cell is a prokaryotic cell.

19. The method of 14, wherein the first and second heterodimerization polypeptides form a coiled-coil dimer.

20. The method of claim 14, wherein the L chain and the H chain polypeptides dimerize via non-covalent pairwise affinity.

21. The method of claim 19, wherein the L chain polypeptide further comprises a flexon that is flanked by the L chain variable region and the first heterodimerization polypeptide.

22. The method of claim 19, wherein the H chain polypeptide further comprises a flexon that is flanked by the H chain variable region and the second heterodimerization polypeptide.

23. The method of claim 19, wherein both the first and the second heterodimerization polypeptides are linked to at least one cysteine residue.

24. The method of claim 19, wherein the non-single-chain antigen-binding unit is multivalent.

25. The method of claim 19, wherein the non-single-chain antigen-binding unit is multispecific.

26. The method of claim 25, wherein the non-single-chain antigen-binding unit is bispecific.

27. The method of claim 25, wherein the non-single-chain antigen-binding unit is trispecific.

28. The method of claim 14, wherein the light (L) chain variable region is human.

29. The method of claim 14, wherein the heavy (H) chain variable region is human.

30. The method of claim 14, wherein the non-single-chain antigen-binding unit exhibits an apparent binding affinity at least one order of magnitude higher than that of a single-chain antigen-binding unit (scFv) that is stabilized by a peptide linker.

31. A kit comprising a vector of claim 4 in suitable packaging.

* * * * *

SEQUENCE LISTING

```
<160> NUMBER OF SEQ ID NOS: 30

<210> SEQ ID NO 1
<211> LENGTH: 146
<212> TYPE: DNA
<213> ORGANISM: Homo sapiens
<220> FEATURE:
<221> NAME/KEY: CDS
<222> LOCATION: (1)...(132)

<400> SEQUENCE: 1 tct aga ggt gga gga ggt gag gag aag tcc cgg ctg ttg gag aag gag      48
Ser Arg Gly Gly Gly Gly Glu Glu Lys Ser Arg Leu Leu Glu Lys Glu
  1               5                  10                  15 aac cgt gaa ctg gaa aag atc att gct gag aaa gag gag cgt gtc tct      96
Asn Arg Glu Leu Glu Lys Ile Ile Ala Glu Lys Glu Glu Arg Val Ser
             20                  25                  30 gaa ctg cgc cat caa ctc cag tct gta gga ggt tgt taatagggcg           142
Glu Leu Arg His Gln Leu Gln Ser Val Gly Gly Cys
         35                  40 cgcc                                                                 146

<210> SEQ ID NO 2
<211> LENGTH: 44
<212> TYPE: PRT
<213> ORGANISM: Homo sapiens
```

-continued

<400> SEQUENCE: 2

Ser Arg Gly Gly Gly Gly Glu Glu Lys Ser Arg Leu Leu Glu Lys Glu
1               5                   10                  15

Asn Arg Glu Leu Glu Lys Ile Ile Ala Glu Lys Glu Arg Val Ser
            20                  25                  30

Glu Leu Arg His Gln Leu Gln Ser Val Gly Gly Cys
        35                  40

<210> SEQ ID NO 3
<211> LENGTH: 140
<212> TYPE: DNA
<213> ORGANISM: Homo sapiens
<220> FEATURE:
<221> NAME/KEY: CDS
<222> LOCATION: (1)...(140)

<400> SEQUENCE: 3 tct cga gga ggt ggt gga aca tcc cgc ctg gag ggc cta cag tca gaa      48
Ser Arg Gly Gly Gly Gly Thr Ser Arg Leu Glu Gly Leu Gln Ser Glu
1               5                   10                  15 aac cat cgc ctg cga atg aag atc aca gag ctg gat aaa gac ttg gaa      96
Asn His Arg Leu Arg Met Lys Ile Thr Glu Leu Asp Lys Asp Leu Glu
            20                  25                  30 gag gtc acc atg cag ctg cag gac gtc gga ggt tgc gcg gcc gc          140
Glu Val Thr Met Gln Leu Gln Asp Val Gly Gly Cys Ala Ala
        35                  40                  45

<210> SEQ ID NO 4
<211> LENGTH: 46
<212> TYPE: PRT
<213> ORGANISM: Homo sapiens

<400> SEQUENCE: 4

Ser Arg Gly Gly Gly Gly Thr Ser Arg Leu Glu Gly Leu Gln Ser Glu
1               5                   10                  15

His Arg Leu Arg Met Lys Ile Thr Glu Leu Asp Lys Asp Leu Glu Glu
            20                  25                  30

Val Thr Met Gln Leu Gln Asp Val Gly Gly Cys Ala Ala Ala
        35                  40                  45

<210> SEQ ID NO 5
<211> LENGTH: 203
<212> TYPE: DNA
<213> ORGANISM: Artificial Sequence
<220> FEATURE:
<223> OTHER INFORMATION: Bluescript vector
<220> FEATURE:
<223> OTHER INFORMATION: Bluescript vector

<400> SEQUENCE: 5 aat tgt gag cgg ata aca att tac cgg ttc ttt taa ctt tag taa gga      48 gga att aaa aaa tga aaa agt ctt tag tcc tca aag cct ccg tag ccg      96 ttg cta ccc tcg ttc cga tgc taa gct tcg ctt cta gag cgg ccg ctt     144 atc cat acg acg tac cag act acg cag gag gtc atc acc atc atc acc     192 att aga gat ct                                                       203

<210> SEQ ID NO 6
<211> LENGTH: 45
<212> TYPE: PRT
<213> ORGANISM: Artificial Sequence -continued
<220> FEATURE:
<223> OTHER INFORMATION: BlueScript

<400> SEQUENCE: 6

Met Lys Lys Ser Leu Val Leu Lys Ala Ser Val Ala Val Ala Thr Leu
1               5                   10                  15

Val Pro Met Leu Ser Phe Ala Ser Arg Ala Ala Ala Tyr Pro Tyr Asp
            20                  25                  30

Val Pro Asp Tyr Ala Gly Gly His His His His His
        35                  40                  45

<210> SEQ ID NO 7
<211> LENGTH: 212
<212> TYPE: DNA
<213> ORGANISM: Artificial Sequence
<220> FEATURE:
<223> OTHER INFORMATION: Bluescript vector
<220> FEATURE:
<223> OTHER INFORMATION: Bluescript vector

<400> SEQUENCE: 7 aat tgt gag cgg ata aca att tac cgg ttc ttt taa ctt tag taa gga        48 gga att aaa aaa tga aat acc tat tgc cta cgg cag ccg ctg gat tgt        96 tat tac tcg cgg ccc agc cgg cca tgg cgg ccc tgc agg cct cta gag       144 cgg ccg ctt atc cat acg acg tac cag act acg cag gag gtc atc acc       192 atc atc acc att aga gat ct                                            212

<210> SEQ ID NO 8
<211> LENGTH: 48
<212> TYPE: PRT
<213> ORGANISM: Artificial Sequence
<220> FEATURE:
<223> OTHER INFORMATION: BlueScript

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala Ala Leu Gln Ala Ser Arg Ala Ala Ala Tyr
            20                  25                  30

Pro Tyr Asp Val Pro Asp Tyr Ala Gly Gly His His His His His
        35                  40                  45

<210> SEQ ID NO 9
<211> LENGTH: 272
<212> TYPE: DNA
<213> ORGANISM: Artificial Sequence
<220> FEATURE:
<223> OTHER INFORMATION: Bluescript vector

<400> SEQUENCE: 9
aattgtgagc ggataacaat ttaccggttc ttttaacttt agtaaggagg aattaaaaaa        60
tgaaaaagtc tttagtcctc aaagcctccg tagccgttgc taccctcgtt ccgatgctaa       120
gcttcgcttc tagagcggcc gcttatccat acgacgtacc agactacgca ggaggtcatc       180
accatcatca ccattagaga tctggaggcg gtactgttga agttgtttta gcaaaagcta       240
acatactgcg taataaggag tcttaagtcg ac                                     272

<210> SEQ ID NO 10
<211> LENGTH: 67
<212> TYPE: PRT

<213> ORGANISM: Artificial Sequence
<220> FEATURE:
<223> OTHER INFORMATION: BlueScript vector

<400> SEQUENCE: 10

```
Met Lys Lys Ser Leu Val Leu Lys Ala Ser Val Ala Val Ala Thr Leu
 1               5                  10                  15
Val Pro Met Leu Ser Phe Ala Ser Arg Ala Ala Ala Tyr Pro Tyr Asp
            20                  25                  30
Val Pro Asp Tyr Ala Gly Gly His His His His His Arg Ser Gly
        35                  40                  45
Gly Gly Thr Val Glu Ser Cys Leu Ala Lys Ala Asn Ile Leu Arg Asn
    50                  55                  60
Lys Glu Ser
65
```

<210> SEQ ID NO 11
<211> LENGTH: 281
<212> TYPE: DNA
<213> ORGANISM: Artificial Sequence
<220> FEATURE:
<223> OTHER INFORMATION: Bluescript vector

<400> SEQUENCE: 11

```
aat tgt gag cgg ata aca att tac cgg ttc ttt taa ctt tag taa gga        48
gga att aaa aaa tga aat acc tat tgc cta cgg cag ccg ctg gat tgt        96
tat tac tcg cgg ccc agc cgg cca tgg cgg ccc tgc agg cct cta gag       144
cgg ccg ctt atc cat acg acg tac cag act acg cag gag gtc atc acc       192
atc atc acc att aga gat ctg gag gcg gta ctg ttg aaa gtt gtt tag       240
caa a ag cta aca tac tgc gta ata agg agt ctt aag tcg ac              281
```

<210> SEQ ID NO 12
<211> LENGTH: 70
<212> TYPE: PRT
<213> ORGANISM: Artificial Sequence
<220> FEATURE:
<223> OTHER INFORMATION: BlueScript vector

<400> SEQUENCE: 12

```
Met Lys Tyr Leu Leu Pro Thr Ala Ala Ala Gly Leu Leu Leu Leu Ala
 1               5                  10                  15
Ala Gln Pro Ala Met Ala Ala Leu Gln Ala Ser Arg Ala Ala Ala Tyr
            20                  25                  30
Pro Tyr Asp Val Pro Asp Tyr Ala Gly Gly His His His His His
        35                  40                  45
Arg Ser Gly Gly Gly Thr Val Glu Ser Cys Leu Ala Lys Ala Asn Ile
    50                  55                  60
Leu Arg Asn Lys Glu Ser
65                  70
```

<210> SEQ ID NO 13
<211> LENGTH: 501
<212> TYPE: DNA
<213> ORGANISM: Artificial Sequence
<220> FEATURE:
<221> NAME/KEY: CDS
<222> LOCATION: (1)...(501)
<223> OTHER INFORMATION: Bluescript vector
<220> FEATURE:
<223> OTHER INFORMATION: Bluescript vector

<400> SEQUENCE: 13

```
atg aaa aag tct tta gtc ctc aaa gcc tcc gta gcc gtt gct acc ctc      48
Met Lys Lys Ser Leu Val Leu Lys Ala Ser Val Ala Val Ala Thr Leu
 1               5                  10                  15 gtt ccg atg cta agc ttc gct tct aga ggt gga ggt gag gag aag          96
Val Pro Met Leu Ser Phe Ala Ser Arg Gly Gly Gly Glu Glu Lys
             20                  25                  30 tcc cgg ctg ttg gag aag gag aac cgt gaa ctg gaa aag atc att gct     144
Ser Arg Leu Leu Glu Lys Glu Asn Arg Glu Leu Glu Lys Ile Ile Ala
         35                  40                  45 gag aaa gag gag cgt gtc tct gaa ctg cgc cat caa ctc cag tct gta     192
Glu Lys Glu Glu Arg Val Ser Glu Leu Arg His Gln Leu Gln Ser Val
 50                  55                  60 gga ggt tgt taa tag ggc gcg cca caa ttt cac agt aag gag gtt taa     240
Gly Gly Cys  *   *  Gly Ala Pro Gln Phe His Ser Lys Glu Val  *
 65                      70                  75 ctt atg aaa aaa tta tta ttc gca att cct tta gtt gtt cct ttc tat     288
Leu Met Lys Lys Leu Leu Phe Ala Ile Pro Leu Val Val Pro Phe Tyr
             80                  85                  90 tct cac tcc gct acg cgt tct cga gga ggt ggt gga aca tcc cgc ctg     336
Ser His Ser Ala Thr Arg Ser Arg Gly Gly Gly Gly Thr Ser Arg Leu
 95                  100                 105 gag ggc cta cag tca gaa aac cat cgc ctg cga atg aag atc aca gag     384
Glu Gly Leu Gln Ser Glu Asn His Arg Leu Arg Met Lys Ile Thr Glu
110             115                 120                 125 ctg gat aaa gac ttg gaa gag gtc acc atg cag ctg cag gac gtc gga     432
Leu Asp Lys Asp Leu Glu Glu Val Thr Met Gln Leu Gln Asp Val Gly
             130                 135                 140 ggt tgc gcg gcc gct tat cca tac gac gta cca gac tac gca gga ggt     480
Gly Cys Ala Ala Ala Tyr Pro Tyr Asp Val Pro Asp Tyr Ala Gly Gly
                 145                 150                 155 cat cac cat cat cac cat tag                                          501
His His His His His His  *
        160
```

<210> SEQ ID NO 14
<211> LENGTH: 163
<212> TYPE: PRT
<213> ORGANISM: Artificial Sequence
<220> FEATURE:
<223> OTHER INFORMATION: BlueScript vector

<400> SEQUENCE: 14

```
Met Lys Lys Ser Leu Val Leu Lys Ala Ser Val Ala Val Ala Thr Leu
 1               5                  10                  15

Val Pro Met Leu Ser Phe Ala Ser Arg Gly Gly Gly Glu Glu Lys
             20                  25                  30

Ser Arg Leu Leu Glu Lys Glu Asn Arg Glu Leu Glu Lys Ile Ile Ala
         35                  40                  45

Glu Lys Glu Glu Arg Val Ser Glu Leu Arg His Gln Leu Gln Ser Val
 50                  55                  60

Gly Gly Cys Gly Ala Pro Gln Phe His Ser Lys Glu Val Leu Met Lys
 65                  70                  75                  80

Lys Leu Leu Phe Ala Ile Pro Leu Val Val Pro Phe Tyr Ser His Ser
             85                  90                  95

Ala Thr Arg Ser Arg Gly Gly Gly Gly Thr Ser Arg Leu Glu Gly Leu
        100                 105                 110

Gln Ser Glu Asn His Arg Leu Arg Met Lys Ile Thr Glu Leu Asp Lys
```

```
                    115                 120                 125
Asp Leu Glu Glu Val Thr Met Gln Leu Gln Asp Val Gly Gly Cys Ala
    130                 135                 140

Ala Ala Tyr Pro Tyr Asp Val Pro Asp Tyr Ala Gly Gly His His
145                 150                 155                 160

His His His

<210> SEQ ID NO 15
<211> LENGTH: 498
<212> TYPE: DNA
<213> ORGANISM: Artificial Sequence
<220> FEATURE:
<221> NAME/KEY: CDS
<222> LOCATION: (1)...(498)
<223> OTHER INFORMATION: Bluescript vector
<220> FEATURE:
<223> OTHER INFORMATION: Bluescript vector

<400> SEQUENCE: 15 atg aaa tac cta ttg cct acg gca gcc gct gga ttg tta tta ctc gcg      48
Met Lys Tyr Leu Leu Pro Thr Ala Ala Ala Gly Leu Leu Leu Leu Ala
1               5                   10                  15 gcc cag ccg gcc atg gcg tct aga ggt gga gga ggt gag gag aag tcc      96
Ala Gln Pro Ala Met Ala Ser Arg Gly Gly Gly Gly Glu Glu Lys Ser
            20                  25                  30 cgg ctg ttg gag aag gag aac cgt gaa ctg gaa aag atc att gct gag     144
Arg Leu Leu Glu Lys Glu Asn Arg Glu Leu Glu Lys Ile Ile Ala Glu
        35                  40                  45 aaa gag gag cgt gtc tct gaa ctg cgc cat caa ctc cag tct gta gga     192
Lys Glu Glu Arg Val Ser Glu Leu Arg His Gln Leu Gln Ser Val Gly
50                  55                  60 ggt tgt taa tag ggc gcg cca caa ttt cac agt aag gag gtt taa ctt     240
Gly Cys  *   *  Gly Ala Pro Gln Phe His Ser Lys Glu Val  *  Leu
65                  70                  75 atg aaa aaa tta tta ttc gca att cct tta gtt gtt cct ttc tat tct     288
Met Lys Lys Leu Leu Phe Ala Ile Pro Leu Val Val Pro Phe Tyr Ser
        80                  85                  90 cac tcc gct acg cgt tct cga gga ggt ggt gga aca tcc cgc ctg gag     336
His Ser Ala Thr Arg Ser Arg Gly Gly Gly Gly Thr Ser Arg Leu Glu
    95                  100                 105 ggc cta cag tca gaa aac cat cgc ctg cga atg aag atc aca gag ctg     384
Gly Leu Gln Ser Glu Asn His Arg Leu Arg Met Lys Ile Thr Glu Leu
110                 115                 120                 125 gat aaa gac ttg gaa gag gtc acc atg cag ctg cag gac gtc gga ggt     432
Asp Lys Asp Leu Glu Glu Val Thr Met Gln Leu Gln Asp Val Gly Gly
            130                 135                 140 tgc gcg gcc gct tat cca tac gac gta cca gac tac gca gga ggt cat     480
Cys Ala Ala Ala Tyr Pro Tyr Asp Val Pro Asp Tyr Ala Gly Gly His
                145                 150                 155 cac cat cat cac cat tag                                              498
His His His His His  *
        160

<210> SEQ ID NO 16
<211> LENGTH: 162
<212> TYPE: PRT
<213> ORGANISM: Artificial Sequence
<220> FEATURE:
<223> OTHER INFORMATION: Bluescript vector

<400> SEQUENCE: 16

Met Lys Tyr Leu Leu Pro Thr Ala Ala Ala Gly Leu Leu Leu Leu Ala
```

-continued

```
              1               5                  10                 15
            Ala Gln Pro Ala Met Ala Ser Arg Gly Gly Gly Glu Glu Lys Ser
                            20                 25                 30

Arg Leu Leu Glu Lys Glu Asn Arg Glu Leu Glu Lys Ile Ile Ala Glu
                        35                 40                 45

Lys Glu Glu Arg Val Ser Glu Leu Arg His Gln Leu Gln Ser Val Gly
                    50                 55                 60

Gly Cys Gly Ala Pro Gln Phe His Ser Lys Glu Val Leu Met Lys Lys
            65                 70                 75                 80

Leu Leu Phe Ala Ile Pro Leu Val Val Pro Phe Tyr Ser His Ser Ala
                            85                 90                 95

Thr Arg Ser Arg Gly Gly Gly Thr Ser Arg Leu Glu Gly Leu Gln
                        100                105                110

Ser Glu Asn His Arg Leu Arg Met Lys Ile Thr Glu Leu Asp Lys Asp
                    115                120                125

Leu Glu Glu Val Thr Met Gln Leu Gln Asp Val Gly Gly Cys Ala Ala
                    130                135                140

Ala Tyr Pro Tyr Asp Val Pro Asp Tyr Ala Gly Gly His His His
            145                150                155                160

His His
```

<210> SEQ ID NO 17
<211> LENGTH: 552
<212> TYPE: DNA
<213> ORGANISM: Artificial Sequence
<220> FEATURE:
<221> NAME/KEY: CDS
<222> LOCATION: (1)...(543)
<223> OTHER INFORMATION: Bluescript vector
<220> FEATURE:
<223> OTHER INFORMATION: Bluescript primer

<400> SEQUENCE: 17

```
atg aaa aag tct tta gtc ctc aaa gcc tcc gta gcc gtt gct acc ctc      48
Met Lys Lys Ser Leu Val Leu Lys Ala Ser Val Ala Val Ala Thr Leu
 1               5                  10                  15 gtt ccg atg cta agc ttc gct tct aga ggt gga gga ggt gag gag aag      96
Val Pro Met Leu Ser Phe Ala Ser Arg Gly Gly Gly Gly Glu Glu Lys
             20                  25                  30 tcc cgg ctg ttg gag aag gag aac cgt gaa ctg gaa aag atc att gct     144
Ser Arg Leu Leu Glu Lys Glu Asn Arg Glu Leu Glu Lys Ile Ile Ala
         35                  40                  45 gag aaa gag gag cgt gtc tct gaa ctg cgc cat caa ctc cag tct gta     192
Glu Lys Glu Glu Arg Val Ser Glu Leu Arg His Gln Leu Gln Ser Val
     50                  55                  60 gga ggt tgt taa tag ggc gcg cca caa ttt cac agt aag gag gtt taa     240
Gly Gly Cys  *   *  Gly Ala Pro Gln Phe His Ser Lys Glu Val  *
 65                  70                  75 ctt atg aaa aaa tta tta ttc gca att cct tta gtt gtt cct ttc tat     288
Leu Met Lys Lys Leu Leu Phe Ala Ile Pro Leu Val Val Pro Phe Tyr
             80                  85                  90 tct cac tcc gct acg cgt tct cga gga ggt ggt gga aca tcc cgc ctg     336
Ser His Ser Ala Thr Arg Ser Arg Gly Gly Gly Gly Thr Ser Arg Leu
         95                  100                105 gag ggc cta cag tca gaa aac cat cgc ctg cga atg aag atc aca gag     384
Glu Gly Leu Gln Ser Glu Asn His Arg Leu Arg Met Lys Ile Thr Glu
110                  115                120                125 ctg gat aaa gac ttg gaa gag gtc acc atg cag ctg cag gac gtc gga     432
Leu Asp Lys Asp Leu Glu Glu Val Thr Met Gln Leu Gln Asp Val Gly
```

```
                     130                 135                 140
ggt tgc gcg gcc gct tat cca tac gac gta cca gac tac gca gga ggt       480
Gly Cys Ala Ala Ala Tyr Pro Tyr Asp Val Pro Asp Tyr Ala Gly Gly
            145                 150                 155 cat cac cat cat cac cat tag gga ggc ggt act gtt gaa agt tgt ctg       528
His His His His His His  *  Gly Gly Gly Thr Val Glu Ser Cys Leu
        160                 165                 170 cgt aat aag gag tct taagtcgac                                          552
Arg Asn Lys Glu Ser
        175
```

<210> SEQ ID NO 18
<211> LENGTH: 185
<212> TYPE: PRT
<213> ORGANISM: Artificial Sequence
<220> FEATURE:
<223> OTHER INFORMATION: Bluescript vector

<400> SEQUENCE: 18

```
Met Lys Lys Ser Leu Val Leu Lys Ala Ser Val Ala Val Ala Thr Leu
  1               5                  10                  15

Val Pro Met Leu Ser Phe Ala Ser Arg Gly Gly Gly Gly Glu Glu Lys
            20                  25                  30

Ser Arg Leu Leu Glu Lys Glu Asn Arg Glu Leu Glu Lys Ile Ile Ala
        35                  40                  45

Glu Lys Glu Glu Arg Val Ser Glu Leu Arg His Gln Leu Gln Ser Val
    50                  55                  60

Gly Gly Cys Gly Ala Pro Gln Phe His Ser Lys Glu Val Leu Met Lys
65                  70                  75                  80

Lys Leu Leu Phe Ala Ile Pro Leu Val Val Pro Phe Tyr Ser His Ser
                85                  90                  95

Ala Thr Arg Ser Arg Gly Gly Gly Gly Thr Ser Arg Leu Glu Gly Leu
            100                 105                 110

Gln Ser Glu Asn His Arg Leu Arg Met Lys Ile Thr Glu Leu Asp Lys
        115                 120                 125

Asp Leu Glu Glu Val Thr Met Gln Leu Gln Asp Val Gly Gly Cys Ala
    130                 135                 140

Ala Ala Tyr Pro Tyr Asp Val Pro Asp Tyr Ala Gly Gly His His His
145                 150                 155                 160

His His His Arg Ser Gly Gly Gly Thr Val Glu Ser Cys Leu Ala Lys
                165                 170                 175

Ala Asn Ile Leu Arg Asn Lys Glu Ser
            180                 185
```

<210> SEQ ID NO 19
<211> LENGTH: 549
<212> TYPE: DNA
<213> ORGANISM: Artificial Sequence
<220> FEATURE:
<221> NAME/KEY: CDS
<222> LOCATION: (1)...(540)
<223> OTHER INFORMATION: Bluescript vector
<220> FEATURE:
<223> OTHER INFORMATION: Bluescript primer

<400> SEQUENCE: 19

```
atg aaa tac cta ttg cct acg gca gcc gct gga ttg tta tta ctc gcg        48
Met Lys Tyr Leu Leu Pro Thr Ala Ala Ala Gly Leu Leu Leu Leu Ala
  1               5                  10                  15 gcc cag ccg gcc atg gcg tct aga ggt gga gga ggt gag gag aag tcc       96
```

```
                                                                                144
cgg ctg ttg gag aag gag aac cgt gaa ctg gaa aag atc att gct gag
Arg Leu Leu Glu Lys Glu Asn Arg Glu Leu Glu Lys Ile Ile Ala Glu
         35                  40                  45

192
aaa gag gag cgt gtc tct gaa ctg cgc cat caa ctc cag tct gta gga
Lys Glu Glu Arg Val Ser Glu Leu Arg His Gln Leu Gln Ser Val Gly
 50                  55                  60

240
ggt tgt taa tag ggc gcg cca caa ttt cac agt aag gag gtt taa ctt
Gly Cys  *   *  Gly Ala Pro Gln Phe His Ser Lys Glu Val  *  Leu
 65                  70                  75

288
atg aaa aaa tta tta ttc gca att cct tta gtt gtt cct ttc tat tct
Met Lys Lys Leu Leu Phe Ala Ile Pro Leu Val Val Pro Phe Tyr Ser
         80                  85                  90

336
cac tcc gct acg cgt tct cga gga ggt ggt gga aca tcc cgc ctg gag
His Ser Ala Thr Arg Ser Arg Gly Gly Gly Gly Thr Ser Arg Leu Glu
         95                 100                 105

384
ggc cta cag tca gaa aac cat cgc ctg cga atg aag atc aca gag ctg
Gly Leu Gln Ser Glu Asn His Arg Leu Arg Met Lys Ile Thr Glu Leu
110                 115                 120                 125

432
gat aaa gac ttg gaa gag gtc acc atg cag ctg cag gac gtc gga ggt
Asp Lys Asp Leu Glu Glu Val Thr Met Gln Leu Gln Asp Val Gly Gly
             130                 135                 140

480
tgc gcg gcc gct tat cca tac gac gta cca gac tac gca gga ggt cat
Cys Ala Ala Ala Tyr Pro Tyr Asp Val Pro Asp Tyr Ala Gly Gly His
                 145                 150                 155

528
cac cat cat cac cat tag gga ggc ggt act gtt gaa agt tgt ctg cgt
His His His His His  *  Gly Gly Gly Thr Val Glu Ser Cys Leu Arg
         160                 165                 170

549
aat aag gag tct taagtcgac
Asn Lys Glu Ser
         175
```

<210> SEQ ID NO 20
<211> LENGTH: 184
<212> TYPE: PRT
<213> ORGANISM: Artificial Sequence
<220> FEATURE:
<223> OTHER INFORMATION: Bluescript vector

<400> SEQUENCE: 20

```
Met Lys Tyr Leu Leu Pro Thr Ala Ala Ala Gly Leu Leu Leu Leu Ala
 1               5                  10                  15

Ala Gln Pro Ala Met Ala Ser Arg Gly Gly Gly Gly Glu Glu Lys Ser
             20                  25                  30

Arg Leu Leu Glu Lys Glu Asn Arg Glu Leu Glu Lys Ile Ile Ala Glu
         35                  40                  45

Lys Glu Glu Arg Val Ser Glu Leu Arg His Gln Leu Gln Ser Val Gly
 50                  55                  60

Gly Cys Gly Ala Pro Gln Phe His Ser Lys Glu Val Leu Met Lys Lys
 65                  70                  75                  80

Leu Leu Phe Ala Ile Pro Leu Val Val Pro Phe Tyr Ser His Ser Ala
                 85                  90                  95

Thr Arg Ser Arg Gly Gly Gly Gly Thr Ser Arg Leu Glu Gly Leu Gln
            100                 105                 110

Ser Glu Asn His Arg Leu Arg Met Lys Ile Thr Glu Leu Asp Lys Asp
         115                 120                 125

Leu Glu Glu Val Thr Met Gln Leu Gln Asp Val Gly Gly Cys Ala Ala
     130                 135                 140
```

```
Ala Tyr Pro Tyr Asp Val Pro Asp Tyr Ala Gly Gly His His His His
145                 150                 155                 160

His His Arg Ser Gly Gly Gly Thr Val Glu Ser Cys Leu Ala Lys Ala
            165                 170                 175

Asn Ile Leu Arg Asn Lys Glu Ser
            180

<210> SEQ ID NO 21
<211> LENGTH: 55
<212> TYPE: DNA
<213> ORGANISM: Artificial Sequence
<220> FEATURE:
<223> OTHER INFORMATION: Primer

<400> SEQUENCE: 21
ggaattgtga gcggataaca atttaccggt cacacaggaa acagctatga ccatg         55

<210> SEQ ID NO 22
<211> LENGTH: 55
<212> TYPE: DNA
<213> ORGANISM: Artificial Sequence
<220> FEATURE:
<223> OTHER INFORMATION: Primer

<400> SEQUENCE: 22
catggtcata gctgtttcct gtgtgaccgg taaattgtta tccgctcaca attcc         55

<210> SEQ ID NO 23
<211> LENGTH: 9
<212> TYPE: DNA
<213> ORGANISM: Viral

<400> SEQUENCE: 23 ttaacttta                                                             9

<210> SEQ ID NO 24
<211> LENGTH: 8
<212> TYPE: DNA
<213> ORGANISM: Viral

<400> SEQUENCE: 24 taaggagg                                                              8

<210> SEQ ID NO 25
<211> LENGTH: 68
<212> TYPE: DNA
<213> ORGANISM: Viral

<400> SEQUENCE: 25
atgaaaaagt ctttagtcct caaagcctcc gtagccgttg ctccctcgtt ccgatgctaa    60
gcttcgct                                                             68

<210> SEQ ID NO 26
<211> LENGTH: 66
<212> TYPE: DNA
<213> ORGANISM: Viral

<400> SEQUENCE: 26
atgaaatacc tattgcctac ggcagccgct ggattgttat tactcgcggc ccagccggcc    60
atggcg                                                               66
```

-continued

```
<210> SEQ ID NO 27
<211> LENGTH: 54
<212> TYPE: DNA
<213> ORGANISM: Artificial Sequence
<220> FEATURE:
<223> OTHER INFORMATION: Phage

<400> SEQUENCE: 27
tatccatacg acgtaccaga ctacgcagga ggtcatcacc atcatcacca ttag          54

<210> SEQ ID NO 28
<211> LENGTH: 57
<212> TYPE: DNA
<213> ORGANISM: Artificial Sequence
<220> FEATURE:
<223> OTHER INFORMATION: Phage

<400> SEQUENCE: 28
atgaaaaaat tattattcgc aattccttta gttgttcctt tctattctca ctccgct       57

<210> SEQ ID NO 29
<211> LENGTH: 4
<212> TYPE: PRT
<213> ORGANISM: Artificial Sequence
<220> FEATURE:
<223> OTHER INFORMATION: BlueScript

<400> SEQUENCE: 29

Val Gly Gly Cys
 1

<210> SEQ ID NO 30
<211> LENGTH: 4
<212> TYPE: PRT
<213> ORGANISM: Artificial Sequence
<220> FEATURE:
<223> OTHER INFORMATION: BlueScript

<400> SEQUENCE: 30

Gly Gly Gly Gly
 1
```